United States Patent
Ladel et al.

(10) Patent No.: US 10,221,456 B2
(45) Date of Patent: Mar. 5, 2019

(54) GENETIC MARKERS FOR PREDICTING RESPONSIVENESS TO FPG-18 COMPOUND

(71) Applicant: MERCK PATENT GMBH, Darmstadt (DE)

(72) Inventors: Christoph Hubertus Ladel, Darmstadt (DE); Alix Anne Simone Berton, Biberach an der Riß (DE); Armand Valsesia, Chavannes-Près-renens (CH); Pierre Jacques Farmer, Evians-les-Bains (FR)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/420,076

(22) PCT Filed: Aug. 5, 2013

(86) PCT No.: PCT/EP2013/066421
§ 371 (c)(1),
(2) Date: Feb. 6, 2015

(87) PCT Pub. No.: WO2014/023703
PCT Pub. Date: Feb. 13, 2014

(65) Prior Publication Data
US 2015/0218637 A1 Aug. 6, 2015

Related U.S. Application Data

(60) Provisional application No. 61/680,480, filed on Aug. 7, 2012, provisional application No. 61/778,912, filed on Mar. 13, 2013.

(30) Foreign Application Priority Data

Aug. 6, 2012 (EP) ..................................... 12179391

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2010/0016223 A1* | 1/2010 | Gimona | A61K 38/1825 514/1.1 |
| 2010/0098775 A1* | 4/2010 | Bukowski | C12Q 1/6883 514/1.1 |
| 2012/0115137 A1 | 5/2012 | Kornman et al. | |

FOREIGN PATENT DOCUMENTS

| WO | WO 2008/023063 | 2/2008 |
|---|---|---|
| WO | WO 2009/135218 | 11/2009 |
| WO | WO 2014/023704 | 2/2014 |

OTHER PUBLICATIONS

Mummidi et al Evolution of human and non human primate CC chemokine receptor 5 gene and mRNA. Journal of Biological Chemistry 2000 vol. 275, No. 25, pp. 18946-18961.*

Kerkhof, H. J. M. et al. "Large-scale meta-analysis of interleukin-1 beta and interleukin-1 receptor antagonist polymorphisms on risk of radiographic hip and knee osteoarthritis and severity of knee osteoarthritis" *Osteoarthritis and Cartilage*, 2011, pp. 265-271, vol. 19.

Bukowski, J. F. et al. "Il-1 RN Polymorphisms Are Associated With Radiographic Severity in Osteoarthritis" A49, *Osteoarthritis and Cartilage*, Sep. 1, 2008, p. S34, vol. 16, Supplement 4.

Wu, X. et al. "Progression or Initiation of Radiographic Knee Osteoarthritis and the Interleukin-1 Receptor Antagonist Gene: The Johnston County Osteoarthritis Project" Poster Presentation #390, *Osteoarthritis and Cartilage*, Oct. 1, 2010, pp. S171-S172, vol. 18, Supplement 2.

Attur, M. et al. "Association of Interleukin-1 Receptor Antagonist (IL-1RN) TTG Haplotype With Radiographic Knee OA Severity in Meta-Analysis" Poster Presentation #391, *Osteoarthritis and Cartilage*, Oct. 1, 2010, p. S172, vol. 18, Supplement 2.

* cited by examiner

*Primary Examiner* — Amanda Haney
(74) *Attorney, Agent, or Firm* — Saliwanchik, Lloyd & Eisenschenk

(57) ABSTRACT

This application is directed to the use of biomarkers for predicting the sensitivity to treatment with an FGF-18 compound of a patient having a cartilage disorder, such as osteoarthritis, cartilage injury, fractures affecting joint cartilage or surgical procedures with impact on joint cartilage (e.g., microfracture), in order to reduce the risk of adverse events and increase the overall benefit after therapy.

7 Claims, 18 Drawing Sheets

Specification includes a Sequence Listing.

SEQ ID NO.1: Amino acid sequence of the native human FGF-18

Met Tyr Ser Ala Pro Ser Ala Cys Thr Cys Leu Cys Leu His Phe Leu
Leu Leu Cys Phe Gln Val Gln Val Leu Val Ala Glu Glu Asn Val Asp
Phe Arg Ile His Val Glu Asn Gln Thr Arg Ala Arg Asp Asp Val Ser
Arg Lys Gln Leu Arg Leu Tyr Gln Leu Tyr Ser Arg Thr Ser Gly Lys
His Ile Gln Val Leu Gly Arg Arg Ile Ser Ala Arg Gly Glu Asp Gly
Asp Lys Tyr Ala Gln Leu Leu Val Glu Thr Asp Thr Phe Gly Ser Gln
Val Arg Ile Lys Gly Lys Glu Thr Glu Phe Tyr Leu Cys Met Asn Arg
Lys Gly Lys Leu Val Gly Lys Pro Asp Gly Thr Ser Lys Glu Cys Val
Phe Ile Glu Lys Val Leu Glu Asn Asn Tyr Thr Ala Leu Met Ser Ala
Lys Tyr Ser Gly Trp Tyr Val Gly Phe Thr Lys Lys Gly Arg Pro Arg
Lys Gly Pro Lys Thr Arg Glu Asn Gln Gln Asp Val His Phe Met Lys
Arg Tyr Pro Lys Gly Gln Pro Glu Leu Gln Lys Pro Phe Lys Tyr Thr
Thr Val Thr Lys Arg Ser Arg Arg Ile Arg Pro Thr His Pro Ala

SEQ ID NO.2: Amino acid sequence of the recombinant truncated FGF-18 (trFGF-18)

Met Glu Glu Asn Val Asp Phe Arg Ile His Val Glu Asn Gln Thr Arg
Ala Arg Asp Asp Val Ser Arg Lys Gln Leu Arg Leu Tyr Gln Leu Tyr
Ser Arg Thr Ser Gly Lys His Ile Gln Val Leu Gly Arg Arg Ile Ser
Ala Arg Gly Glu Asp Gly Asp Lys Tyr Ala Gln Leu Leu Val Glu Thr
Asp Thr Phe Gly Ser Gln Val Arg Ile Lys Gly Lys Glu Thr Glu Phe
Tyr Leu Cys Met Asn Arg Lys Gly Lys Leu Val Gly Lys Pro Asp Gly
Thr Ser Lys Glu Cys Val Phe Ile Glu Lys Val Leu Glu Asn Asn Tyr
Thr Ala Leu Met Ser Ala Lys Tyr Ser Gly Trp Tyr Val Gly Phe Thr
Lys Lys Gly Arg Pro Arg Lys Gly Pro Lys Thr Arg Glu Asn Gln Gln
Asp Val His Phe Met Lys Arg Tyr Pro Lys Gly Gln Pro Glu Leu Gln
Lys Pro Phe Lys Tyr Thr Thr Val Thr Lys

Fig. 16(a)

SEQ ID NO.3: IL1RN gene

```
gggcagctcc acccctgggag ggactgtggc ccaggtactg cccgggtgct actttatggg    60
cagcagctca gttgagttag agtctggaag acctcagaag acctcctgtc ctatgaggcc   120
ctccccatgg ctttaggtaa gctccttcca ctctcatttt ttcacctgag aaatgagaga   180
ggaaaatgtc tacaattggt gtttatcaaa tgctttcagg ctctggtgag caagcgtcca   240
ggaaaatgtc aagcgcatgg agctccaggc ctgtctgggca gatctgggca cgggaggca   300
tccatgggag accatgcagg cactctgagg caggggctgc aagcctagtg cctgctgggg   360
cagcaggtga acagagaggt gtaactgctg tgacagaagt catggagtcc ttggagtgtg   420
agggtcattt tccactgttg atagaatagg gaaattggtg aaatagccct gttaaatgag   480
agaaagaaca gtgtgagctc aatgagaaat actaatagaa tgtggcactg agccacaagg   540
tctgagggtt gattgataag gaagggtggg gactgtggag aattaagggc ttggcacagt   600
cagttccacc agttgtcaca agagaatgca ggctcaggtg ccagaactt ctcgctttc    660
cagaagagtc cgatattctg atttcattat atatagtatt ctgattaaac cagacaataa   720
agcaagcaga taaatatttt aaattataag ctgccagttt gcaacctccg gttaggattt   780
gtgtgggca aagaaaaaaa ctctcaggat cattggtatg tagactctaa ttttaagttt   840
ctaatttaaa attggcccct gaggctgggc gtggtggctc acacctgtaa tcccagcatt   900
ttgggaggcc aaggtgggtg gatctcttga ggtcaagagt tcaaggcctg cctggccaac   960
atggtgaaac cctgtctcta ttaaaaatac aaaaattagc tgggcatggt ggtgcatgtc  1020
tgcaatctta gctacttggg tagctaaggc aggagaattg ctggaacccg ggaggtagag  1080
gttgcagtga atggagatca caccactgca ctccagtctg gcaatagag agagacgctc  1140
tctctaaaaa aaaatatgta aagataaata aaatgaaata aataggcct ctaatgagca   1200
ggccattctc ctttctgggt cttactttcc ttgcactcct ttctgggtgt taagaggagg  1260
tctagaggaa gctggacaac tcttagcttg tagtaagcac agtggaagtg tcagctctta  1320
atgggtcatg gacacgttac aagctaggcg ccttgctgag cactttacat ggtttatccc  1380
actgaaccct ctcaataacc ctatgaggaa gggctattat tgctcacatt ttcagaagag  1440
gaaatggata tagagagatt agataatttg cccatggcca gacagctagt ataagaggag  1500
gaggtggatt gactgcagac attctgtctt caaaccacta cactatgcta tggggggcaca 1560
gagacttaat gaaatcatgg agaggggaat tgctttgtca accacaagca gttattccgg  1620
gggcagcaga tcctcccctg tccccagtg ggtacaatgg tccctggtgg gttgtgctac   1680
aatgttagcc catggtctta tgtgtttttc aaatgtgtaa agtaggatgc tggaaccact  1740
cttagaacca gataccaata cattgtgaag aaataaatct ctgtgcttaa aactggttca  1800
tcccaaaata ttttgaactg acacacaata ggtgctaaat aaatgtgtgt taacttgaat  1860
tggattgaat tcgggaaaaa agtgcaataa gctttagtgaa gacaccatgt tccctgggta  1920
gaggaaccac attctccatc taaggccagg agtatgggag gtatcaatgt ttgcccagca  1980
cagaacaggg tgccaagaag agaaaagttt acggggtgca tactcggact ggaaactgaa  2040
agggtgagaa cagagggtaa aggatagaga tggaaccatg tgcatacact ttgtgttacc  2100
ttggacaagt cattcatttc tctggacctc tgctttctct ctacacaatg gggtcccacc  2160
acttccctta cagctgactt gtatgaagaa ggaggtggag gaggaggaga aggtgaagac  2220
aatgctgact caaagggtaa attattttta ggatccaagt ttgaaaacaa ttttaggcta  2280
ctagatatga acaacatctt gattatgtag ttgaaggaaa ttaaagatga atggtttaat  2340
taaaaattaa tcagaatgaa aacgattgat tactaatata tctgcaagtg tttattttcc  2400
tgagtggcag actcactaag gttttgaat actcctgtgt gattgctcta tgtatgtatg   2460
tatgtatgta tgtatgcatg tatctatcta tctgttgtct aataaaatgg atcacatctc  2520
tgctaataaa aacactacac tggcagggta caattataat cattaactgt gcctggaatt  2580
tgcagcagca gccaccagag gtaccagtgc cctttaaggg ttcataattt agaataatcc  2640
aattatctga gttttttcagg gactgagggg tttggcaagg tgtagaactt tcagtaataa  2700
agtcaagaaa gtcctggaca aaccaaggta gttggtcact ctagtccata accaggtaaa  2760
gagctttccc tgtaacctgt gtaaggtttt agaatcattt cttttccttat taccaaaaat  2820
cctccccaaa ttttcaagaa attatgaact aaatagttac tctatgagat aggagttcag  2880
cccaaaagaa acaccataag aacaaatata attcttgctt atgttaacca tgcaatgaag  2940
cagagagaaa aagtcagtgg cctctttagg aggactgtag tgtgggaaga aataactaaa  3000
ctgggtttca atcctggcct ggccaggatc tggagcaagt gagttaatct ttctaagcct  3060
tgagtagttt cttcttcttc ttcttcttct tcctccccct tctcctcttc ttcttcctcc  3120
tccttctcct cttcttcttc ttcttcttct tcctcttctt cttcttcctc ctcctcctcc  3180
tcctcttctt cttcttcttc ttcctcttcc tcttcctctt cttcctcttc ctcttattct  3240
tcttcatcgt cttcgtcttc gtcttctttt tattttcaaa gtgaaagcaa gtttattaag  3300
aaagtaaagg aataaaagaa tggccactcc atagacagag tagcctgaac cttgagttct  3360
tctataaagt cactatgaat ttatactcat tttgaaagtg ggtgtcaata tgtctgtcca  3420
ctttgcacag ctgttatgtg gacaaaagga gatctgttgtg aaagtgtaac acagagccta  3480
aactataaca ggtaagcaac acagttgtcc ccttcccat ggtgtctgtt cttctccatt   3540
tcctcctgtc tgcaggggga ttataaaact aatcatcaaa gccaagaagg caagagcaag  3600
catgtaccgc tgaaaacaca agataactgc ataagtaatg actttcagtg cagattcata  3660
gctaacccat aaaactgctgg ggcaaaaatc atcttggaag gctctgaacc tcagaaagga  3720
ttcacagtaa gttaaccatg tagatctgag aggagagtag cttcttgtag ataacagttg  3780
```

Fig. 16(b)

```
gattatatac catgtcctga tccccttcat catccaggag agcagaggtg gtcaccctga   3840
tagcagcaag cctgggggct gcagcttggt gggtagaggt actcaggggt acagatgtct   3900
ccaaacctgt cctgctgcct tagggagctt ctaataagtt gatggatttg gttaaaatta   3960
acttggctac ttggcaggac tgggtcagtg aggaccaaca aaaagaagac atcagattat   4020
accctggggg tttgtatttc ttgtgtttct ttctcttctt tgtactaaaa tatttaccca   4080
tgactgggaa agagcaactg gagtctttgt agcattatct tagcaaaaat ttacaaagtt   4140
tggaaaacaa tattgcccat attgtgtggt gtgtcctgtg acactcagga ttcaagtgtt   4200
ggccgaagcc actaaatgtg agatgaagcc attacaaggc agtgtgcaca tctgtccacc   4260
caagctggat gccaacattt cacaaatagt gcttgcgtga cacaaatgca gttccaggag   4320
gcccaaatga aaatgtttgt actgaaattt gttaaagctt cccgacaaac tagatttatc   4380
agtaaggatt gttttctgca aggggggatga aacttgtggg gtgagccatt tgggctgagg   4440
aggagggagg ttggagctga gaaatgtgga gacaatttcc ctttagaagg actgaatctc   4500
cctgcctctc tggggtgcgg cagccagcag gatccaatgg tgtatatgtc tccccagctc   4560
cccattcagt gatatcatgt cagtagcttg aaattatccg tggtgggagt attatgtcat   4620
ggaaattggc aaatggaaac ttttattgga gattcaattg ttaaactttt accagcacaa   4680
cactgccctg ccttcagagt caatgaccct atccaagttt aatccatctg tccactgtct   4740
ccaacacgat ctttataaaa cacacctgac aacattaccc ttttattcag ttttttaaaa   4800
gataagtttc cagctcatcg ggctggcttt aaaggccatt tctcctctgg acctcaccca   4860
acttttcaaa tcacttttcc taccccctacc tctaaatgct actcaaactc agccatcct   4920
gaataataag acttttgaaa agtagattat gggctgggca cagtggctca cacctgtaat   4980
cccagcactt tgggaggcca agatgggtgg atcacctgag gtcgggagtt cgagaccagc   5040
ctgactaaca tagtgaaacc ctgtctctac taaaaataca aaattagttg ggggtggtgg   5100
cacaagcctg taatcccagc tactcaggag gttgaggcag gggaattgct tgaacctggg   5160
aggcggaggt tgcggtgagc ctagattgct ccactgcact ccagcctggg caacaagagc   5220
gaaactccat ctcaaaaaaa taaataaata aataaagtag attacatcag ataccctgg   5280
cctaggttgt ttatgaccaa ctctcctgct gagaataact agaaaagcta gacaaaacat   5340
atttccaaaa gatctctttg gaggcatcag agaatggcca aggctgtaag gaactgcctg   5400
agcccagaga ggtggagccc agcactggtg ccctttactc ctggggacat gtgctggttt   5460
caaaaacttc agctgagttt ttgagcattc atggaacttg gtgggggaga tgaaatttgt   5520
accttaaatc ctgcctacag ggagggtccc tgataatccc cacccaattt ggaaatctgg   5580
gtcagccttc acaggtactg aagccctcct ctgaatgatc tcaagtcctg ctagggtaga   5640
ggttacctgc ttttgaaagg ctcctggcct acctgtgcag caggagcaaa agtgaaccat   5700
ctcagggtac agataacaat catccagagc cttgaatgac ctctactgtg cttaatatat   5760
agtattcagc agtcagtaaa aaggatttag gcacatgcaa gatgacctgt gtatcaggga   5820
gaaataggca ataaattgag atccagcagg gatttgaatc atggatttga atcagggca   5880
gccttcgaaa gaactgtgga gaatatactc agatttaaaa cataagattg gaatttttgg   5940
cagagaacta acaactgtac aaaaaaggaa ccaaatggaa atcctagaac tgaaagatgc   6000
aattaaccga tgttgagaaa tagccaacat ctattgaaca cttcccatgt ggacagctgt   6060
gctaaacact ttacaggcat caacataaga tgtgtcccct tacagcagtg cagtgtccct   6120
cctaagacat ggacagcctg gtttccctat ctctctgctt catcaaaacc cctttacgtg   6180
gggcttagac actcctgttg tctctagtgt ctagtagcac agggctcagc acatggaagc   6240
cactagatac aatttgatga ccaggacctc cgatgaaagc catgggtgct gattgggaag   6300
gcattgtctt ttatgtgcta tggtcttaaa gcttcatcca ggaagcagaa ctcgggggt   6360
gctgaggacc cagaaccgag aataagatta gtcagagatt tcctgtgggc agaaatcata   6420
aggacgccaa ctgtttgggt gagataagac gaaaccaaga gtggacttgt ggccagaagc   6480
gtgaggaaga gggagagagc ttcccttgcc cccttttcttc ctctccctaa gccacagtga   6540
ttgacagccc cccccctttg gagtcagagc aggctggaga ctggactgga aaaggagggt   6600
gggtcaggat acagagcagg aaggctggga gtgcagggca ggagcaaggg gctggggcat   6660
tcattgtgcc tgatctctcc cactttacct ggggtaaaga agcatatgca aaagccacgg   6720
tgtgagtatt tcccaagtgc cagggtcagg gcatgattca tcacgtgcag catttcattc   6780
aatccttata gtaaccgatg atgtggcttc tattattagc tctatcagat aatgaaactg   6840
agaccaagac aggctctgca cattgtgtgg ggtaatgaca caggggggatt cagacctaga   6900
ctccataact cctgccccag ggaccacccc caccctcacc ctgtgcatgt cgacaaagga   6960
cagactgggc cacttctcag gacacagcgg ggaaatgaca cagagcaggg aggttccagg   7020
agccccgagc gtcttttctc caggagaata ctctctgaat tcagactggg gtcagagaaa   7080
catttaccca ggagccgcag tgtgggtggg gcttttttact tgaaacgctg tctgaagca   7140
gtggccagga tggaactctc caccctacct tggcaagcca cttctcttct gcaatctgta   7200
aggacattgt tgagagaatt atggtcttcc aattccggag ggttgaagaa agacaaatag   7260
gagagaacct atcatagtca ggtgctagct gccttctctt tcagagagtg tgagaataaa   7320
gtgatacact tgattattag caaatacttt ggaaatttta aacgctaata ttcaacacac   7380
tctggaagag gcaaataagt agacaggttc atatacatca tctccttcag ctagtcctca   7440
caaaaacaaa caaatgaata aacaaaattc ttctttggcc ctcataggaa gacactgttt   7500
cttgaacgtg tttcaaaaag gatgggtgac tcactcaagg tcacactgtt tatgaggaca   7560
gtacaggaat acagacatgc cattttgcct gaaaaatcc atcacccagg gaggtgacac   7620
```

Fig. 16(c)

```
aattttgcag aaatgttcta tttcctctga aggatacatt ctttaaacct ttgggaaatt  7680
cattcatagt cttcctcctt tgaaggatta actctctgga cacaaagtgt ttgattctga  7740
tttgttggtt ggaagatgtg ttggttgaga gaaagattct gatttgttgg ttgaaaatag  7800
actcatcaag atcaactgct gtagtagtaa atattttgac attttgtctg tattcctgtg  7860
ctgccctcac aagctgcatc accttgagtg agtcattcat acttttttgt ttgttttttgt  7920
tttggagatg gagtcttact ctgttgccta ggctggagtg cggtggcgtg atcttggctc  7980
actgcgacct ccatctcctg ggttcaagtg atcctcctgc ctcagcctcc cgagtagctg  8040
ggattacagg cacatgccac catccctgct aattttttgca ttttcagtag agacggagtt  8100
tcaccatgtt ggtcaggttg gtcttgaact cctgacctca ggtgatccgc ccacctcagc  8160
ctccccaagt gctgggatta caggtgtgag ccaccgtgcc cagcccagcc atcattttttg  8220
aaacacgttt gagaaatagt gtcttccttt gagggccaag gagacatttt ttttgtttat  8280
ttgtttgttt ttgtgaggac tagctgaagg gggtgatgta tattaacctg cctacttatt  8340
tgcctcttcc cagagtgtga tgaatattag ggtttaaagt ttctgaagca tttgttaata  8400
aagcccgggg ctggaggtca gaagacctgg atttctctgc atacttttgc catcagcaag  8460
ctgtgtgacc ttggacagat ccctttttttg tctaaatctt tctgagtctt cttgaaaaca  8520
atgccaggtt gggacaggat gattgccaag ctcccgtcca gctctaaaac actgcaacgt  8580
atgcttctgc accagcactg tccatcctgt agatcatgca gaaattctct tcaacttttt  8640
cctacccata aaataggagc atgcttacct ttttcctaat gttccaggcc ccgggtctag  8700
aatattgtaa gtaaggaagt taatgtgtat cagagcccat tatgggccag aagttctcct  8760
cttccttcct acacctgctt cctccctccc tccctccctc tttcccttcc ttccttccat  8820
ccatttgtga agaagacatg atcaccctca ttctgagagt gaagagacag aggctcaact  8880
aatgaaatga tttgttcaag gtcacacggg tggcacaagg caagtggcag aggttgaatt  8940
tagacccatt cctgtccaaa tgctgagttt atgtcatcgt cccgagacca taactttaaa  9000
gatgtaagat agtgggaaaa gagttgattt caaagcacct ctcagaagga ctcactttac  9060
atcagggggtc agcagactca ggccaaatcc ggtccattca ccgcttttgc aaagaaagtt  9120
gtagtggaac acagctaggc ttattgattt atggattgcc aacgtcctttt tgtgaaacag  9180
acagctgagc tgagtaatcg tggcgcacaa aacctaaaat atttactatc tcgtccttta  9240
cagaatgttt gccaatctat ggtccggagt ccaaggctgt ccattttttca aagaacacaa  9300
agtgacatga gactgtccca tgtgcaggga gccctatcat tttattatga aaaacggcc  9360
tttctgctca aatctgtttt ttaaaaagtc aacaaacaga ctctgggtac ctgtcaggaa  9420
cagtagggag tttggtttcc attgtgtctct tcttcccagg aactcaatga aggggaaata  9480
gaaatcttaa ttttggggaa attgcacagg ggaaaaggg gagggaatca gttacaacac  9540
tccattgcga cacttagtgg ggttgaaagt gacaaacaga agggttctc ttttttggaaa  9600
tgcgaggagg gtatttccgc ttctcgcagt ggggcagggt ggcagacgcc tagcttgggt  9660
gagtgactat ttctttataa accacaactc tgggcccgca atggcagtcc actgccttgc  9720
tgcagtcaca gaatggaaat ctgcagaggc ctccgcagtc acctaatcac tctcctcctc  9780
ttcctgttcc attcagagac gatctgccga ccctctggga gaaaatccag caagatgcaa  9840
gccttcaggt aaggctaccc caaggaggag aaggtgaggg tggatcagct ggagactgga  9900
aacatatcac agctgccagg ggctgccagg ccccagaggg cctgagaact gggtttgggc  9960
tggagaggat gtccattatt caagaaagag gctgttacat gcatggcctt caggacttgt  10020
gtttcaaaat atcccagatg tggatagtgc gaccggaggg ctgtcttact ttcccagaga  10080
ctcaaggaacc cagtgagtaa tagatgcatg ccaaggagtg ggactgcatg tcaggcctag  10140
ttgaatgtgc tgacagagaa gcagagaggg gcaccagggg cacagcccga aggcccagac  10200
tgatatgggc aaggcctgtc tgtgctgaca tgtcggaggg tcccactctc cagggacctt  10260
ggtttccccg tctgtgacat ctgtgacatg agagtcacga taactccttg tgtgccttac  10320
agggttgttg tgaaaattaa atgcacagat aatagcgtaa cagtattccg tgcattgtaa  10380
agagcctgaa aaccattatg atttgaaaat ggaatcggct ttgtgagacc atcactattg  10440
taaagatgtg atgctgatag aaatgacagg actgcttgtg catgccctct gcagtgtgac  10500
attccagcag tgaaatcatg ttggggtgac ttctccccca ctctgacctt tatgttttgtc  10560
tgggccgagg ctgcaagtcg ggctctgtgg gtgtatgagt gacaagtctc tcccttccag  10620
atatgggac tgtctgcttc cctaggttgc ctctccctgc tctgatcagc tagaagctcc  10680
aggagatcct cctgctgagcc ccagcaggtg atgttttatcc ctccagactg aggctaaatc  10740
tagaaactag gataatcaca aacaggccaa tgctgccata tgcaaagcac tttggtttgc  10800
ctggccaccc ctcgtcgagc atgtgggctc ttcagagcca cctgatgagg tgggtacagt  10860
tagccacact tcacaggtga agaggtgagg cacaggtccc aggtcaggct ggccagagct  10920
ctgtttatta cgtctcacag ctttgagtcc tgctctcaac cagagaggcc ctttaccaag  10980
aagaaaggat tgggacccag aatcaggtca ctggctgagg tagagaggaa gccgggttgt  11040
tcccaagggt agctgctcct gcaggactct gagcaggtca ccagctaatg gaggaaaggc  11100
tctagggaaa gaccctttgc gtctcagact cagagcggat tagctgcaag gtgttccgtc  11160
tcttgaaact tctacctagg tgctatggta gccactagtc tcaggtggct atttaaattt  11220
atacttaaat gaatgaaaat agaagaaaat ttaaaatcca gacccttggt cacactatcc  11280
acatttaaag aggtcaatag ccacatgtgg ttagtggcca ccctattggg cagtgcagct  11340
acagaacatt tttgcatccc agaaagttct tttggatgtt gctgctctac agcatgcttt  11400
gctgaaacag aagtgccttc cctgggaatc tcagatggga agcaagtaag gagggagtc  11460
aaatgtgggc tcactgctca ccagctgtga gggttgggcc tgcctcttaa ccattgtcag  11520
```

```
cctcagtctt ctcatccatg catgccgtgg gtatactaaa atactatacc cctggaagag  11580
ctggatgcaa atttgacaag ttctgggga cacaggaagg tgccaagcac aaggctgggc  11640
acatggtggc tgtgcactac agctgagtcc ttttccttt cagaatctgg gatgttaacc  11700
agaagacctt ctatctgagg aacaaccaac tagttgctgg atacttgcaa ggaccaaatg  11760
tcaatttaga aggtgagtgg ttgccaggaa agccaatgta tgtgggcatc acgtcacttt  11820
gcccgtctgt ctgcagcagc atggcctgcc tgcacaaacc ctaggtgcaa tgtcctaatc  11880
cttgttgggt ctttgtattc aagtttgaag ctgggagggc ctggctactg aagggcacat  11940
atgagggcag cctgaagagg gtgtggagag gtagagtcta ggtcagaggt cagtgcctat  12000
aggcacagtg gtcccagggc cacagctggg aagggcaaat accagaaggc aaggttgacc  12060
attcccttcc tcaagtgcct attaaggctc catgttccta tgttgttcaa accctaactc  12120
aatcccaaat taatccacca tgtataaggt tgagctatgt ctcttattcc tggacaccat  12180
actcagccat attctggtcc acacattaaa caagctggat gaccttgaag aagcttcacc  12240
cactcgttc ctcagcttc ccttcagtgg gatgatatca actggacaac aggatgtgcg  12300
attcttttag ttccagcctt ccaggatgtt ttcactcccc tgtttgttgt tgtaggatgg  12360
tattacctcc accttccac cttccctatg ccctggttct gtctcctgtg cctcgctctg  12420
aaagtggatg agacctacaa ttcctgtcct ggtagttctc ctaatgaaca cactgaagca  12480
cgaggaagct gagattttg ttgctacatg agagcatgga ggcctcttag ggagagagga  12540
ggttcagaga ctcctaggct cctgtggagc cccactcatg gccttgttca ttttccctgc  12600
ccctcagcaa cactcctatt gacctggagc acaggtatcc tggggaaagt gagggaaata  12660
tggacatcac atggaacaac atccaggaga ctcaggcctc taggagtaac tgggtagtgt  12720
gcatcctggg gaaagtgagg gaaatatgga catcacatgg aacaacatcc aggagactca  12780
ggcctctagg agtaactggg tagtgtgcat cctggggaaa gtgagggaaa tatggacatc  12840
acatggaaca acatccagga gactcaggcc tctaggagta actgggtagt gtgcatcctg  12900
gggaaagtga gggaaatatg gacatcacat ggaacaacat ccaggagact caggcctcta  12960
ggagtaactg ggtagtgtgc ttggtttaat cttctattta cctgcagacc aggaagatga  13020
gacctctctg cccttctgac ctcgggattt tagttttgtg gggaccaggg gagatagaaa  13080
aatacccggg gtctcttcat tattgctgct tcctcttcta ttaacctgac cctcccctct  13140
gttcttcccc agaaaagata gatgtggtac ccattgagcc tcatgctctg ttcttgggaa  13200
tccatggagg gaagatgtgc ctgtcctgtg tcaagtctgg tgatgagacc agactccagc  13260
tggaggtaaa aacatgcttt ggatctcaaa tcacccaaa acccagtggc ttgaaacaac  13320
caaattttt tcttatgatt ctgtgggttg accaggatta gctgggtagt tctgttccat  13380
gtggtggaac atgctgggt cactttgaa gctgcattca gcagagtgcc tggcttgcgc  13440
tgggcatcca aggtggtccc tcatcctcca ggctctcttt ccatgtgatc tctcagtgtt  13500
taagagttag ttggagcttc cttacagcat ggcggctgac ttccaaaagg gattattcca  13560
aaaagagcct caacatgcag gcgcttatta tgacttctgc ttgcatcatc ctattggcca  13620
aagccagtca cgtggctaag tctagccccc tgtgagagga gactgcataa gagtgtgaac  13680
accaggagac acggtcactg ggggccacca ctgtaaccat ctaccacagg acctgaatct  13740
ctgtgtgcta ctcccttgct caagggcccc cctacccacg cagacctgct gtcttctagc  13800
aaagcccatc ctcaggacct ttctcttcca atccttattg actcaaattg attagttggt  13860
gctccaccca gagccctgtg ctcctttatc tcatgtaatg ttaatgggtt tcccagcct  13920
gggaaaacat ggctttgtct caggggcttg ctggatgcaa gcttaacctc aatgtgagtg  13980
gccatactgt ggcactgtcc catccctcac cagggacact gttctggagg gtgactgcct  14040
gttctgtgag gagtggggat ggctaggaca ttgcatggaa cacaccacca cccatcttc  14100
tcagagctca aaccctgaca gaacaccagc ttcacaggcc ttggcttctg ctgatggtca  14160
cgtgtattta ccagacttag tggtccaagg ccagagtggc cagatttccc aaagtcaagg  14220
tgtgacagtg ggacagcctc tttgtgtctt tgctgtccta agaaacctgg gccaggccag  14280
gcgcagtggc tcacgcctgt aatcccagca ctttgagaag ccaaggtggg cagatcacga  14340
ggtcaggagt ttgagaccag cctggccaac atggtgaaac cctgtctcta ttaaaaatag  14400
aaaacattag acaggtgtgg tggtgcatgc ctgtaatccc agctactcag gaggctgagg  14460
caggagaatc gcttgaaccc aggaggtgga ggttgcagtg agccgagatt gtgccactgc  14520
actccagcct aggcgacaga gcaagactcc gtctcgggaa aattaattaa taaataaata  14580
aacctaggtc ccagagtccc acagaatggc agacaggagc acctggggc ttttagggta  14640
tggcatttcc cctgtactaa ctctgggctg tccagagggc catttcatgg cgtggagtgg  14700
agaggaggc agcacaggac ttcctaggcc tcagctctca cctgcccatc ttttgatttc  14760
caggcagtta acatcactga cctgagcgag aacagaaagc aggacaagcg cttcgccttc  14820
atccgctcag acagtggccc caccaccagt tttgagtctg ccgcctgcc cggttggttc  14880
ctctgcacag cgatggaagc tgaccagccc gtcagcctca ccaatatgcc tgacgaaggc  14940
gtcatggtca ccaaattcta cttccaggag gacgagtagt actgcccagg cctgcctgtt  15000
cccattcttg catggcaagg actgcaggga ctgccagtcc ccctgcccca gggctcccgg  15060
ctatggggc actgaggacc agccattgag gggtggaccc tcagaaggcg tcacaacaac  15120
ctggtcacag gactctgcct cctcttcaac tgaccagcct ccatgctgcc tccagaatgg  15180
tctttctaat gtgtgaatca gagcacagca gcccctgcac aaagcccttc catgtcgcct  15240
ctgcattcag gatcaaaccc cgaccacctg cccaacctgc tctcctcttg ccactgcctc  15300
ttcctccctc attccacctt cccatgccct ggatccatca ggccacttga tgaccccaa   15360
```

Fig. 16(e)

```
ccaagtggct cccacaccct gttttacaaa aaagaaaaga ccagtccatg agggaggttt      15420
ttaagggttt gtggaaaatg aaaattagga tttcatgatt ttttttttc  agtccccgtg      15480
aaggagagcc cttcatttgg agattatgtt ctttcgggga gaggctgagg acttaaaata      15540
ttcctgcatt tgtgaaatga tggtgaaagt aagtggtagc ttttcccttc ttttcttct       15600
tttttgtga  tgtcccaact tgtaaaaatt aaaagttatg gtactatgtt agccccataa      15660
tttttttttt ccttttaaaa cacttccata atctggactc ctctgtccag gcactgctgc      15720
ccagcctcca agctccatct ccactccaga ttttttacag ctgcctgcag tactttacct      15780
cctatcagaa gtttctcagc tcccaaggct ctgagcaaat gtggctcctg ggggttcttt      15840
cttcctctgc tgaaggaata aattgctcct tgacattgta gagcttctgg cacttggaga      15900
cttgtatgaa agatggctgt gcctctgcct gtctccccca ccgggctggg agctctgcag      15960
agcaggaaac atgactcgta tatgtctcag gtccctgcag ggccaagcac ctagcctcgc      16020
tcttggcagg tactcagcga atgaatgctg tatatgttgg gtgcaaagtt ccctacttcc      16080
tgtgacttca gctctgtttt acaataaaat cttgaaaatg ccta                       16124
```

Fig. 16(f)

SEQ ID NO.4: IL1RN rs9005 locus

```
aattaggatt tcatgatttt ttttttttcag tccccgtgaa ggagagccct tcatttggag      60
attatgttct ttcggggaga ggctgaggac ttaaaatatt cctgcatttg tgaaatgatg     120
gtgaaagtaa gtggtagctt ttcccttctt tttcttcttt ttttgtgatg tcccaacttg     180
taaaaattaa aagttatggt actatgttag ccccataatt ttttttttcc ttttaaaaca     240
cttccataat ctggactcct ctgtccaggc actgctgccc agcctccaag ctccatctcc     300
actccagatt ttttacagct gcctgcagta ctttacctcc tatcagaagt ttctcagctc     360
ccaaggctct gagcaaatgt ggctcctggg ggttctttct tcctctgctg aaggaataaa     420
ttgctccttg acattgtaga gcttctggca cttggagact tgtatgaaag atggctgtgc     480
ctctgcctgt ctcccccacc rggctggagc ctctgcagag caggaaacat gactcgtata     540
tgtctcaggt ccctgcaggg ccaagcacct agcctcgctc ttggcaggta ctcagcgaat     600
gaatgctgta tatgttgggt gcaaagttcc ctacttcctg tgacttcagc tctgttttac     660
aataaaatct tgaaaatgcc tatattgtta actatgtcct tggccttgac aggctttggg     720
tatagagtgc tgaggaaact gaaagaccaa tgtgtctttc ttaccccaga ggctggcgcc     780
tggcctcttc tctgagagtt cttttcttcc ttcagcctca ctctccctgg ataacatgag     840
agcaaatctc tctgcaaaaa agatatgggg cagcactgtc cacaacagcc tctgctggaa     900
acaacccaag cacccatcac agaatgaatt agtacatcat gtatctgcac acaacacagt     960
gctccttggc aaagaaaatg aatgaattac agccagctgc a                        1001
```

SEQ ID NO.5: IL1RN rs315952 locus

```
tcacgaggtc agcagtttga gaccagcctg gccaacatgg tgaaaccctg tctctattaa      60
aaatagaaaa cattagacag gtgtggtggt gcatgcctgt aatcccagct actcaggagg     120
ctgaggcagg agaatcgctt gaacccagga ggtggaggtt gcagtgagcc gagattgtgc     180
cactgcactc cagcctaggc gacagagcaa gactccgtct cgggaaaatt aattaataaa     240
taaataaacc tacgtcccag agtcccacag aatggcagac aggagcacct ggggcttttt     300
agggtatggc atttcccctg tactaactct gggctgtcca gagggccatt tcatggcgtg     360
gagtggagag ggaggcagca caggacttcc taggcctcag ctctcacctg cccatctttt     420
gatttccagg cagttaacat cactgaccctg agaagcagga caagcgcttc                480
gccttcatcc gctcagacag yggccccacc accagttttg agtctgccgc ctgccccggt     540
tggttcctct gcacagcgat ggaagctgac cagcccgtca gcctcaccaa tatgcctgac     600
gaaggcgtca tggtcaccaa attctacttc caggaggacg agtagtactg cccaggcctg     660
cctgttccca ttcttgcatg gcaaggactg cagggactgc cagtcccct gccccagggc     720
tcccggctat ggggcactg aggaccagcc attgaggggg ggaccctcag aaggcgtcac     780
aacaacctgg tcacaggact ctgcctcctc ttcaactgac cagcctccat gctgcctcca     840
gaatggtctt tctaatgtgt gaatcagagc acagcagccc ctgcacaaag cccttccatg     900
tcgcctctgc attcaggatc aaaccccgac cacctgccca acctgctctc ctcttgccac     960
tgcctcttcc tccctcattc caccttccca tgccctggat c                        1001
```

SEQ ID NO.6: Specific region from IL1RN rs9005 locus (corresponding to nucleotide 415 to nucleotide 466 of SEQ ID NO.4), wherein N is A or G

```
<221> variation
<222> (27)..(27)
<223> n is a or g
ctgtgcctct gcctgtctcc cccaccnggc tgggagctct gcagagcagg aa          52
```

SEQ ID NO.7: Specific region from IL1RN rs315952 locus (corresponding to nucleotide 415 to nucleotide 466 of SEQ ID NO.5), wherein N is C or T

```
<221> variation
<222> (27)..(27)
<223> n is c or t
cgcttcgcct tcatccgctc agacagnggc cccaccacca gttttgagtc tg          52
```

SEQ ID NO.8: rs315952 primer 1

```
gcttcgcctt catccgctca gacag                                        25
```

SEQ ID NO.9: rs315952 primer 2

```
ggccccacca ccagttttga gtctg                                        25
```

SEQ ID NO.10: rs9005 primer 1

```
tgtgcctctg cctgtctccc ccacc                                        25
```

SEQ ID NO.11: rs9005 primer 2

```
ggctgggagc tctgcagagc aggaa                                        25
```

Fig. 16(h)

SEQUENCE LISTING

```
<160> NUMBER OF SEQ ID NOS: 11

<210> SEQ ID NO 1
<211> LENGTH: 207
<212> TYPE: PRT
<213> ORGANISM: Homo sapiens

<400> SEQUENCE: 1

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
```

```
                145                 150                 155                 160
Lys Gly Pro Lys Thr Arg Glu Asn Gln Gln Asp Val His Phe Met Lys
                    165                 170                 175
Arg Tyr Pro Lys Gly Gln Pro Glu Leu Gln Lys Pro Phe Lys Tyr Thr
                180                 185                 190
Thr Val Thr Lys Arg Ser Arg Ile Arg Pro Thr His Pro Ala
                    195                 200                 205

<210> SEQ ID NO 2
<211> LENGTH: 170
<212> TYPE: PRT
<213> ORGANISM: artificial sequence
<220> FEATURE:
<223> OTHER INFORMATION: Truncated FGF-18

<400> SEQUENCE: 2

Met Glu Glu Asn Val Asp Phe Arg Ile His Val Glu Asn Gln Thr Arg
1               5                   10                  15
Ala Arg Asp Asp Val Ser Arg Lys Gln Leu Arg Leu Tyr Gln Leu Tyr
                20                  25                  30
Ser Arg Thr Ser Gly Lys His Ile Gln Val Leu Gly Arg Arg Ile Ser
            35                  40                  45
Ala Arg Gly Glu Asp Gly Asp Lys Tyr Ala Gln Leu Leu Val Glu Thr
        50                  55                  60
Asp Thr Phe Gly Ser Gln Val Arg Ile Lys Gly Lys Glu Thr Glu Phe
65                  70                  75                  80
Tyr Leu Cys Met Asn Arg Lys Gly Lys Leu Val Gly Lys Pro Asp Gly
                85                  90                  95
Thr Ser Lys Glu Cys Val Phe Ile Glu Lys Val Leu Glu Asn Asn Tyr
                100                 105                 110
Thr Ala Leu Met Ser Ala Lys Tyr Ser Gly Trp Tyr Val Gly Phe Thr
            115                 120                 125
Lys Lys Gly Arg Pro Arg Lys Gly Pro Lys Thr Arg Glu Asn Gln Gln
        130                 135                 140
Asp Val His Phe Met Lys Arg Tyr Pro Lys Gly Gln Pro Glu Leu Gln
145                 150                 155                 160
Lys Pro Phe Lys Tyr Thr Thr Val Thr Lys
                165                 170

<210> SEQ ID NO 3
<211> LENGTH: 16124
<212> TYPE: DNA
<213> ORGANISM: Homo sapiens

<400> SEQUENCE: 3
gggcagctcc accctgggag ggactgtggc ccaggtactg cccgggtgct actttatggg      60
cagcagctca gttgagttag agtctggaag acctcagaag acctcctgtc ctatgaggcc     120
ctccccatgg ctttaggtaa gctccttcca ctctcatttt ttcacctgag aaatgagaga     180
ggaaaatgtc tacaattggt gtttatcaaa tgctttcagg ctctggtgag caagcgtcca     240
ggaaaatgtc aagcgcatgg agctccaggc ctgtctgggg gatctgggca cggggaggca     300
tccatgggag accatgcagg cactctgagg caggggctgc aagcctagtg cctgctgggg     360
cagcaggtga acagagaggt gtaactgctg tgacagaagt catggagtcc ttggagtgtg     420
aggtcatttt tccactgttg atagaatagg gaaattggtg aaatagccct gttaaatgag     480
agaaagaaca gtgtgagctc aatgagaaat actaatagaa tgtggcactg agccacaagg     540
```

```
tctgagggtt gattgataag gaagggtggg gactgtggag aattaagggc ttggcacagt    600
cagttccacc agttgtcaca agagaatgca ggctcaggtg gccagaactt ctcgcttttc    660
cagaagagtc cgatattctg atttcattat atatagtatt ctgattaaac cagacaataa    720
agcaagcaga taaaatattt aaattataag ctgccagttt gcaacctccg gttaggattt    780
gtgtggggca agaaaaaaa ctctcaggat cattggtatg tagactctaa ttttaagttt    840
ctaatttaaa attggcccct gaggctgggc gtggtggctc acacctgtaa tcccagcatt    900
ttgggaggcc aaggtgggtg gatctcttga ggtcaagagt tcaaggcctg cctggccaac    960
atggtgaaac cctgtctcta ttaaaaatac aaaaattagc tgggcatggt ggtgcatgtc   1020
tgcaatctta gctacttggg tagctaaggc aggagaattg ctggaacccg ggaggtagag   1080
gttgcagtga atggagatca caccactgca ctccagtctg gcaatagag agagacgctc   1140 tctctaaaaa aaaatatgta aagataaata aaatgaaata aaataggcct ctaatgagca   1200
ggccattctc ctttctgggt cttactttcc ttgcactcct ttctgggtgt taagaggagg   1260
tctagaggaa gctggacaac tcttagcttg tagtaagcac agtggaagtg tcagctctta   1320
atgggtcatg gacacgttac aagctaggcg ccttgctgag cactttacat ggtttatccc   1380 actgaacccct ctcaataacc ctatgaggaa gggctattat tgctcacatt ttcagaagag   1440
gaaatggata tagagagatt agataaatttg cccatggcca gacagctagt ataagaggag   1500
gaggtggatt gactgcagac attctgtctt caaaccacta cactatgcta tgggggcaca   1560
gagacttaat gaaatcatgg agaggggaat tgctttgtca accacaagca gttattccgg   1620
gggcagcaga tcctcccctg tcccccagtg ggtacaatgg tccctggtgg ttgtgctac   1680 aatgttagcc catggtctta tgtgttttc aaatgtgtaa agtaggatgc tggaaccact   1740
cttagaacca gataccaata cattgtgaag aaataaatct ctgtgcttaa aactggttca   1800
tcccaaaata ttttgaactg acacacaata ggtgctaaat aaatgtgtgt taacttgaat   1860
tggattgaat tcgggaaaaa agtgcaataa gcttagtgaa gacaccatgt tccctgggta   1920
gaggaaccac attctccatc taaggccagg agtatgggag gtatcaatgt ttgcccagca   1980
cagaacaggg tgccaagaag agaaaagttg acggggtgca tactcggact ggaaactgga   2040
agggtgagaa cagagggtaa aggatagaga tggaaccatg tgcatacact ttgtgttacc   2100
ttggacaagt cattcatttc tctggacctc tgctttctct ctacacaatg gggtcccacc   2160
acttccctta cagctgactt gtatgaagaa ggaggtggag gaggaggaga aggtgaagac   2220
aatgctgact caaagggtaa attattttta ggatccaagt ttgaaaacaa ttttaggcta   2280
ctagatatga acaacatctt gattatgtag ttgaaggaaa ttaaagatga atggtttaat   2340
taaaaattaa tcagaatgaa aacgattgat tactaatata tctgcaatgg tttatttcc    2400 tgagtggcag actcactaag gttttttgaat actcctgtgt gattgctcta tgtatgtatg   2460
tatgtatgta tgtatgcatg tatctatcta tctgttgtct aataaaatgg atcacatctc   2520
tgctaataaa aacactacac tggcagggta caattataat cattaactgt gcctggaatt   2580
tgcagcagca gccaccagag gtaccagtgc cctttaaggg ttcataattt agaataatcc   2640
aattatctga gtttttcagg gactgagggg tttggcaagg tgtagaactt tcagtaataa   2700
agtcaagaaa gtcctggaca aaccaaggta gttggtcact ctagtccata accaggtaaa   2760
gagctttccc tgtaacctgt gtaaggtttt agaatcattt ctttccttat taccaaaaat   2820
cctccccaaa ttttcaagaa attatgaact aaatagttac tctatgagat aggagttcag   2880
```

| | | | | | |
|---|---|---|---|---|---|
| cccaaaagaa | acaccataag | aacaaatata | attcttgctt | atgttaacca | tgcaatgaag | 2940
| cagagagaaa | aagtcagtgg | cctctttagg | aggactgtag | tgtgggaaga | aataactaaa | 3000
| ctgggtttca | atcctggcct | ggccaggatc | tggagcaagt | gagttaatct | ttctaagcct | 3060
| tgagtagttt | cttcttcttc | ttcttcttct | tcctcccct | tctcctcttc | ttcttcctcc | 3120
| tccttctcct | cttcttcttc | ttcttcttct | tcctcttctt | cttcttcctc | ctcctcctcc | 3180
| tcctcttctt | cttcttcttc | ttcctcttcc | tcttcctctt | cttcctcttc | ctcttattct | 3240
| tcttcatcgt | cttcgtcttc | gtcttctttt | tattttcaaa | gtgaaagcaa | gtttattaag | 3300
| aaagtaaagg | aataaaagaa | tggccactcc | atagacagag | tagcctgaac | cttgagttct | 3360
| tctataaagt | cactatgaat | ttatactcat | tttgaaagtg | ggtgtcaata | tgtctgtcca | 3420
| ctttgcacag | ctgttatgtg | gacaaaagga | gatctgtgtg | aaagtgtaac | acagagccta | 3480
| aactataaca | ggtaagcaac | acagttgtcc | ccttccccat | ggtgtctgtt | cttctccatt | 3540
| tcctcctgtc | tgcaggggga | ttataaaact | aatcatcaaa | gccaagaagg | caagagcaag | 3600
| catgtaccgc | tgaaaacaca | agataactgc | ataagtaatg | actttcagtg | cagattcata | 3660
| gctaacccat | aaactgctgg | ggcaaaaatc | atcttggaag | gctctgaacc | tcagaaagga | 3720
| ttcacagtaa | gttaaccatg | tagatctgag | aggagagtag | cttcttgtag | ataacagttg | 3780
| gattatatac | catgtcctga | tccccttcat | catccaggag | agcagaggtg | gtcaccctga | 3840
| tagcagcaag | cctgggggct | gcagcttggt | gggtagaggt | actcagggt | acagatgtct | 3900
| ccaaacctgt | cctgctgcct | tagggagctt | ctaataagtt | gatggatttg | gttaaaatta | 3960
| acttggctac | ttggcaggac | tgggtcagtg | aggaccaaca | aaaagaagac | atcagattat | 4020
| accctggggg | tttgtatttc | ttgtgtttct | ttctcttctt | tgtactaaaa | tatttaccca | 4080
| tgactgggaa | agagcaactg | gagtctttgt | agcattatct | tagcaaaaat | ttacaaagtt | 4140
| tggaaaacaa | tattgcccat | attgtgtggt | gtgtcctgtg | acactcagga | ttcaagtgtt | 4200
| ggccgaagcc | actaaatgtg | agatgaagcc | attacaaggc | agtgtgcaca | tctgtccacc | 4260
| caagctggat | gccaacattt | cacaaatagt | gcttgcgtga | cacaaatgca | gttccaggag | 4320
| gcccaaatga | aaatgtttgt | actgaaattt | gttaaagctt | cccgacaaac | tagatttatc | 4380
| agtaaggatt | gttttctgca | aggggatga | aacttgtggg | gtgagccatt | tgggctgagg | 4440
| aggagggagg | ttggagctga | gaaatgtgga | gacaatttcc | ctttagaagg | actgaatctc | 4500
| cctgcctctc | tggggtgcgg | cagccagcag | gatccaatgg | tgtatatgtc | tccccagctc | 4560
| cccattcagt | gatatcatgt | cagtagcttg | aaattatccg | tggtgggagt | attatgtcat | 4620
| ggaaattggc | aaatggaaac | ttttattgga | gattcaattg | ttaaactttt | accagcacaa | 4680
| cactgccctg | ccttcagagt | caatgaccct | atccaagttt | aatccatctg | tccactgtct | 4740
| ccaacacgat | ctttataaaa | cacacctgac | aacattaccc | ttttattcag | ttttttaaaa | 4800
| gataagtttc | cagctcatcg | ggctggcttt | aaaggccatt | tctcctctgg | acctcaccca | 4860
| acttttcaaa | tcacttttcc | taccctacc | tctaaatgct | actcaaactc | cagccatcct | 4920
| gaataataag | acttttgaaa | agtagattat | gggctgggca | cagtggctca | cacctgtaat | 4980
| cccagcactt | tgggaggcca | agatgggtgg | atcacctgag | gtcgggagtt | cgagaccagc | 5040
| ctgactaaca | tagtgaaacc | ctgtctctac | taaaaataca | aaattagttg | ggggtggtgg | 5100
| cacaagcctg | taatcccagc | tactcaggag | gttgaggcag | gggaattgct | tgaacctggg | 5160
| aggcggaggt | tgcggtgagc | ctagattgct | ccactgcact | ccagcctggg | caacaagagc | 5220
| gaaactccat | ctcaaaaaaa | taaataaata | aataaagtag | attacatcag | atacctctgg | 5280

```
cctaggttgt ttatgaccaa ctctcctgct gagaataact agaaaagcta gacaaaacat    5340
atttccaaaa gatctctttg gaggcatcag agaatggcca aggctgtaag gaactgcctg    5400
agcccagaga ggtggagccc agcactggtg ccctttactc ctggggacat gtgctggttt    5460
caaaaacttc agctgagttt ttgagcattc atggaacttg gtgggggaga tgaaatttgt    5520
accttaaatc ctgcctacag ggagggtccc tgataatccc cacccaattt ggaaatctgg    5580
gtcagccttc acaggtactg aagccctcct ctgaatgatc tcaagtcctg ctagggtaga    5640
ggttacctgc ttttgaaagg ctcctggcct acctgtgcag caggagcaaa agtgaaccat    5700
ctcagggtac agataacaat catccagagc cttgaatgac ctctactgtg cttaatatat    5760
agtattcagc agtcagtaaa aaggatttag gcacatgcaa gatgacctgt gtatcaggga    5820
gaaataggca ataaattgag atccagcagg gatttgaatc atggatttga atcaggggca    5880
gccttcgaaa gaactgtgga gaatatactc agatttaaaa cataagattg gaattttttgg   5940 cagagaacta caactgtac aaaaaaggaa ccaaatggaa atcctagaac tgaaagatgc     6000
aattaaccga tgttgagaaa tagccaacat ctattgaaca cttcccatgt ggacagctgt    6060
gctaaacact ttacaggcat caacataaga tgtgtcccct tacagcagtg cagtgtccct    6120
cctaagacat ggacagcctg gtttccctat ctctctgctt catcaaaacc cctttacgtg    6180
gggcttagac actcctgttg tctctagtgt ctagtagcac agggctcagc acatggaagc    6240
cactagatac aatttgatga ccaggacctc cgatgaaagc catgggtgct gattgggaag    6300
gcattgtctt ttatgtgcta tggtcttaaa gcttcatcca ggaagcagaa ctcgggggt     6360 gctgaggacc cagaaccgag aataagatta gtcagagatt tcctgtgggc agaaatcata    6420
aggacgccaa ctgtttgggt gagataagac gaaaccaaga gtggacttgt ggccagaagc    6480
gtgaggaaga gggagagagc ttcccttgtc ccctttcttc ctctccctaa gccacagtga    6540
ttgacagccc ccccccttg gagtcagagc aggcttgaga ctggactggg aaaggagggt     6600
gggtcaggat acagagcagg aaggctggga gtgcagggca ggagcaaggg gctggggcat    6660
tcattgtgcc tgatctctcc cactttacct ggggtaaaga agcatatgca aaagccacgg    6720
tgtgagtatt tcccaagtgc cagggtcagg gcatgattca tcacgtgcag catttcattc    6780
aatccttata gtaaccgatg atgtggcttc tattattagc tctatcagat aatgaaactg    6840
agaccaagac aggctctgca cattgtgtgg ggtaatgaca caggggggatt cagacctaga   6900 ctccataact cctgcccag ggaccacccc caccctcacc ctgtgcatgt cgacaaagga    6960
cagactgggc cacttctcag gacacagcgg ggaaatgaca cagagcaggg aggttccagg    7020
agccccgagc gtcttttctc caggagaata ctctctgaat tcagactggg gtcagagaaa    7080
catttaccca ggagccgcag tgtgggtggg cttttttact tgaaacgctg tctgaaggca    7140
gtggccagga tggaactctc caccctacct tggcaagcca cttctcttct gcaatctgta    7200
aggacattgt tgagagaatt atggtcttcc aattccggag ggttgaagaa agacaaatag    7260
gagagaacct atcatagtca ggtgctagct gccttctctt tcagagagtg tgagaataaa    7320
gtgatacact tgattattag caaatacttt ggaaattta aacgctaata ttcaacacac    7380
tctggaagag gcaaataagt agacaggttc atatacatca tctccttcag ctagtcctca    7440
caaaaacaaa caaatgaata aacaaaattc ttctttggcc ctcataggaa gacactgttt    7500
cttgaacgtg tttcaaaaag gatgggtgac tcactcaagg tcacactgtt tatgaggaca    7560
gtacaggaat acagacatgc catttttgcct gaaaaaatcc atcacccagg gaggtgacac   7620
```

```
aattttgcag aaatgttcta tttcctctga aggatacatt ctttaaacct tgggaaatt    7680 cattcatagt cttcctcctt tgaaggatta actctctgga cacaaagtgt ttgattctga    7740
tttgttggtt ggaagatgtg ttggttgaga aaagattct gatttgttgg ttgaaaatag    7800
actcatcaag atcaactgct gtagtagtaa atattttgac attttgtctg tattcctgtg    7860
ctgccctcac aagctgcatc accttgagtg agtcattcat actttttgt ttgttttttgt    7920 tttggagatg gagtcttact ctgttgccta ggctggagtg cggtggcgtg atcttggctc    7980
actgcgacct ccatctcctg ggttcaagtg atcctcctgc ctcagcctcc cgagtagctg    8040
ggattacagg cacatgccac catccctgct aattttttgca ttttcagtag agacggagtt    8100
tcaccatgtt ggtcaggttg gtcttgaact cctgacctca ggtgatccgc ccacctcagc    8160
ctccccaagt gctgggatta caggtgtgag ccaccgtgcc cagcccagcc atcattttg    8220 aaacacgttt gagaaatagt gtcttccttt gagggccaag gagacatttt ttttgtttat    8280
ttgtttgttt ttgtgaggac tagctgaagg gggtgatgta tattaacctg cctacttatt    8340
tgcctcttcc cagagtgtga tgaatattag ggtttaaagt ttctgaagca tttgttaata    8400
aagcccgggg ctggaggtca gaagacctgg atttctctgc atacttttgc catcagcaag    8460
ctgtgtgacc ttgacagat cccttttttg tctaaatctt tctgagtctt cttgaaaaca    8520
atgccaggtt gggacaggat gattgccaag ctcccgtcca gctctaaaac actgcaacgt    8580
atgcttctgc accagcactg tccatcctgt agatcatgca gaaattctct tcaactttt    8640 cctacccata aaataggagc atgcttacct ttttcctaat gttccaggcc ccgggtctag    8700
aatattgtaa gtaaggaagt taatgtgtat cagagcccat tatgggccag aagttctcct    8760
cttccttcct acacctgctt cctccctccc tccctccctc tttcccttcc ttccttccat    8820
ccatttgtga agaagacatg atcaccctca ttctgagagt gaagagacag aggctcaact    8880
aatgaaatga tttgttcaag gtcacacggg tggcacaagg caagtggcag aggttgaatt    8940
tagacccatt cctgtccaaa tgctgagttt atgtcatcgt cccgagacca taactttaaa    9000
gatgtaagat agtgggaaaa gagttgattt caaagcacct ctcagaagga ctcactttac    9060
atcaggggtc agcagactca ggccaaatcc ggtccattcc ccgcttttgc aaagaaagtt    9120
gtagtggaac acagctaggc ttattgattt atggattgcc aacgtccttt tgtgaaacag    9180
acagctgagc tgagtaatcg tggcgcacaa aacctaaaat atttactatc tcgtcccttta    9240 cagaatgttt gccaatctat ggtccggagt ccaaggctgt ccattttttca aagaacacaa    9300 agtgacatga gactgtccca tgtgcaggga gccctatcat tttattatga aaaacggcc    9360 tttctgctca aatctgtttt ttaaaaagtc aacaaacaga ctctgggtac ctgtcaggaa    9420 cagtaggag tttggtttcc attgtgctct tcttcccagg aactcaatga aggggaaata    9480
gaaatcttaa ttttggggaa attgcacagg ggaaaaggg gagggaatca gttacaacac    9540
tccattgcga cacttagtgg ggttgaaagt gacaacagca agggtttctc tttttggaaa    9600
tgcgaggagg gtatttccgc ttctcgcagt ggggcagggt ggcagacgcc tagcttgggt    9660
gagtgactat ttcttttataa accacaactc tgggcccgca atggcagtcc actgccttgc    9720
tgcagtcaca gaatggaaat ctgcagaggc ctccgcagtc acctaatcac tctcctcctc    9780
ttcctgttcc attcagagac gatctgccga ccctctggga gaaaatccag caagatgcaa    9840
gccttcaggt aaggctaccc caaggaggag aaggtgaggg tggatcagct ggagactgga    9900
aacatatcac agctgccagg ggctgccagg ccccagaggg cctgagaact gggtttgggc    9960
tggagaggat gtccattatt caagaaagag gctgttacat gcatgggctt caggacttgt   10020
```

```
gtttcaaaat atcccagatg tggatagtgc gaccggaggg ctgtcttact ttcccagaga    10080
ctcaggaacc cagtgagtaa tagatgcatg ccaaggagtg ggactgcgat tcaggcctag    10140
ttgaatgtgc tgacagagaa gcagagaggg gcaccagggg cacagcccga aggcccagac    10200
tgatatgggc aaggcctgtc tgtgctgaca tgtcggaggg tcccactctc cagggacctt    10260
ggtttccccg tctgtgacat ctgtgacatg agagtcacga taactccttg tgtgccttac    10320
agggttgttg tgaaaattaa atgcacagat aatagcgtaa cagtattccg tgcattgtaa    10380
agagcctgaa aaccattatg atttgaaaat ggaatcggct ttgtgagacc atcactattg    10440
taaagatgtg atgctgatag aaatgacagg actgcttgtg catgccctct gcagtgtgac    10500
attccagcag tgaaatcatg ttggggtgac ttctccccca ctctgacctt tatgtttgtc    10560
tgggccgagg ctgcaagtcg ggctctgtgg gtgtatgagt acaagtctc tcccttccag    10620 atatggggac tgtctgcttc cctaggttgc ctctccctgc tctgatcagc tagaagctcc    10680
aggagatcct cctggaggcc ccagcaggtg atgtttatcc ctccagactg aggctaaatc    10740
tagaaactag gataatcaca aacaggccaa tgctgccata tgcaaagcac tttggtttgc    10800
ctggccaccc ctcgtcgagc atgtgggctc ttcagagcca cctgatgagg tgggtacagt    10860
tagccacact tcacaggtga agaggtgagg cacaggtccc aggtcaggct ggccagagct    10920
ctgtttatta cgtctcacag cttttgagtcc tgctctcaac cagagaggcc ctttaccaag    10980
aagaaaggat tgggacccag aatcaggtca ctggctgagg tagagaggaa gccgggttgt    11040
tcccaagggt agctgctcct gcaggactct gagcaggtca ccagctaatg gaggaaaggc    11100
tctagggaaa gacccttctg gtctcagact cagagcgagt tagctgcaag gtgttccgtc    11160
tcttgaaact tctacctagg tgctatggta gccactagtc tcaggtggct atttaaattt    11220
atacttaaat gaatgaaaat agaagaaaat ttaaaatcca gacccttggt cacactatcc    11280
acatttaaag aggtcaatag ccacatgtgg ttagtggcca ccctattggg cagtgcagct    11340
acagaacatt tttgcatccc agaaagttct tttggatgtt gctgctctac agcatgcttt    11400
gctgaaacag aagtgccttc cctgggaatc tcagatggga agcaagtaag gaggggagtc    11460
aaatgtgggc tcactgctca ccagctgtga gggttgggcc tgcctcttaa ccattgtcag    11520
cctcagtctt ctcatccatg catgccgtgg gtatactaaa atactatacc cctggaagag    11580
ctggatgcaa atttgacaag ttctggggga cacaggaagg tgccaagcac aaggctgggc    11640
acatggtggc tgtgcactac agctgagtcc ttttccttt cagaatctgg gatgttaacc    11700
agaagacctt ctatctgagg aacaaccaac tagttgctgg atacttgcaa ggaccaaatg    11760
tcaatttaga aggtgagtgg ttgccaggaa agccaatgta tgtgggcatc acgtcacttt    11820
gcccgtctgt ctgcagcagc atggcctgcc tgcacaaacc ctaggtgcaa tgtcctaatc    11880
cttgttgggt cttttgtattc aagtttgaag ctgggagggc ctggctactg aagggcacat    11940
atgagggcag cctgaagagg gtgtggagag gtagagtcta ggtcagaggt cagtgcctat    12000
aggcacagtg gtcccagggc cacagctggg aagggcaaat accagaaggc aaggttgacc    12060
attcccttcc tcaagtgcct attaaggctc catgttccta tgttgttcaa accctaactc    12120
aatcccaaat taatccacca tgtataaggt tgagctatgt ctcttattcc tggacaccat    12180
actcagccat attctggtcc acacattaaa caagctggat gaccttgaag aagcttcacc    12240
cactctgttc ctcagctttc ccttcagtgg gatgatatca actggacaac aggatgtgcg    12300
attcttttag ttccagcctt ccaggatgtt ttcactcccc tgtttgttgt tgtaggatgg    12360
```

```
tattacctcc accttcccac cttccctatg ccctggttct gtctcctgtg cctcgctctg   12420
aaagtggatg agacctacaa ttcctgtcct ggtagttctc ctaatgaaca cactgaagca   12480
cgaggaagct gagattttg ttgctacatg agagcatgga ggcctcttag ggagagagga    12540
ggttcagaga ctcctaggct cctgtggagc cccactcatg gccttgttca ttttccctgc   12600
ccctcagcaa cactcctatt gacctggagc acaggtatcc tggggaaagt gagggaaata   12660
tggacatcac atggaacaac atccaggaga ctcaggcctc taggagtaac tgggtagtgt   12720
gcatcctggg gaaagtgagg gaaatatgga catcacatgg aacaacatcc aggagactca   12780
ggcctctagg agtaactggg tagtgtgcat cctggggaaa gtgagggaaa tatgacatc    12840 acatggaaca acatccagga gactcaggcc tctaggagta actgggtagt gtgcatcctg   12900
gggaaagtga gggaaatatg gacatcacat ggaacaacat ccaggagact caggcctcta   12960
ggagtaactg ggtagtgtgc ttggtttaat cttctattta cctgcagacc aggaagatga   13020
gacctctctg cccttctgac ctcgggattt tagttttgtg gggaccaggg gagatagaaa   13080
aatacccggg gtctcttcat tattgctgct tcctcttcta ttaacctgac cctcccctct   13140
gttcttcccc agaaaagata gatgtggtac ccattgagcc tcatgctctg ttcttgggaa   13200
tccatggagg gaagatgtgc ctgtcctgtg tcaagtctgg tgatgagacc agactccagc   13260
tggaggtaaa aacatgcttt ggatctcaaa tcaccccaaa acccagtggc ttgaaacaac   13320
caaaattttt tcttatgatt ctgtgggttg accaggatta gctgggtagt tctgttccat   13380
gtggtggaac atgctggggt cactttggaa gctgcattca gcagagtgcc tggcttgcgc   13440
tgggcatcca aggtggtccc tcatcctcca ggctctcttt ccatgtgatc tctcagtgtt   13500
taagagttag ttggagcttc cttacagcat ggcggctgac ttccaaaagg gattattcca   13560
aaaagagcct caacatgcag gcgcttatta tgacttctgc ttgcatcatc ctattggcca   13620
aagccagtca cgtggctaag tctagccccc tgtgagagga gactgcataa gagtgtgaac   13680
accaggagac acgtcactg ggggccacca ctgtaaccat ctaccacagg acctgaatct    13740
ctgtgtgcta ctcccttgct caagggcccc cctacccacg cagacctgct gtcttctagc   13800
aaagcccatc ctcaggacct ttctcttcca atccttattg actcaaattg attagttggt   13860
gctccaccca gagccctgtg ctcctttatc tcatgtaatg ttaatgggtt tcccagccct   13920
gggaaaacat ggctttgtct caggggcttg ctggatgcaa gcttaacctc aatgtgagtg   13980
gccatactgt ggcactgtcc catccctcac cagggacact gttctggagg gtgactgcct   14040
gttctgtgag gagtggggat ggctaggaca ttgcatggaa cacaccacca ccccatcttc   14100
tcagagctca aaccctgaca gaacaccagc tccacaggcc ttggcttctg ctgatggtgc   14160
cgtgtattta ccagacttag tggtccaagg ccagagtggc cagatttccc aaagtcaagg   14220
tgtgacagtg ggacagcctc tttgtgtctt tgctgtccta agaaacctgg gccaggccag   14280
gcgcagtggc tcacgcctgt aatcccagca ctttgagaag ccaaggtggg cagatcacga   14340
ggtcaggagt ttgagaccag cctggccaac atggtgaaac cctgtctcta ttaaaaatag   14400
aaaacattag acaggtgtgg tggtgcatgc ctgtaatccc agctactcag gaggctgagg   14460
caggagaatc gcttgaaccc aggaggtgga ggttgcagtg agccgagatt gtgccactgc   14520
actccagcct aggcgacaga gcaagactcc gtctcgggaa aattaattaa taaataaata   14580
aacctaggtc ccagagtccc acagaatggc agacaggagc acctgggggc ttttagggta   14640
tggcatttcc cctgtactaa ctctgggctg tccagagggc catttcatgg cgtggagtgg   14700
agagggaggc agcacaggac ttcctaggcc tcagctctca cctgcccatc ttttgatttc   14760
```

```
caggcagtta acatcactga cctgagcgag aacagaaagc aggacaagcg cttcgccttc   14820
atccgctcag acagtggccc caccaccagt tttgagtctg ccgcctgccc cggttggttc   14880
ctctgcacag cgatggaagc tgaccagccc gtcagcctca ccaatatgcc tgacgaaggc   14940
gtcatggtca ccaaattcta cttccaggag gacgagtagt actgcccagg cctgcctgtt   15000
cccattcttg catggcaagg actgcaggga ctgccagtcc ccctgcccca gggctcccgg   15060 ctatggggc actgaggacc agccattgag gggtggaccc tcagaaggcg tcacaacaac    15120
ctggtcacag gactctgcct cctcttcaac tgaccagcct ccatgctgcc tccagaatgg   15180
tctttctaat gtgtgaatca gagcacagca gcccctgcac aaagcccttc catgtcgcct   15240
ctgcattcag gatcaaaccc cgaccacctg cccaacctgc tctcctcttg ccactgcctc   15300
ttcctccctc attccacctt ccatgcccct ggatccatca ggccacttga tgaccccaa    15360 ccaagtggct cccacaccct gttttacaaa aaagaaaaga ccagtccatg agggaggttt   15420
ttaagggttt gtggaaaatg aaaattagga tttcatgatt ttttttttc agtccccgtg     15480 aaggagagcc cttcatttgg agattatgtt ctttcgggga gaggctgagg acttaaaata   15540
ttcctgcatt tgtgaaatga tggtgaaagt aagtggtagc ttttcccttc tttttcttct    15600 tttttgtga tgtcccaact tgtaaaaatt aaaagttatg gtactatgtt agccccataa     15660 ttttttttt ccttttaaaa cacttccata atctggactc ctctgtccag gcactgctgc     15720
ccagcctcca agctccatct ccactccaga ttttttacag ctgcctgcag tactttacct   15780
cctatcagaa gtttctcagc tcccaaggct ctgagcaaat gtggctcctg ggggttcttt   15840
cttcctctgc tgaaggaata aattgctcct tgacattgta gagcttctgg cacttggaga   15900
cttgtatgaa agatggctgt gcctctgcct gtctccccca ccgggctggg agctctgcag   15960
agcaggaaac atgactcgta tatgtctcag gtccctgcag ggccaagcac ctagcctcgc   16020
tcttggcagg tactcagcga atgaatgcta tatgttggg gtgcaaagtt ccctacttcc    16080
tgtgacttca gctctgtttt acaataaaat cttgaaaatg ccta                   16124

<210> SEQ ID NO 4
<211> LENGTH: 1001
<212> TYPE: DNA
<213> ORGANISM: Artificial sequence
<220> FEATURE:
<223> OTHER INFORMATION: IL1RN rs9005

<400> SEQUENCE: 4
aattaggatt tcatgatttt ttttttcag tccccgtgaa ggagagccct tcatttggag       60
attatgttct tcggggaga ggctgaggac ttaaaatatt cctgcatttg tgaaatgatg      120
gtgaaagtaa gtggtagctt ttccttctt tttcttcttt tttgtgatg tcccaacttg       180 taaaaattaa aagttatggt actatgttag ccccataatt ttttttttcc tttaaaaca      240 cttccataat ctggactcct ctgtccaggc actgctgccc agcctccaag ctccatctcc     300
actccagatt ttttacagct gcctgcagta ctttacctcc tatcagaagt ttctcagctc     360
ccaaggctct gagcaaatgt ggctcctggg ggttctttct tcctctgctg aaggaataaa     420
ttgctccttg acattgtaga gcttctgca cttggagact tgtatgaaag atggctgtgc      480
ctctgcctgt ctcccccacc rggctgggag ctctgcagag caggaaacat gactcgtata    540
tgtctcaggt ccctgcaggg ccaagcacct agcctcgctc ttggcaggta ctcagcgaat    600
gaatgctgta tatgttgggt gcaaagttcc ctacttcctg tgacttcagc tctgttttac   660
```

```
aataaaatct tgaaaatgcc tatattgttg actatgtcct tggccttgac aggctttggg      720
tatagagtgc tgaggaaact gaaagaccaa tgtgtctttc ttaccccaga ggctggcgcc      780
tggcctcttc tctgagagtt cttttcttcc ttcagcctca ctctccctgg ataacatgag      840
agcaaatctc tctgcaaaaa agatatgggg cagcactgtc cacaacagcc tctgctggaa      900
acaacccaag cacccatcac agaatgaatt agtacatcat gtatctgcac acaacacagt      960
gctccttggc aaagaaaatg aatgaattac agccagctgc a                         1001

<210> SEQ ID NO 5
<211> LENGTH: 1001
<212> TYPE: DNA
<213> ORGANISM: Artificial sequence
<220> FEATURE:
<223> OTHER INFORMATION: SNP IL1RN rs315952

<400> SEQUENCE: 5
tcacgaggtc aggagtttga gaccagcctg gccaacatgg tgaaaccctg tctctattaa      60
aaatagaaaa cattagacag gtgtggtggt gcatgcctgt aatcccagct actcaggagg     120
ctgaggcagg agaatcgctt gaacccagga ggtggaggtt gcagtgagcc gagattgtgc     180
cactgcactc cagcctaggc gacagagcaa gactccgtct cgggaaaatt aattaataaa     240
taaataaacc taggtcccag agtcccacag aatggcagac aggagcacct gggggctttt     300
agggtatggc atttcccctg tactaactct gggctgtcca gagggccatt tcatggcgtg     360
gagtggagag ggaggcagca caggacttcc taggcctcag ctctcacctg cccatctttt     420
gatttccagg cagttaacat cactgacctg agcgagaaca gaaagcagga caagcgcttc     480
gccttcatcc gctcagacag yggccccacc accagttttg agtctgccgc ctgccccggt     540
tggttcctct gcacagcgat ggaagctgac cagcccgtca gcctcaccaa tatgcctgac     600
gaaggcgtca tggtcaccaa attctacttc caggaggacg agtagtactg cccaggcctg     660
cctgttccca ttcttgcatg gcaaggactg cagggactgc cagtccccct gccccagggc     720
tcccggctat gggggcactg aggaccagcc attgagggggt ggaccctcag aaggcgtcac   780
aacaacctgg tcacaggact ctgcctcctc ttcaactgac cagcctccat gctgcctcca     840
gaatggtctt tctaatgtgt gaatcagagc acagcagccc ctgcacaaag cccttccatg     900
tcgcctctgc attcaggatc aaaccccgac cacctgccca acctgctctc ctcttgccac     960
tgcctcttcc tccctcattc caccttccca tgccctggat c                        1001

<210> SEQ ID NO 6
<211> LENGTH: 52
<212> TYPE: DNA
<213> ORGANISM: artificial sequence
<220> FEATURE:
<223> OTHER INFORMATION: Specific locus- IL1RN rs9005
<220> FEATURE:
<221> NAME/KEY: variation
<222> LOCATION: (27)..(27)
<223> OTHER INFORMATION: n is a or g

<400> SEQUENCE: 6
ctgtgcctct gcctgtctcc cccaccnggc tgggagctct gcagagcagg aa              52

<210> SEQ ID NO 7
<211> LENGTH: 52
<212> TYPE: DNA
<213> ORGANISM: Artificial Sequence
<220> FEATURE:
<223> OTHER INFORMATION: Specific locus - IL1RN rs315952
```

```
<220> FEATURE:
<221> NAME/KEY: variation
<222> LOCATION: (27)..(27)
<223> OTHER INFORMATION: n is c or t

<400> SEQUENCE: 7
cgcttcgcct tcatccgctc agacagnggc cccaccacca gttttgagtc tg            52

<210> SEQ ID NO 8
<211> LENGTH: 25
<212> TYPE: DNA
<213> ORGANISM: Artificial sequence
<220> FEATURE:
<223> OTHER INFORMATION: rs315952 primer 1

<400> SEQUENCE: 8
gcttcgcctt catccgctca gacag                                         25

<210> SEQ ID NO 9
<211> LENGTH: 25
<212> TYPE: DNA
<213> ORGANISM: Artificial sequence
<220> FEATURE:
<223> OTHER INFORMATION: rs315952 primer 2

<400> SEQUENCE: 9
ggccccacca ccagttttga gtctg                                         25

<210> SEQ ID NO 10
<211> LENGTH: 25
<212> TYPE: DNA
<213> ORGANISM: Artificial Sequence
<220> FEATURE:
<223> OTHER INFORMATION: rs9005 primer 1

<400> SEQUENCE: 10
tgtgcctctg cctgtctccc ccacc                                         25

<210> SEQ ID NO 11
<211> LENGTH: 25
<212> TYPE: DNA
<213> ORGANISM: Artificial Sequence
<220> FEATURE:
<223> OTHER INFORMATION: rs9005 primer 2

<400> SEQUENCE: 11
ggctgggagc tctgcagagc aggaa                                         25
```

GENETIC MARKERS FOR PREDICTING RESPONSIVENESS TO FPG-18 COMPOUND

CROSS-REFERENCE TO RELATED APPLICATIONS

This application is the U.S. national stage application of International Patent Application No. PCT/EP2013/066421, filed Aug. 5, 2013, which claims the benefit of U.S. Provisional Patent Application Nos. 61/680,480, filed Aug. 7, 2012 and 61/778,912, filed Mar. 13, 2013.

The Sequence Listing for this application is labeled "Seq-List.txt" which was created on Jan. 30, 2015 and is 28 KB. The entire contents of the sequence listing is incorporated herein by reference in its entirety.

FIELD OF INVENTION

The present invention relates, generally, to pharmacogenetics, and more specifically to genetic markers associated with the clinical response to an FGF-18 compound during treatment of a cartilage disorder. The present invention more particularly relates to human genes, which can be used for the diagnosis and treatment of cartilage disorders. The invention further discloses specific polymorphisms or alleles of the IL1RN gene that are related to cartilage response to an FGF-18 compound treatment as well as diagnostic tools and kits based on these susceptibility alterations. Thus, the invention can be used in predicting the response to an FGF-18 compound treatment. It could be used for selecting/identifying patients to be treated by intra-articular administration of an FGF-18 compound. The use of these markers in diagnostics could result in increased benefit and reduced risk for patients.

BACKGROUND OF THE INVENTION

Cartilage disorders broadly refer to diseases characterized by degeneration of metabolic abnormalities in the connective tissues which are manifested by pain, stiffness and limitation of motion of the affected body parts. These disorders can be due to pathology or can be the result of trauma or injury. Among others, cartilage disorders include osteoarthritis (OA) and cartilage injury (including sports injuries of cartilage and joints, and surgical injuries such as microfracture(s)). Mature cartilage has limited ability to repair itself, notably because mature chondrocytes have little potential for proliferation and due to the absence of blood vessels. In addition, cartilage is not well nutrified and has a low oxygen pressure. Replacement of damaged cartilage, in particular articular cartilage, caused either by injury or disease is a major challenge for physicians, and available surgical treatment procedures are considered not completely predictable and effective for only a limited time. Therefore, the majority of younger patients either do not seek treatment or are counseled to postpone treatment for as long as possible. When treatment is required, the standard procedure is age-dependent and varies between total joint replacement, transplantation of pieces of cartilage or marrow stimulating technique (such as microfracture). Microfracture is a common procedure that involves penetration of the subchondral bone to stimulate cartilage deposition by bone marrow-derived stem cells. However, it has been shown that this technique does not sufficiently repair the chondral defect and the new cartilage formed is mainly fibrocartilage, resulting in inadequate or altered function and biomechanics. Indeed, fibrocartilage does not have the same durability and may not adhere correctly to the surrounding hyaline cartilage. For this reason, the newly synthesized fibrocartilage may break down more easily (expected time frame: 5-10 years).

For patients with osteoarthritis, non-surgical treatment consists notably of physical therapy, lifestyle modification (e.g., reducing activity), supportive devices, oral and injected drugs (e.g., non-steroidal anti-inflammatory drugs), and medical management. Once these treatments fail, surgery, such as joint replacement, is the main option for the patients. Such an option can provide a reduction in symptoms that is generally only short lived. Tibial or femoral osteotomies (cutting the bone to rebalance joint wear) may reduce symptoms, help to maintain an active lifestyle, and delay the need for total joint replacement. Total joint replacement can provide relief for the symptom of advanced osteoarthritis, but generally requires a change in a patient's lifestyle and/or activity level.

At that time, drug treatments on the market are mainly directed to pain relief. There is not yet a commercially available treatment that restores cartilage damage (see Lotz, 2010).

Fibroblast Growth factor 18 (FGF-18) is a member of the FGF family of proteins, closely related to FGF-8 and FGF-17. It has been shown that FGF-18 is a proliferative agent for chondrocytes and osteoblasts (Ellsworth et al., 2002; Shimoaka et al., 2002). FGF-18 has been proposed for the treatment of cartilage disorders such as osteoarthritis and cartilage injury, either alone (WO2008/023063) or in combination with hyaluronic acid (WO2004/032849).

Sprifermin, which is a truncated form of human FGF-18, is being investigated in clinical trials for treatment of both osteoarthritis and cartilage injury (for more details see for instance NCT01033994, NCT00911469 and NCT01066871). The current dosing regimen for sprifermin is once weekly for 3 weeks (one treatment cycle), the drug being administered via intra-articular injections. This treatment cycle can be repeated. This dosing regimen has been described in WO2008023063.

At that time, OA and cartilage injury treatments with FGF-18, during clinical trials, are provided to patients without predictive information on the response, i.e., without knowledge on whether the treatment will likely be highly effective, moderately effective or show only little or no effect. Currently, numerous treated patient populations exhibit an intermediate/high response to treatment according to the WOMAC scores with sprifermin after at least one treatment cycle, however, others either do not respond to said treatment or respond while presenting high WOMAC scores compared to control.

Here we describe for the first time genetic markers that are associated with the quality of the clinical response to treatment of cartilage disorders such as OA, cartilage injury or microfracture(s) with FGF-18. Such markers are useful for identifying, through genetic screening prior to the treatment, subgroups of patients that are more likely to exhibit a particular response to treatment with FGF-18, such as a very good clinical response to treatment with FGF-18, or on the contrary those for whom the therapy may fail. Knowledge of the type of clinical response of a patient to treatment can be used to optimize therapy or select therapy, such as selecting treatment with FGF-18 as a first line therapy or adapting the dosing regimen. Such information will be clinically useful for the medical management of cartilage disorders, such as OA/cartilage injury, in patients. For example, if an individual with OA or cartilage injury is known to be at increased risk for not responding to the FGF-18 treatment, the physician may exclude said patient from the FGF-18 treatment. In addition, such predictive information may also be clinically useful to guide decisions on the dosing regimen.

SUMMARY OF THE INVENTION

The present invention is directed to a method of predicting the sensitivity to treatment with an FGF-18 compound of a subject having a cartilage disorder, the method comprising the steps of:
a. Determining, from a nucleic acid sample, the genotype at both loci IL-1RN rs9005 and IL-1RN rs315952; and
b. Predicting from the result of step a high, intermediate, low or no sensitivity of said subject to treatment with an FGF-18 compound.

According to said method, the presence of the genotype G/G at IL-1RN rs9005 and T/T at IL-1RN rs315952 is predictive of no response or low response (i.e., non-sensitivity) to treatment with an FGF-18 compound. On the contrary, the presence of the genotype A/G or A/A at IL-1RN rs9005 and T/C or C/C at IL-1RN rs315952 is predictive of high response (high sensitivity) to treatment with an FGF-18 compound. The other genotypes at these loci are predictive of intermediate sensitivity (i.e., G/G at IL-1RN rs9005 and T/C or C/C at IL-1RN rs315952 or A/G or A/A at IL-1RN rs9005 and T/T at IL-1RN 315952, or C/C in the complement of IL-1RN rs9005 and A/G or G/G in the complement of IL-1RN rs315952 or T/C or T/T in the complement of IL-1RN rs9005 and A/A in the complement of IL-1RN 315952).

Also described herein is a method for selecting patients having a cartilage disorder for inclusion in or exclusion from treatment, or clinical trials, with an FGF-18 compound, based on the likelihood of their sensitivity to said treatment, comprising determining, from a nucleic acid sample, the genotype at both loci IL-1RN rs9005 and IL-1RN rs315952, wherein the patient's genotype with respect to said loci is predictive of the patient's risk for being sensitive or non-sensitive to said treatment, and selecting sensitive patients as being suitable for said treatment. In particular, patients having the genotype G/G at IL-1RN rs9005 and T/T at IL-1RN rs315952 will be classified as non-sensitives. As such, these subjects could be excluded from the FGF-18 compound treatment, or from clinical trials. It follows that the subjects having any other genotypes at these loci (i.e., G/G at IL-1RN rs9005 and T/C or C/C at IL-1RN rs315952 or A/G or A/A at IL-1RN rs9005 and T/T, T/C or C/C at IL-1RN rs315952) will be classified as sensitives, comprising both intermediate-sensitive and super-sensitive (or high-sensitive) subjects, and thus could be included in (or suitable for) treatment with an FGF-18 compound, or clinical trials.

The present invention further provides a method for selecting patients having a cartilage disorder for an alternative therapeutic regimen with an FGF-18 compound, based on their likelihood of being super-sensitives to FGF-18 compound treatment, comprising determining, from a nucleic acid sample, the genotype at both loci IL-1RN rs9005 and IL-1RN rs315952, wherein the patient's genotype with respect to said loci is predictive of the subject's risk for being super-sensitive to a treatment with said FGF-18 compound and selecting said patient for an alternative therapeutic regimen that would be suitable for said patient. Preferably, in such alternative therapeutic regimen, the total dose of FGF-18 compound that is to be administered could be reduced compared to the dose of FGF-18 compound to be administered to a patient who does not present a risk for being super-sensitive to the FGF-18 compound treatment. In particular, patients having the genotype A/G or A/A at IL-1RN rs9005 together with T/C or C/C at IL-1RN rs315952, being classified as super-sensitives, are selected for an alternative therapeutic regimen in which the dose of FGF-18 to be administered is reduced.

Also provided is a method for selecting patients having a cartilage disorder for an alternative therapeutic regimen with an FGF-18 compound, based on their likelihood of AIR events when treated with an FGF-18 compound, comprising determining, from a nucleic acid sample, the genotype at both loci IL-1RN rs9005 and IL-1RN rs315952, wherein the patient's genotype with respect to said loci is predictive of the subject's risk for developing AIR events in response to treatment with said FGF-18 compound and selecting said patient for an alternative therapeutic regimen that would be suitable for said patient. Preferably, in such alternative therapeutic regimen, the total dose of FGF-18 compound that is to be administered could be reduced compared to the dose of FGF-18 compound to be administered to a patient who does not present a risk for developing AIR events. In particular, patients having the genotype A/G or A/A at IL-1RN rs9005 together with T/C or C/C at IL-1RN rs315952, being classified as at risk for developing AIR events, are selected for an alternative therapeutic regimen in which the dose of FGF-18 to be administered is reduced.

Also encompassed is an FGF-18 compound for use in the treatment of a patient having a cartilage disorder, characterized in that the patient has any combination of the genotype(s) selected from the group consisting of: 1) G/G at IL-1RN rs9005 and T/C or C/C at IL-1RN rs315952, and 2) A/G or A/A at IL-1RN rs9005 and T/T, T/C or C/C at IL-1RN rs315952. Should the patient be classified as super-sensitive, i.e., a subject having the genotypes A/G or A/A at IL-1RN rs9005 together with T/C or C/C at IL-1RN rs315952, said patient could be treated with a reduced dose of FGF-18 compound compared to a subject having one of the two other combinations of genotypes.

In a further aspect, it also describes a kit comprising means for performing the above methods and instructions for use. Said kit includes at least a couple of specific primers or probes for detecting the presence or absence of the alleles.

In particular embodiments of the present invention as a whole, i.e., in any of the methods or uses mentioned herein, the FGF-18 compound to be used as a treatment is sprifermin and the patient has a cartilage disorder selected from the group consisting of osteoarthritis, cartilage injury, fractures affecting joint cartilage, and surgical procedures with impact on joint cartilage (e.g., microfracture).

It is to be understood that in any of the methods or uses mentioned herein, before determining the genotype at one locus, it is necessary to obtain a nucleic acid sample (or a test sample) of said subject, via for instance blood or saliva collection. Alternatively the test sample is selected from buccal cells, urine or stool. Preferably, the nucleic acid sample is a DNA sample. Further, it is also to be understood that any of the methods or uses mentioned herein are performed in vitro, and not on the animal or human body.

It is also to be understand that in the context of the invention as a whole, determination can be performed in the complementary sequence corresponding to IL rs9005 and ILrs315952.

Definitions

The term "FGF-18 compound" or "FGF-18", as used herein, is intended to be a protein maintaining at least one biological activity of the human FGF-18 protein. FGF-18 may be native, in its mature form, or a truncated form thereof. Biological activities of the human FGF-18 protein include notably the increase in osteoblastic activity (see WO98/16644) or in cartilage formation (see WO2008/023063). Native, or wild-type, human FGF-18 is a protein expressed by chondrocytes of articular cartilage. Human FGF-18 was first designated zFGF-5 and is fully described in WO98/16644. SEQ ID NO:1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207 (Ala) of SEQ ID NO: 1 (180 amino acids). The term also includes fusion protein, wherein FGF-18 protein is coupled with a heterologous protein or a chemical compound.

FGF-18, in the present invention, may be produced by recombinant methods, such as taught by WO2006/063362. Depending on the expression systems and conditions, FGF-18 in the present invention is expressed in a recombinant host cell with a starting methionine (Met) residue or with a signal sequence for secretion. When expressed in prokaryotic host, such as in E. coli, FGF-18 contains an additional Met residue in the N-terminal of its sequence. For instance, the amino acid sequence of human FGF-18, when expressed in E. coli, starts with a Met residue in N-term (position 1) followed by residues 28 (Glu) to residue 207 (Ala) of SEQ ID NO: 1.

The term "truncated form" of FGF-18, as used herein, refers to a protein which comprises or consists of residues 28 (Glu) to 196 (Lys) of SEQ ID NO: 1. Preferably, the truncated form of the FGF-18 protein is the polypeptide designated "trFGF-18" (170 amino acids), which starts with a Met residue (in N-terminal) followed by amino acid residues 28 (Glu) to 196 (Lys) of the wild-type human FGF-18. The amino acid sequence of trFGF-18 is shown in SEQ ID NO:2 (amino acid residues 2 to 170 of SEQ ID NO:2 correspond to amino acid residues 28 to 196 of SEQ ID NO:1). trFGF-18 is a recombinant truncated form of human FGF-18, produced in E. coli (see WO2006/063362). The International Nonproprietary Name (INN) for this particular form of FGF-18 is sprifermin. Sprifermin has been shown to display similar activities as the mature human FGF-18, e.g., it increases chondrocyte proliferation and cartilage deposition, leading to repair and reconstruction of a variety of cartilaginous tissues (see WO2008/023063).

The term "cartilage disorder", as used herein, encompasses disorders resulting from damages due to injury, such as traumatic injury, chondropathy or arthritis. Examples of cartilage disorders that may be treated by the administration of the FGF-18 formulation described herein include but are not restricted to arthritis, such as osteoarthritis, cartilage injury, fractures affecting joint cartilage and surgical procedures with impact on joint cartilage (e.g., microfracture). Degenerative diseases/disorders of the cartilage or of the joint, such as chondrocalcinosis, polychondritis, relapsing polychondritis, ankylosing spondylitis or costochondritis, are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of the cartilage layer), and grade 4: the cartilage tear exposes the underlying (subchronal) bone (see for instance page 13 of Worldwide Website:cartilage.org/_files/content-management/ICRS_evaluation.pdf).

The term "osteoarthritis" is used to intend the most common form of arthritis. The term "osteoarthritis" encompasses both primary osteoarthritis and secondary osteoarthritis (see for instance The Merck Manual, 17$^{th}$ edition, page 449). The most common way of classifying/grading osteoarthritis is the use of the Kellgren-Lawrence radiographic grading scale (see table below). Osteoarthritis may be caused by the breakdown of cartilage. Bits of cartilage may break off and cause pain and swelling in the joint between bones. Over time, the cartilage may wear away entirely, and the bones will rub together. Osteoarthritis can affect any joint but usually concerns hands and weight-bearing joints such as hips, knees, feet, and spine. In a preferred example, the osteoarthritis may be knee osteoarthritis or hip osteoarthritis. Osteoarthritis is one of the preferred cartilage disorders that can be treated by administering the FGF-18 compounds according to the present invention.

The Kellgren-Lawrence Radiographic Grading Scale of Osteoarthritis is described as follows:

| Grade of Osteoarthritis | Description |
|---|---|
| 0-None | No radiographic findings of osteoarthritis |
| 1-Doubtful | Doubtful narrowing of joint space and possible osteophytic lipping |
| 2-Minimal | Definite osteophytes, definite narrowing of joint space |
| 3-Moderate | Moderate multiple osteophytes, definite narrowing of joints space, some sclerosis and possible deformity of bone contour |
| 4-Severe | Large osteophytes, marked narrowing of joint space, severe sclerosis and definite deformity of bone contour |

The term "cartilage injury" as used herein is a cartilage disorder or cartilage damage resulting notably from a trauma. Cartilage injuries can occur notably after traumatic mechanical destruction, notably further to an accident or surgery (for instance microfracture surgery). The term "cartilage injury" also includes chondral or osteochondral fracture, damage to meniscus, and microfracture. Also considered within this definition is sport-related injury or sport-related wear of tissues of the joint.

The term AIR (acute inflammatory reaction) as used herein is defined as follows. Within a 1 to 7-day period, preferably within a 3-day period, following the intra-articular injection of an FGF-18 compound in the target knee, both the following criteria must be fulfilled:
Self-reported swelling (synovial fluid effusion)
Pain increase by 30 mm on 100 mm Visual Analogue Scale (VAS)

An "allele" is a particular form of a gene, genetic marker or other genetic locus that is distinguishable from other forms of the gene, genetic marker or other genetic locus, e.g., without limitation by its particular nucleotide sequence. The term allele also includes for example without limitation one form of a single nucleotide polymorphism (SNP). An individual can be homozygous for a certain allele in diploid cells; i.e., the allele on both paired chromosomes is identical, or heterozygous for said allele, i.e., the alleles on both paired chromosomes are not identical.

The term "genetic marker", "biomarker" or "marker" refers to an identifiable polymorphic (genetic) locus. An example without limitation of a genetic marker is a single nucleotide polymorphism (SNP).

A "single nucleotide polymorphism (SNP)" is a DNA sequence variation occurring when a single nucleotide—A (for Adenine), T (for Thymine), C (for Cytosine), or G (for Guanine)—in the genome (or other sequence shared between individuals of a species) differs between individuals of a species (or between paired chromosomes in an individual). An SNP is frequently preceded by and followed by highly conserved sequences in the population of interest and thus the location of an SNP is typically made in reference to a consensus nucleic acid sequence of thirty to sixty nucleotides that bracket the genetic marker locus, which is sometimes referred to as a context sequence for the SNP. The SNPs that were analyzed by the present inventors in connection with treatment of cartilage disorders with sprifermin are those shown in Table 1.

A "genotype" as used herein refers to the combination of both alleles of a genetic marker, e.g., without limitation of an SNP, on a single genetic locus on paired (homologous) chromosomes in an individual. "Genotype" as used herein also refers to the combination of alleles of more than one genetic loci, e.g., without limitation of SNPs, on a pair or more than one pair of homologous chromosomes in an individual.

The term "haplotype" refers to variants or alleles from distinct markers (e.g., SNPs) that are co-located on the same chromosome. SNP genotype data, as measured from SNP arrays or Taqman assays, are unphased (i.e., the chromosome's parent of origin is unknown for each allele). Computational methods (Browning and Browning, 2011) use information across individuals to estimate (i.e., infer) haplotype phase from genotype data.

The term "Genotyping" refers to a process for determining a genotype of an individual, either for a single SNP or many SNPs.

"Locus" or "genetic locus" refers to a specific location on a chromosome or other genetic material. For instance, IL-1RN rs9005 is a locus and can be called, in the frame of the present invention, either "IL-1RN rs9005" or "locus IL-1RN rs9005". The same applies to IL-1RN rs315952. As is self-evident for the skilled person, from the NCBI database for these SNPs, the genotype to be determined at both IL-1RN rs9005 and IL-1RN rs315952 is the one in position 27 of each of these loci, i.e., position 27 of SEQ ID NO:6 and position 27 of SEQ ID NO:7.

The term "SNP1" in the context of the present invention is position 27 of SEQ ID NO: 6, also identified as rs9005 in the NCBI database. SEQ ID NO. 6 is a portion of the genomic nucleic acid sequence of interleukin 1 receptor antagonist (IL-1RN). The terms "IL-1RN rs9005", "rs9005" and "SNP1" are used interchangeably.

The term "SNP2" refers to position 27 of SEQ ID NO: 7 identified as being rs315952 in the NCBI database. SEQ ID NO: 7 is a portion of the genomic nucleic acid sequence of IL-1RN. The terms "IL-1RN rs315952", "rs315952" and "SNP2" are used interchangeably.

The term "probe" or "primer" refers to an oligonucleotide, i.e., a nucleic acid or a nucleic acid derivative, including without limitation a locked nucleic acid (LNA), peptide nucleic acid (PNA) or bridged nucleic acid (BNA), that is usually between 5 and 100 contiguous bases in length, and most frequently between 5-40, 5-35, 5-30, 5-25, 5-20, 5-15, 5-10, 10-50, 10-40, 10-30, 10-25, 10-20, 15-50, 15-40, 15-30, 15-25, 15-20, 20-50, 20-40, 20-30 or 20-25 contiguous bases in length. The sequence of a probe/primer can be designed to specifically hybridize to one of the allelic forms of a genetic marker; such oligonucleotides are referred to as allele-specific probes. If the genetic marker is an SNP, the complementary allele for that SNP can occur at any position within an allele-specific probe. Other probes/primers useful in practicing the invention specifically hybridize to a target region adjacent to an SNP with their 3' terminus located one to less than or equal to about 10 nucleotides from the genetic marker locus, preferably about 5 nucleotides. Such probes/primers hybridizing adjacent to an SNP are useful in polymerase-mediated primer extension methods and are referred to herein as "primer-extension oligonucleotides." In a preferred embodiment, the 3'-terminus of a primer-extension oligonucleotide is a deoxynucleotide complementary to the nucleotide located immediately adjacent an SNP.

The term "polymorphism" refers to two or more alternate forms (alleles) in a population of a genetic locus that differ in nucleotide sequence or have variable numbers of repeated nucleotide units. Polymorphisms occur in coding regions (exons), non-coding regions of genes or outside of genes (intergenic regions). The different alleles of a polymorphism typically occur in a population at different frequencies, with the allele occurring most frequently in a selected population sometimes referenced as the "major" or "wild-type" allele. Diploid organisms may be homozygous or heterozygous for the different alleles that exist. A biallelic polymorphism has two alleles.

The term "epistasis" is generally used to define the interaction between genes. Epistasis was first defined by Bateson (Bateson and Mendel, 1909) to describe a masking effect whereby a variant or allele at one locus prevents the variant at another locus from manifesting its effect. However, the scientific literature provides many different definitions (Phillips, 1998; Cordell, 2002). Herein, epistasis was tested as the statistical interaction between genotypes from two distinct SNPs. This is similar to the definition proposed by Fisher in 1918 (Fisher, 1918), i.e., a deviation from additivity in the effect of alleles at different loci with respect to their contribution to a phenotype.

"WOMAC total scores" or "WOMAC scores" ("WOMAC" for "Western Ontario and McMaster Universities Osteoarthritis Index") measure pain (WOMAC pain score), function (WOMAC function score) and stiffness (WOMAC stiffness score). When applied to assessment of pain and dysfunction associated with cartilage injury, it consists of a questionnaire containing 24 items divided into 3 subscales (5 items for Pain, 2 items for Stiffness and 17 items for Physical Function) (see Bellamy et al., 1988; Wolfe, 1999). It is a well-known instrument, widely used notably in the assessment of OA severity.

In order to evaluate cartilage repair, cartilage volume measurements were performed through magnetic resonance imaging (MRI) measurements, including Total volume of cartilage (also referred as LFTC (lateral femoro-tibial compartment)+MFTC (medial femoro-tibial compartment)), Lateral volume of cartilage (also referred as LFTC), Medial volume of cartilage (also referred as MFTC), and new total average cartilage thickness.

The term "baseline" means before treatment (i.e., at study entry). It refers notably to clinical variables, such as, but not limited to, the cartilage volume and WOMAC total score of a given patient at study entry (i.e., before treatment with FGF-18 compound or placebo).

"Sensitives" are patients that exhibit a response to treatment of a cartilage disorder with an FGF-18 compound. Preferably, sensitive patients (or patients showing sensitivity to treatment) exhibit a notably higher increase in total cartilage volume than placebo-treated subjects, i.e., they show cartilage repair. In addition, sensitive patients exhibit at least similar improvement in WOMAC total scores than placebos. The terms "super-sensitives", "intermediate-sensitives" and "non-sensitives" refer to the different groups of patients depending notably on the increase of the cartilage volume following FGF-18 compound treatment. Super-sensitives display a high response (i.e., high cartilage repair) to treatment with an FGF-18 compound, intermediate-sensitives display a good or intermediate response (i.e., good or intermediate cartilage repair) to treatment with an FGF-18 compound, and non-sensitives display no or low response to treatment with an FGF-18 compound. Both super-sensitive and sensitive subjects have similar improvement in WOMAC total scores than placebos. Conversely, non-responders have significantly smaller improvement in WOMAC total score than placebos. The terms "super-sensitives" and "high-sensitives" are used interchangeably. It is noted that super-sensitives have been shown to present higher risk of AIR events.

More particularly, the terms "intermediate-sensitives", "super-sensitives", and "non-sensitives" include, but are not limited to, the different groups of patients depending on the increase of the cartilage volume and improvement of WOMAC total scores following FGF-18 compound treatment.

The proposed criteria for sensitives are the following:
1. Positive cartilage increase (between +10 and +100 $mm^3$) compared to baseline,
2. Cartilage increase change significantly higher than change in placebo (e.g., as tested with a linear model adjusting for BMI, KL grade, sex and age and with alpha=5%),
3. WOMAC score improvement, i.e, diminution (e.g., more than 5 points reduction) compared to baseline, and
4. WOMAC score change not significantly higher than change in placebo (e.g., as tested with a linear model adjusting for BMI, KL grade, sex and age and with alpha=5%).

The proposed criteria for super-sensitives are the same as for sensitives, but with cartilage increase greater than 100 $mm^3$ (criterion #1) compared to baseline. Non-sensitives can be defined as subjects not fulfilling criteria #1 or #2 and not fulfilling criteria #3 or #4.

Thus, intermediate sensitives display a good or intermediate response (or a good or intermediate sensitivity) to treatment with an FGF-18 compound (see above criteria; according to the examples, median change: +84.81 $mm^3$ total cartilage volume increase compared to baseline; median change: −20 points on the WOMAC total score compared to baseline; and non-significant difference in WOMAC total score compared to placebos). Super-sensitives display a high response (or a high sensitivity) to treatment with an FGF-18 compound (see above criteria; according to the examples, median change: +119.46 $mm^3$ total cartilage volume increases compared to baseline, representing a +40.85% increase (i.e., benefit) compared to sensitive subjects; median change: −10 points on the WOMAC total score compared to baseline; and non-significant difference in WOMAC total score compared to placebos). Non-sensitives display no or low response (or no or low sensitivity) to treatment with an FGF-18 compound (see above criteria; according to the examples: significantly smaller increase in total cartilage volume compared to placebos (difference between medians: −106.64 $mm^3$); little improvement (median change: −1 point) in WOMAC total scores compared to baseline; and significant difference in WOMAC total score compared to placebos).

The "response" or "sensitivity" to an FGF-18 compound treatment is to be understood as 1 year after the first injection and measured as 1) increase of cartilage volume, measured owing to MRI or X-Ray for instance, 2) decrease of WOMAC total scores, and 3) changes in WOMAC total scores not significantly higher than those of placebos (refer also to the definition of "sensitive").

A "prognostic biomarker" is informative about the subject's condition, including and not limited to disease evolution, disease severity or disease outcome, regardless of any therapy. A "predictive biomarker" is informative about the effect of a received therapy, including and not limited to efficacy and safety outcome. The prognostic and predictive definitions are not mutually exclusive, thus a biomarker can be both prognostic and predictive.

As used in the present invention, the term "MAD" means Multiple Ascending Dose. When this acronym is followed by a figure, the figure corresponds to the dose at which an FGF-18 compound has been injected during treatment. For instance MAD100 refers to a treatment during which a patient received 100 mcg of an FGF-18 compound per injection. The abbreviation "PL" (and "MADPL") refers to placebo.

The term "storage device", as used herein, is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, Extranet, and local and distributed computer processing systems. Storage devices also include, but are not limited to, magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media.

As used herein, the term "stored" refers to a process for encoding information on the storage device. Those skilled in the art can readily adopt any of the presently known methods for recording information on known media to generate manufactures comprising expression level information.

DETAILED DESCRIPTION OF THE INVENTION

There is a need to predict the clinical efficacy (notably with regards to cartilage repair) of an FGF-18 compound treatment for the treatment of patients having a cartilage disorder, such as osteoarthritis, cartilage injury, fractures affecting joint cartilage or surgical procedures with impact on joint cartilage (e.g., microfracture). To optimize the treatment of said patients, it is important to identify biomarkers that could be used as predictors of the response of a given patient to the FGF-18 compound treatment, notably with regard to cartilage repair. Such predictive biomarkers may be used to identify high-risk groups of either non-sensitives or on the contrary super-sensitives to the treatment. For instance, if one patient having osteoarthritis is known to be at high risk for non-responding (or for being non-sensitive) to the treatment, the physician may decide not to propose an FGF-18 compound, such as sprifermin, to said patient. On the contrary, if one patient having osteoarthritis is known to be at high risk for being super-sensitive to the treatment, the physician may decide to adapt the dose regimen, in order to lower the dose of FGF-18 to be administered to said patient. Such predictive information may be clinically useful to guide medical decisions, notably on the timing of joint replacement surgery when needed.

The surprising finding of the present invention is based on a study aimed at identifying potential biomarkers associated with sprifermin administration. The biomarkers used in this study were composed of both candidate genetic markers (see Table 1) and less than 1 million SNPs covering the human genome with a median marker spacing of 680 bases. The association between genetic markers and clinical response variables was assessed. The rationale behind this type of analysis was to identify biomarkers that could be predictive of the clinical outcome (notably with regard to cartilage repair) for a patient to be treated with an FGF-18 compound such as sprifermin. These SNPs could be used to stratify and target specific patient populations.

The inventors have surprisingly found an association with certain biomarkers (or SNPs) and outcome (e.g., cartilage repair) as well as adverse effects of the FGF-18 therapy. Of special interest are the SNPs rs9005 and rs315952, both located in the IL-1RN gene (see FIG. 1).

These biomarkers have been described in the literature as being possibly related to disease severity and progression in OA patients (see for instance WO2009/135218 or Attur et al., 2010), using a haplotype (the so-called C-T-A haplotype) that includes rs419598 (C), rs315952 (T) and rs9005 (A). Interestingly, although two of these biomarkers, i.e., rs9005 and rs315952, are strongly correlated with responsiveness to FGF-18 treatment, as shown in the present invention, the third one, i.e., rs419598, does not appear being further involved in the observed phenotype, although described, in the literature, as being linked to the two other SNPs. Indeed, the so-called C-T-A haplotype did not allow stratifying subjects for change in total cartilage volume (FIG. 2) nor change in WOMAC total score (FIG. 3). Thus the C-T-A haplotype was not identified as a good predictor of the response to FGF-18 therapy.

On the contrary, it has been surprisingly found by the present inventors that the alleles A of the biomarker rs9005 together with C of the biomarker rs315952 are associated with a better response to treatment with an FGF-18 compound, such as sprifermin, in subjects afflicted with cartilage injury (Table 4). These subjects are called super-sensitives or high-sensitives.

On the contrary, it has also surprisingly been found by the present inventors that the genotype rs315952 T/T together with rs9005 G/G is associated with an absence of, or low, response to treatment with an FGF-18 compound (i.e., non-sensitivity to treatment with an FGF-18 compound), such as sprifermin, in subjects afflicted with cartilage disorder (Table 4). These subjects are called non-sensitives. It follows that patients having any other genotype at both loci (i.e., G/G at IL-1RN rs9005 and T/C or C/C at IL-1RN rs315952 or A/G or A/A at IL-1RN rs9005 and T/T at IL-1RN 315952) are intermediate sensitives.

Therefore, it is a finding of the present invention that polymorphic loci IL-1RN rs9005 and IL-1RN rs315952 can be used in combination as predictive biomarkers of responsiveness of one subject to FGF-18 compound treatment, such as sprifermin (Table 4). Preferably, the subject has a cartilage disorder, such as osteoarthritis, cartilage injury, fractures affecting joint cartilage or surgical procedures with impact on joint cartilage (e.g., microfracture). In a particular embodiment, the subject will be predicted to be non-sensitive to FGF-18 compound treatment if he has the genotype IL-1RN rs9005 G/G together with IL-1RN rs315952 T/T. On the contrary, the subject will be predicted to be a super-sensitive (or a high-sensitive) to FGF-18 compound treatment if he has the genotype IL-1RN rs9005 A/G or A/A together with IL-1RN rs315952 T/C or C/C. In any other case, the patient will be predicted to be intermediate sensitive to FGF-18 compound treatment (see Table 22 for summary of clinical outcomes and potential therapeutic options).

The present invention is therefore directed to a method of predicting the sensitivity to treatment with an FGF-18 compound of a subject having a cartilage disorder, the method comprising the steps of:
 a. Determining the genotype at both IL-1RN rs9005 and IL-1RN rs315952; and
 b. Predicting from the result of step a high, intermediate, low or no sensitivity of said subject to treatment with an FGF-18 compound.

Before determining the genotype at one locus, it is necessary to obtain a nucleic acid sample of said subject, for instance by blood or saliva collection. Preferably, the nucleic acid sample is a DNA sample. Thus, the present invention is directed to a method of predicting the sensibility to treatment with an FGF-18 compound in a subject having a cartilage disorder, the method comprising the steps of:
 a. Obtaining a nucleic acid sample of said subject;
 b. Determining, from said nucleic acid sample, the genotype at both IL-1RN rs9005 and IL-1RN rs315952; and
 c. Predicting from the result of step b the probability of a high, intermediate or low or no sensitivity to treatment with an FGF-18 compound.

According to said method, the presence of the genotype G/G at IL-1RN rs9005 and T/T at IL-1RN rs315952 is predictive of absence of, or low, response to treatment with an FGF-18 compound. The patient will thus be predicted to be non-sensitive. On the contrary, the presence of the genotype A/G or A/A at IL-1RN rs9005 and T/C or C/C at IL-1RN rs315952 is predictive of high response to treatment with an FGF-18 compound. The patient will thus be predicted to be super-sensitive. It follows that the subjects having any other genotypes at these loci (i.e., G/G at IL-1RN rs9005 and T/C or C/C at IL-1RN rs315952 or A/G or A/A at IL-1RN rs9005 and T/T at IL-1RN 315952) will be classified as having intermediate sensitivity to treatment with an FGF-18 compound. From said prediction, the doctor can easily select only those patients that are predicted to be sensitives to FGF-18 compound treatment, including both intermediate-sensitives and super-sensitives.

The present invention also relates to an assay to determine sensitivity to an FGF-18 compound treatment or to determine a treatment regimen with an FGF-18 compound, the assay comprising: (a) subjecting a test sample from a human subject, diagnosed as having a cartilage disorder, to at least one genotyping assay that determines the genotypes of at least two loci, wherein said at least two loci are: (i) SNP1 and (ii) SNP2, (b) determining the genotypes of said at least two loci; (c) selecting a patient as being sensitive to a treatment with an FGF-18 compound when at least one of the following combinations of SNPs is determined to be present: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7, or (iii) SNP1 genotype A/G or A/A, or T/C or T/T in the complement of SEQ ID NO:6 and SNP2 genotype T/C or C/C, or A/G or G/G in the complement of SEQ ID No:7 and (d) optionally treating the patient selected in step (c) with an FGF-18 compound.

When the above assay is performed to determine a treatment regimen with an FGF-18 compound, step (c) is optional, whereas step (d) is preferably performed, or is performed.

The present invention further relates to an assay to determine non-sensitivity to an FGF-18 compound treatment, the assay comprising: (a) subjecting a test sample from a human subject diagnosed as having a cartilage disorder to at least one genotyping assay that determines the genotypes of at least two loci, wherein said at least two loci are: (i) SNP1 and (ii) SNP2, (b) determining the genotypes of said at least two loci; (c) selecting a patient as being non-sensitive to a treatment with an FGF-18 compound when the following combinations of SNPs are determined to be present: SNP1 genotype G/G, or C/C in the complement of the SEQ ID NO: 6; and SNP2 genotype T/T, or A/A in the complement of the SEQ ID NO: 7, and (d) optionally treating the patient selected in step (c) with a therapeutic compound other than an FGF-18 compound.

Before determining the genotype at one locus, in the above disclosed assays, it is necessary to obtain a nucleic acid (or test) sample of said subject, for instance by blood or saliva collection.

The present application also encompasses a method for selecting patients having a cartilage disorder for inclusion in or exclusion from treatment, or clinical trial, with an FGF-18 compound, based on the likelihood of their response to said treatment, comprising:
  a. Determining, from a nucleic acid sample, the genotype at both loci IL-1RN rs9005 and IL-1RN rs315952, wherein the patient's genotype with respect to said loci is predictive of the patient's risk for being sensitive or non-sensitive to said treatment, and
  b. Selecting patients that are suitable for said treatment or clinical trial, i.e., selecting the sensitive patients as being suitable for said treatment or said clinical trial.

Before determining the genotype at one locus, it is necessary to obtain a nucleic acid sample of said subject, for instance by blood or saliva collection. Preferably, the nucleic acid sample is a DNA sample. Thus, the present invention encompasses a method for selecting patients having a cartilage disorder for inclusion in or exclusion from treatment, or clinical trial, with an FGF-18 compound, based on the likelihood of their response to said treatment or clinical trial, comprising:
  a. Obtaining a nucleic acid sample of said subject,
  b. Determining, from a nucleic acid sample, the genotype at both loci IL-1RN rs9005 and IL-1RN rs315952, wherein the patient's genotype with respect to said loci is predictive of the patient's risk for being sensitive or not sensitive to said treatment, and
  c. Selecting patients that are suitable for said treatment or said clinical trial, i.e., selecting the sensitive patients as being suitable for said treatment or said clinical trial.

According to said method, patients having the genotype IL-1RN rs9005 G/G and IL-1RN rs315952 T/T, who are predicted being non-sensitives, are preferably excluded from the FGF-18 compound treatment, or from clinical trial related to FGF-18 compound. The other patients, the sensitive ones (including both intermediate-sensitives and super-sensitives; i.e., patients having the genotype G/G at IL-1RN rs9005 and T/C or C/C at IL-1RN rs315952 or A/G or A/A at IL-1RN rs9005 and T/T, T/C or C/C at IL-1RN rs315952) can be selected as suitable for the treatment with an FGF-18 compound, such as sprifermin.

Alternatively, the method for selecting a patient having a cartilage disorder for inclusion in or exclusion from treatment or clinical trial with an FGF-18 compound based on the likelihood of the patient's sensitivity to said FGF-18 compound comprised the steps of: (a) subjecting a test sample from a human subject, who is diagnosed as having cartilage disorder, to at least one genotyping assay adapted to determine the genotypes of at least two loci, wherein said at least two loci are: (i) SNP1 and SNP2, wherein SNP2 is position 27 of SEQ ID NO: 7 identified by rs315952, wherein the SEQ ID NO. 7 is a portion of genomic nucleic acid sequence of interleukin 1 receptor antagonist (IL-1RN); and (b) detecting from the genotypes of said at least two loci the presence of a genotype combination selected from: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7; or (iii) SNP1 genotype G/G, or C/C in the complement of the SEQ ID NO: 6 and SNP2 genotype T/T, or A/A in the complement of the SEQ ID NO: 7; and (c) selecting a patient for inclusion in treatment or clinical trial with an FGF-18 compound when conditions (i) or (ii) are detected based on the recognition that the genotype combinations (i) and (ii) are associated with a response to said FGF-18 compound, and excluding the patient from treatment or clinical trial with an FGF-18 compound when condition (iii) is detected based on the recognition that the genotype combination (iii) is associated with inadequate response to treatment with said FGF-18 compound.

The method for selecting a human subject for a clinical trial for testing an FGF-18 compound may alternatively comprise the steps of: (a) assaying a biological sample from a human subject diagnosed with a cartilage disorder for at least the following two single nucleotide polymorphisms: (i) SNP1 and (ii) SNP2; (b) determining the genotypes of the SNPs; and (c) selecting for the clinical trial the human subject who carries one of the following genotypes in said SNPs: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7; or (iii) a human subject who does not carry SNP1 genotype G/G, or C/C in the complement of the SEQ ID NO: 6 and SNP2 genotype T/T, or A/A in the complement of the SEQ ID NO: 7.

The present invention also describes a method of excluding a human subject from a clinical trial testing an FGF-18 compound, the method comprising the steps of: (a) assaying a biological sample from a human subject diagnosed with a cartilage disorder for at least the following two single nucleotide polymorphisms: (i) SNP1 and (ii) SNP2; (b) determining the genotypes of the SNPs; and (c) excluding from the clinical trial the human subject who carries the following genotype in said SNPs: SNP1 genotype G/G, or C/C in the complement of the SEQ ID NO: 6 and SNP2 genotype T/T, or A/A in the complement of the SEQ ID NO: 7; or excluding from the clinical trial the human subject who does not carry either of the following SNP genotypes: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7.

Besides the finding that as a function of his/her genotype, the subject could be classified as super-sensitive, sensitive or non-sensitive, it has surprisingly been found that the same genotype is also predictive of adverse events, such as AIRs. Indeed, further investigation and analysis of the SNP polymorphisms demonstrated a relation between the markers rs9005 and rs315952, in combination, with adverse events in the clinic, with MRI data concerning structural benefit and with symptomatic benefit as determined using the WOMAC questionnaire. Not only can these SNPs be used as a predictive tool of the patient's response to a treatment with an FGF-18 compound at cartilage volume level, but can also be used as a predictive tool of his/her risk to develop adverse events such as AIRs. Thus, the profile "structural benefit vs. potential adverse effects" of FGF-18 therapy would be useful to determine a better risk/benefit ratio, i.e., better outcome with lower risk of side effects in the patients.

This is based on the finding that the super-sensitives have higher WOMAC scores and higher likelihood of having an AIR event, notably when an FGF-18 compound is used, for instance at a dose of 100 mcg, compared to patients treated with the placebo. Similarly, the non-sensitives also have high WOMAC scores, at any dose, compared to patients treated with the placebo. It has also been shown that contrary to the results of a dose of 100 mcg, super-sensitives treated with an FGF-18 compound at a lower dose, for instance 30 mcg, have lower WOMAC scores (i.e., better WOMAC improvement) and lower likelihood of having an AIR event. In view of these results, it can be useful to select the patients based on their likelihood to respond/not respond to the FGF-18 compound treatment in combination with their risk level to present adverse events: the non-sensitives could be excluded from a treatment that is likely not to work for them (see above method of selection), and the super-sensitives may be subjected to an alternative treatment regimen.

The present invention is thus also directed to a method for selecting patients having a cartilage disorder for an alternative therapeutic regimen with an FGF-18 compound, based on their likelihood of being super-sensitives to FGF-18 compound treatment, comprising identifying the patient's nucleic acid at both of the polymorphic loci selected from the group consisting of IL-1RN rs9005 and IL-1RN rs315952, wherein the patient's genotype with respect to said loci is predictive of the subject's risk for being super sensitive to a treatment with said FGF-18 compound and allows the selection of said patient for an alternative therapeutic regimen that would be suitable for said patient, in which alternative therapeutic regimen the dose of FGF-18 compound that is to be administered is reduced compared to the dose of FGF-18 compound to be administered to a patient who is predicted to be sensitive but not super-sensitive to said FGF-18 compound treatment.

Also described herein is a method for selecting a patient having a cartilage disorder for a modified treatment regimen with an FGF-18 compound based on the likelihood of said patient of having Acute Inflammatory Reaction (AIR) events when treated with said compound, the method comprising the steps of (a) detecting from a nucleic acid sample obtained from the patient the genotype of (i) SNP1 and (ii) SNP2; and (b) selecting a modified treatment regimen for a patient when a combination of SNP1 genotype A/G or AA, or T/C or T/T in the complement of the SEQ ID NO: 6; and SNP2 genotype T/T, or A/A in the complement of the SEQ ID NO: 7 is detected.

Accordingly, patients having the genotype IL-1RN rs9005 A/G or A/A and IL-1RN rs315952 T/C or C/C, who are predicted to be super-sensitives, are preferably selected for an alternative therapeutic regimen in which the dose of FGF-18 compound to be administered is reduced.

Also described herein is a method for selecting patients having a cartilage disorder for an alternative therapeutic regimen with an FGF-18 compound, based on their likelihood of having AIR events when treated with an FGF-18 compound, comprising determining, from a nucleic acid sample, the genotype at both loci IL-1RN rs9005 and IL-1RN rs315952, wherein the patient's genotype with respect to said loci is predictive of the subject's risk for developing AIR events in response to treatment with said FGF-18 compound, and allows the selection of said patient for an alternative therapeutic regimen that would be suitable for said patient, in which alternative therapeutic regimen the dose of FGF-18 compound that is to be administered is reduced compared to the dose of FGF-18 compound to be administered to a patient who (1) is predicted to be sensitive and (2) does not present a risk for developing AIR events.

Accordingly, patients having the genotype A/G or A/A at IL-1RN rs9005 and T/C or C/C at IL-1RN rs315952, who are predicted to be super-sensitives, are preferably selected for an alternative therapeutic regimen in which the dose of FGF-18 to be administered is reduced, compared to the normal therapeutic regimen, i.e., the regimen for a patient who is predicted to be sensitive to FGF-18 compound treatment but who does not present a risk for developing AIR events.

The FGF-18 compound is usually to be administered intra-articularly at a dose of 100 mcg per injection, once weekly for 3 weeks per treatment cycle. In view of the good results at 30 mcg for the super-sensitives (see examples), a proposed alternative dosing regimen for those patients predicted to be super-sensitives is intra-articular administration of the FGF-18 compound at a dose of 30 mcg per injection, once weekly for 3 weeks per treatment cycle. It is to be understood that although at that time, the preferred dose is 100 mcg per injection, possibly reduced to 30 mcg per injection for super-sensitives, the present invention is not limited to said dosages. Therefore, the FGF-18 compound can be administered intra-articularly at a dose comprised between 50 and 300 mcg per injection, preferably between 60 and 250 mcg or even preferably between 100 and 200 mcg. For super-sensitive patients, said dose could be reduced, to ½ or to ⅓ for instance.

The present invention further encompasses an FGF-18 compound for use in the treatment of a patient having a cartilage disorder, characterized in that the patient has any combination of the genotype(s) selected from the group consisting of: (1) IL-1RN rs9005 G/G and IL-1RN rs315952 T/C or C/C, or (2) IL-1RN rs9005 A/G or A/A and IL-1RN rs315952 T/T, T/C or C/C. In addition, a patient bearing at least one A allele from IL-1RN rs9005 and at least one C allele from IL-1RN rs315952 T/T is eligible for FGF-18 compound treatment at a lower dose. It follows that a patient who does not meet these criteria (i.e., with genotype IL-1RN rs9005 G/G and IL-1RN rs315952 T/T) is preferably excluded from FGF-18 compound treatment (see Table 22).

The present invention is also directed to an assay for selecting a treatment regimen for a human subject with a cartilage disorder, the assay comprising: (a) subjecting a test sample from the human subject who is diagnosed as having a cartilage disorder to at least one genotyping assay that determines the genotypes of at least two loci, wherein said at least two loci are: (i) SNP1 and (ii) SNP2; (b) detecting from the genotypes of said at least two loci the presence of a genotype combination selected from: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7; or (iii) SNP1 genotype G/G, or C/C in the complement of the SEQ ID NO: 6 and SNP2 genotype T/T, or A/A in the complement of the SEQ ID NO: 7; and (c) selecting, and optionally administering, a treatment regimen comprising an effective amount of an FGF-18 compound when condition (i) or (ii) is detected based on the recognition that the genotype combinations (i) and (ii) are associated with a response to said compound, and excluding the treatment regimen comprising said compound when condition (iii) is detected based on the recognition that the genotype combination (iii) is associated with inadequate response to treatment with said compound.

Also described is a method for treating a human subject with a cartilage disorder, comprising administering a composition comprising an effective amount of an FGF-18 compound to a human subject who is diagnosed as having a cartilage disorder, and who is further determined to carry the combination of the single nucleotide polymorphisms (SNPs) selected from: (i) SNP1 genotype G/G, or C/C in the complement of the SEQ ID NO: 6, wherein SNP1 is position X of SEQ ID NO: 6 identified by rs9007, wherein the SEQ ID NO: 6 is a portion of genomic nucleic acid sequence of interleukin 1 receptor antagonist (IL-1RN); and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7, wherein SNP2 is position X of SEQ ID NO. 7 identified by rs317972, wherein the SEQ ID NO. 7 is a portion of genomic nucleic acid sequence of interleukin 1 receptor antagonist (IL-1RN).

Further disclosed is a method for treating a human subject with a cartilage disorder, comprising (a) assaying a biological sample of a subject who is diagnosed as having a cartilage disorder for at least the following two SNP loci: (i) SNP1, and (ii) SNP2; and (b) administering a treatment regimen comprising a composition comprising an effective amount of an FGF-18 compound to the subject if one of the following conditions is detected: (i) SNP1 genotype G/G, or C/C in the complement of the SEQ ID NO: 6; and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7.

Alternatively, the method for treating a human subject with a cartilage disorder comprises the steps of: (a) assaying a biological sample of a subject who is diagnosed as having a cartilage disorder for at least the following two SNP loci: (i) SNP1 and (ii) SNP2; and (b) administering a treatment regimen comprising a composition comprising an effective amount of an FGF-18 compound to the subject if SNP1 genotype G/G, or C/C in the complement of the SEQ ID NO: 6 and SNP2 genotype T/T, or A/A in the complement of the SEQ ID NO: 7 is not detected.

In yet another alternative, the method for selecting a subject having a cartilage disorder, wherein said cartilage disorder is susceptible to treatment with an FGF-18 compound, comprises:

(a) obtaining a biological sample from the subject with a cartilage disorder with the objective of determining whether the cartilage disorder in the subject is susceptible to treatment with said FGF-18 compound;

(b) contacting the biological sample with at least two oligonucleotides capable of interrogating whether or not the biological sample comprises the combination of the single nucleotide polymorphisms (SNPs) selected from (i) SNP1 genotype G/G, or C/C in the complement of the SEQ ID NO: 6, and SNP2 genotype T/C or CC, or A/G or GG in the complement of the SEQ ID NO: 7; or (ii) SNP1 genotype A/G or AA, or T/C or T/T in the complement of the SEQ ID NO: 6; and SNP2 genotype T/T, or A/A in the complement of the SEQ ID NO: 7;

(c) identifying the cartilage disorder in the subject as susceptible for treatment with said FGF-18 compound when either the combination of (i) or (ii) is detected in the biological sample and identifying the cartilage disorder in the subject as poorly or non-responsive to treatment with said compound when neither (i) nor (ii) is detected in the biological sample.

Also described herein is a method for selecting a treatment regimen for a subject with a cartilage disorder, comprising: (a) obtaining a test sample from the human subject diagnosed as having depression; (b) subjecting the test sample to at least one analysis to determine parameters of at least two single nucleotide polymorphisms (SNPs), wherein the at least two SNPs comprise the following: (i) SNP1 and (ii) SNP2; (c) detecting using the SNPs, the presence of at least one condition of the following or a combination thereof: i) SNP1 genotype G/G, or C/C in the complement of the SEQ ID NO: 6; and SNP2 genotype T/C or CC, or A/G or GG in the complement of the SEQ ID NO: 7; or ii) SNP1 genotype A/G or AA, or T/C or T/T in the complement of the SEQ ID NO: 6; and SNP2 genotype T/T, or A/A in the complement of the SEQ ID NO: 7; or iii) SNP1 genotype G/G, or C/C in the complement of the SEQ ID NO: 6 and SNP2 genotype T/T, or A/A in the complement of the SEQ ID NO: 7; and (d) providing a result output setting forth whether at least one of said condition is detected from the test sample and when condition (i) or (ii) is detected, then selecting and optionally administering a treatment regimen comprising an FGF-18 compound to the human subject, and when condition (iii) is detected, then not selecting or administering a treatment regimen comprising said compound to the human subject.

In the above mentioned methods, and assay, the patients having the genotype A/G or A/A at IL-1RN rs9007 (SNP1) and T/C or C/C at IL-1RN rs317972 (SNP2), who are predicted to be super-sensitives, are preferably selected for an alternative therapeutic regimen in which the dose of FGF-18 to be administered is reduced compared to the normal therapeutic regimen, i.e., the regimen for a patient who is predicted to be sensitive to FGF-18 compound treatment but who does not present a risk for developing AIR events.

In another embodiment of the invention, also provided are systems (and computer readable media for computer systems) for obtaining data. Said data can be used notably for assessing suitability of a treatment with an FGF-18 compound in a subject, for assessing the subject's risk of developing AIR when treated with an FGF-18 compound, or monitoring treatment efficacy of a subject with an FGF-18 compound. Said systems can be used during clinical trials, when a treatment with an FGF-18 compound has to be envisaged or when a treatment with said compound is already ongoing.

Therefore, an embodiment of the present invention includes a computer system for obtaining data from at least one test sample obtained from at least one subject with a cartilage disorder, the system comprising: (a) at least one determination module configured to receive said at least one test sample and perform at least one analysis on said at least one test sample to determine the presence or absence of the following conditions: (i) SNP1 genotype G/G, or C/C in the complement of the SEQ ID NO: 6, and SNP2 genotype T/C or CC, or A/G or GG in the complement of the SEQ ID NO: 7 or (ii) SNP1 genotype A/G or AA, or T/C or T/T in the complement of the SEQ ID NO: 6; and SNP2 genotype T/T, or A/A in the complement of the SEQ ID NO: 7; or (iii) SNP1 genotype G/G, or C/C in the complement of the SEQ ID NO: 6, and SNP2 genotype T/T, or A/A in the complement of the SEQ ID NO: 7; (b) at least one storage device configured to store data output from said determination module; and (c) at least one display module for displaying content based in part on the data output from said determination module, wherein the content comprises a signal indicative of the presence of at least one of these conditions, and optionally the absence of any one of these conditions.

Also described is a computer system for obtaining data from at least one test sample obtained from at least one subject, the system comprising: (a) a determination module configured to receive said at least one test sample and perform at least one genotyping analysis on said at least one test sample to determine the genotypes of at least two loci, wherein said at least two loci comprise: (i) SNP1 and (ii) SNP2; (b) a storage device configured to store output data from said determination module; (c) a computing module comprising specifically-programmed instructions to determine from the output data the presence of any of the combinations of polymorphisms selected from the following: i) SNP1 genotype G/G, or C/C in the complement of the SEQ ID NO: 6; and SNP2 genotype T/C or CC, or A/G or GG in the complement of the SEQ ID NO: 7; or ii) SNP1 genotype A/G or AA, or T/C or T/T in the complement of the SEQ ID NO: 6; and SNP2 genotype T/T, or A/A in the complement of the SEQ ID NO: 7; or iii) SNP1 genotype G/G, or C/C in the complement of the SEQ ID NO: 6 and SNP2 genotype T/T, or A/A in the complement of the SEQ ID NO: 7; and (d) a display module for displaying content based in part on the data output from said computing module, wherein the content comprises a signal indicative of the presence of the combination (i), (ii), or (iii) of the SNPs, and optionally the absence of any one or more or the combinations (i), (ii), and (iii) of the SNPs.

The computer readable medium can have computer readable instructions recorded thereon to define software modules for implementing a method on a computer. In such a case, said computer readable storage medium may comprise: (a) instructions for comparing the data stored on a storage device with reference data to provide a comparison result, wherein the comparison identifies the presence or absence of at least one of the following conditions: (i) SNP1 genotype G/G, or C/C in the complement of the SEQ ID NO: 6, and SNP2 genotype T/C or CC, or A/G or GG in the complement of the SEQ ID NO: 7, or (ii) SNP1 genotype A/G or AA, or T/C or T/T in the complement of the SEQ ID NO: 6; and SNP2 genotype T/T, or A/A in the complement of the SEQ ID NO: 7; or (iii) SNP1 genotype G/G, or C/C in the complement of the SEQ ID NO: 6, and SNP2 genotype T/T, or A/A in the complement of the SEQ ID NO: 7; and (b) instructions for displaying content based in part on the data output from said determination module, wherein the content comprises a signal indicative of the presence of at least one of the conditions, and optionally the absence of one or more of the conditions.

The computer readable storage media can be any available tangible media that can be accessed by a computer. Computer readable storage media include volatile and nonvolatile, removable and non-removable tangible media implemented in any method or technology for storage of information such as computer readable instructions, data structures, program modules or other data. Computer readable storage media include, but are not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and nonvolatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either a system, or a computer readable storage medium described herein, or may be distributed across one or more of such components.

The computer-readable media may be transportable such that the instructions stored thereon can be loaded onto any computer resource to implement the aspects of the present invention discussed herein.

The information determined in the determination module can be read by the storage device. The storage device is adapted or configured for having recorded thereon expression level or protein level information. Such information may be provided in digital form that can be transmitted and read electronically, e.g., via the Internet, on diskette, via USB (universal serial bus) or via any other suitable mode of communication.

In the context of the present invention as a whole, e.g., in the context of any one of the methods, uses, assays or kits according to the present invention, the preferred FGF-18 compound is a truncated FGF-18, such as sprifermin, and the preferred cartilage disorder is selected from the group consisting of osteoarthritis, cartilage injury, fractures affecting joint cartilage or surgical procedures with impact on joint cartilage, such as microfracture.

It is to be understood that in the context of the present invention as a whole, e.g., of any one of the methods, uses, assays, computer systems or kits according to the present invention, before determining the genotype at one locus, it is necessary to obtain a nucleic acid sample (or a test sample) of a subject, for instance by blood or saliva collection. Preferably, the nucleic acid sample is a DNA sample.

An individual afflicted with a cartilage disorder and to be tested and/or treated according to any of the methods, uses, assays, kits and other computer systems described herein is a human subject that is a candidate for treatment with an FGF-18 compound, such as sprifermin. In a preferred embodiment, the individual has been diagnosed with a cartilage disorder, or exhibits a symptom of a cartilage disorder.

It is also to be understand that in the context of the invention as a whole, determination can be performed in the complementary sequence of IL1-RN rs9005 and IL1-RN rs315952. It thus follows that according to the present invention as a whole, e.g., in the context of any one of the methods, uses, assays, computer systems or kits according to the present invention, the presence of the genotype C/C on the complementary sequence to IL-1RN rs9005 and A/A on the complementary sequence of IL-1RN rs315952 is predictive of no response or low response (i.e., non-sensitivity) to treatment with an FGF-18 compound. On the contrary, the presence of the genotype T/C or T/T on the complementary sequence at IL-1RN rs9005 and A/G or G/G on the complementary sequence of IL-1RN rs315952 is predictive of high response (high-sensitivity) to treatment with an FGF-18 compound. Said genotype will also be a marker of likelihood for a patient of developing AIRs events when treated with said FGF-18 compound. The other genotypes at these loci are predictive of intermediate sensitivity (i.e., C/C in the complement of IL-1RN rs9005 and A/G or G/G in the complement of IL-1RN rs315952 or T/C or T/T in the complement of IL-1RN rs9005 and A/A in the complement of IL-1RN 315952).

In a further embodiment, the present invention encompasses a kit comprising means for performing the methods described above and instructions for use. In particular, the kit comprises at least a couple of specific primers or probes for detecting the presence or absence of the alleles. Preferably, it comprises two couples of specific primers or probes for genotyping the alleles at loci IL-1RN rs9005 and IL-1RN rs315952.

The kit may comprise an oligonucleotide array affixed with a plurality of oligonucleotide probes that interrogate no more than 20 single nucleotide polymorphisms (SNPs), said SNPs comprising: (i) SNP1 genotype G/G, or C/C in the complement of the SEQ ID NO: 6, and SNP2 genotype T/C or CC, or A/G or GG in the complement of the SEQ ID NO: 7; or (ii) SNP1 genotype A/G or AA, or T/C or T/T in the complement of the SEQ ID NO: 6 and SNP2 genotype T/T, or A/A in the complement of the SEQ ID NO: 7; or (iii) SNP1 genotype G/G, or C/C in the complement of the SEQ ID NO: 6, and SNP2 genotype T/T, or A/A in the complement of the SEQ ID NO: 7; an optional container containing a detectable label to be conjugated to a nucleotide molecule derived from a test sample of a subject diagnosed as having a cartilage disorder; and at least one reagent.

Alternatively, the oligonucleotide array affixed with a plurality of oligonucleotide probes interrogates no more than 17 single nucleotide polymorphisms (SNPs), no more than 10 single nucleotide polymorphisms (SNPs) or no more than 7 single nucleotide polymorphisms (SNPs).

Also described in the context of this invention is a kit comprising: a plurality of oligonucleotide primers or sets of primers that each bind to interrogate no more than one specific allele of no more than 20 single nucleotide polymorphisms (SNPs), wherein each subset of oligonucleotide primers that bind to a specific allele of an SNP is labeled with a distinct reporter, and wherein said SNPs comprise the following SNPs: i) SNP1 genotype G/G, or C/C in the complement of the SEQ ID NO: 6, and SNP2 genotype T/C or CC, or A/G or GG in the complement of the SEQ ID NO: 7; or ii) SNP1 genotype A/G or AA, or T/C or T/T in the complement of the SEQ ID NO: 6 and SNP2 genotype T/T, or A/A in the complement of the SEQ ID NO: 7; or iii) SNP1 genotype G/G, or C/C in the complement of the SEQ ID NO: 6, and SNP2 genotype T/T, or A/A in the complement of the SEQ ID NO: 7; and at least one reagent.

Alternatively, the plurality of oligonucleotide primers or sets of primers that each bind to interrogate no more than one specific allele of no more than 17 single nucleotide polymorphisms (SNPs), or no more than one specific allele of no more than 10 single nucleotide polymorphisms (SNPs) or no more than one specific allele of no more than 7 single nucleotide polymorphisms (SNPs).

In a further embodiment, the present invention discloses a kit for selecting a treatment regimen for a subject with a cartilage disorder, comprising at least one reagent for determining, in a test sample of a human subject diagnosed as having a cartilage disorder, the presence or absence of the following SNPs: i) SNP1 genotype G/G, or C/C in the complement of the SEQ ID NO: 6, and SNP2 genotype T/C or CC, or A/G or GG in the complement of the SEQ ID NO: 7; or ii) SNP1 genotype A/G or AA, or T/C or T/T in the complement of the SEQ ID NO: 6 and SNP2 genotype T/T, or A/A in the complement of the SEQ ID NO: 7; or iii) SNP1 genotype G/G, or C/C in the complement of the SEQ ID NO: 6 and SNP2 genotype T/T, or A/A in the complement of the SEQ ID NO: 7.

In some embodiments, the oligonucleotides in the kit are either allele-specific probes or allele-specific primers. In other embodiments, the kit comprises primer-extension oligonucleotides. In still further embodiments, the set of oligonucleotides is a combination of allele-specific probes, allele-specific primers, or primer-extension oligonucleotides.

The composition and length of each oligonucleotide in a kit of the invention will depend on the nature of the genomic region containing the genetic marker of the invention as well as the type of assay to be performed with the oligonucleotide and is readily determined by the skilled artisan. For example, the polynucleotide to be used in the assay may constitute an amplification product, and thus the required specificity of the oligonucleotide is with respect to hybridization to the target region in the amplification product rather than in genomic DNA isolated from the individual.

In preferred embodiments, each oligonucleotide in the kit is a perfect complement of its target region. An oligonucleotide is said to be a "perfect" or "complete" complement of another nucleic acid molecule if every nucleotide of one of the molecules is complementary to the nucleotide at the corresponding position of the other molecule. While perfectly complementary oligonucleotides are preferred for detecting polymorphisms, departures from complete complementarity are contemplated where such departures do not prevent the molecule from specifically hybridizing to the target region as defined above. For example, an oligonucleotide primer may have a non-complementary fragment at its 5' end, with the remainder of the primer being completely complementary to the target region. Alternatively, non-complementary nucleotides may be interspersed into the probe or primer as long as the resulting probe or primer is still capable of specifically hybridizing to the target region.

In some preferred embodiments, each oligonucleotide in the kit specifically hybridizes to its target region under stringent hybridization conditions. Stringent hybridization conditions are sequence-dependent and vary depending on the circumstances. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. As the target sequences are generally present in excess, at $T_m$, 50% of the probes are occupied at equilibrium. Typically, stringent conditions include a salt concentration of at least about 0.01 to 1.0 M Na ion concentration (or other salts) at pH 7.0 to 8.3 and the temperature is at least about 25° C. for short oligonucleotide probes (e.g., 10 to 50 nucleotides). Stringent conditions can also be achieved with the addition of destabilizing agents such as formamide. For example, conditions of 5×SSPE (750 mM NaCl, 50 mM Na Phosphate, 5 mM EDTA, pH 7.4) and a temperature of 25-30° C. are suitable for allele-specific probe hybridizations.

The oligonucleotides in kits of the invention may be comprised of any phosphorylation state of ribonucleotides, deoxyribonucleotides, and acyclic nucleotide derivatives, and other functionally equivalent derivatives. Alternatively, the oligonucleotides may have a phosphate-free backbone, which may be comprised of linkages such as carboxymethyl, acetamidate, carbamate, polyamide [peptide nucleic acid (PNA)] and the like. The oligonucleotides may be prepared by chemical synthesis using any suitable methodology known in the art, or may be derived from a biological sample, for example, by restriction digestion. The oligonucleotides may contain a detectable label, according to any technique known in the art, including use of radiolabels, fluorescent labels, enzymatic labels, proteins, haptens, antibodies, sequence tags and the like. The oligonucleotides in the kit may be manufactured and marketed as analyte specific reagents (ASRs) or may constitute components of an approved diagnostic device.

In other preferred embodiments, the kit includes an instruction manual that describes the various ways the kit may be used to detect the presence or absence of a genetic marker of the invention.

In a preferred embodiment, the set of oligonucleotides in the kit are allele-specific oligonucleotides. As used herein, the term allele-specific oligonucleotide (ASO) means an oligonucleotide that is able, under sufficiently stringent conditions, to hybridize specifically to one allele of a genetic marker, at a target region containing the genetic marker, while not hybridizing to the same region containing a different allele. As understood by the skilled artisan, allele-specificity will depend upon a variety of readily optimized stringency conditions, including salt and formamide concentrations, as well as temperatures for both the hybridization and washing steps.

Typically, an ASO will be perfectly complementary to one allele while containing a single mismatch for another allele. In ASO probes, the single mismatch is preferably within a central position of the oligonucleotide probe as it aligns with the genetic marker in the target region (e.g., approximately the 7th or 8th position in a 15mer, the 8th or 9th position in a 16mer, and the 10th or 11th position in a 20mer). The single mismatch in ASO primers is located at the 3' terminal nucleotide, or preferably at the 3' penultimate nucleotide. ASO probes and primers hybridizing to either the coding or non-coding strand are contemplated by the invention.

In other preferred embodiments, the kit comprises a pair of allele-specific oligonucleotides for a genetic marker of the invention to be assayed, with one member of the pair being specific for one allele and the other member being specific for another allele. In such embodiments, the oligonucleotides in the pair may have different lengths or have different detectable labels to allow the user of the kit to determine which allele-specific oligonucleotide has specifically hybridized to the target region, and thus determine which allele is present in the individual at the assayed marker locus.

In still other preferred embodiments, the oligonucleotides in the kit are primer-extension oligonucleotides. Termination mixes for polymerase-mediated extension from any of these oligonucleotides are chosen to terminate extension of the oligonucleotide at the genetic marker of interest, or one base thereafter, depending on the alternative nucleotides present at the marker locus.

The methods and kits according to the present invention are useful in clinical diagnostic applications. However, as used herein, the term "diagnostic" is not limited to clinical or medical uses, and the diagnostic methods and kits of the invention claimed herein are also useful in any research application, and during clinical trials, for which it is desirable to test a subject for the presence or absence of any genetic marker described herein.

In the context of the invention, the presence or absence of a particular allele or pair of alleles at the locus of a genetic marker of the invention in an individual may be detected by any technique known per se to the skilled artisan, including sequencing, pyrosequencing, selective hybridization, selective amplification and/or mass spectrometry including matrix-assisted laser desorption/ionization time-of-flight mass spectrometry (MALDI-TOF MS). In a particular embodiment, the alteration is detected by selective nucleic acid amplification using one or several specific primers. The alteration is detected by selective hybridization using one or several specific probes.

Further techniques include gel electrophoresis-based genotyping methods such as PCR coupled with restriction fragment length polymorphism (RFLP) analysis, multiplex PCR, oligonucleotide ligation assay, and minisequencing; fluorescent dye-based genotyping technologies such as oligonucleotide ligation assay, pyrosequencing, single-base extension with fluorescence detection, homogeneous solution hybridization such as TaqMan, and molecular beacon genotyping; sequencing-based technologies such as Sanger sequencing and next-generation sequencing platforms; rolling circle amplification and Invader assays as well as DNA chip-based microarray and mass spectrometry genotyping technologies. Protein expression analysis methods are known in the art and include 2-dimensional gel electrophoresis, mass spectrometry and antibody microarrays. Sequencing can be carried out using techniques well known in the art, e.g., using automatic sequencers. The sequencing may be performed on the complete gene or, more preferably, on specific domains thereof, typically those known or suspected to carry deleterious mutations or other alterations. Amplification may be performed according to various techniques known in the art, such as by polymerase chain reaction (PCR), ligase chain reaction (LCR) and strand displacement amplification (SDA). These techniques can be performed using commercially available reagents and protocols. A preferred technique is allele-specific PCR.

Other embodiments of the invention within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

DESCRIPTION OF THE FIGURES

General notes: In the figures, 1) the terms TT, CC, GG or AA are to be understood as being T/T, C/C, G/G or A/A, and 2) the term CTA is to be understood as C-T-A.

FIGS. 16(a)-(h): Set out the full length amino acid and nucleic acid sequences corresponding to the "SEQ ID NOs" referenced in the instant patent application.

DESCRIPTION OF THE SEQUENCES

Figure 1:
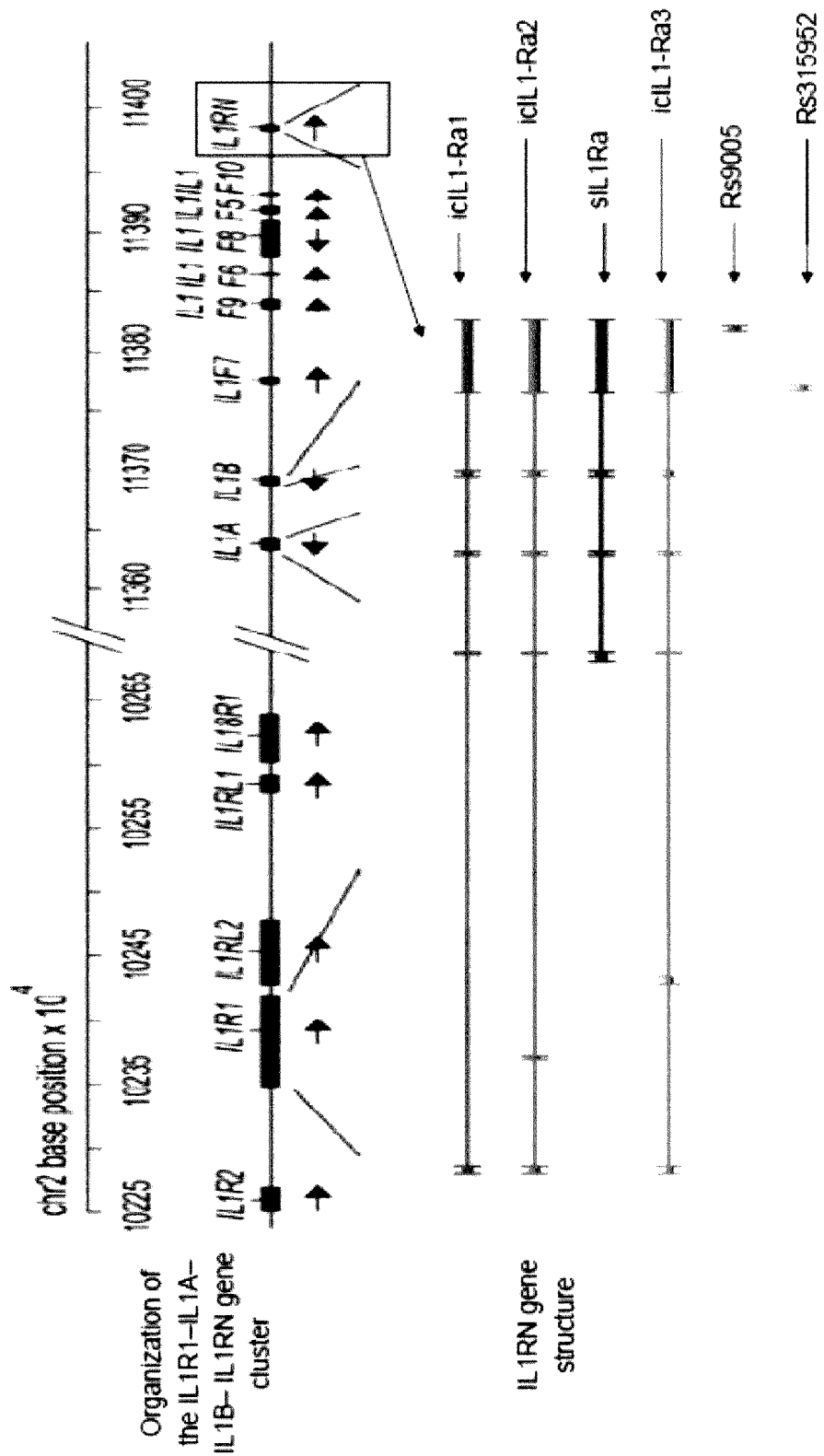
FIG. 1: Organization of the IL1R1-IL1A-IL1B-IL1RN gene cluster. Both rs315952 and rs9005 are located in the last IL1RN exon. Although there is only 1107 bp between them, these SNPs are not inherited together (i.e., not in linkage disequilibrium). IL1RN-rs9005 is within the 3' UTR region and overlaps both a transcription factor (ChIP-seq sequence: FOSL2) and a DNAse cluster (regulatory regions and promoter tend to be DNAse sensitive). IL1RN-r5315952 is a coding silent SNP (i.e., does not lead to an amino acid change).

SEQ ID NO: 1: Amino acid sequence of the native human FGF-18.

SEQ ID NO: 2: Amino acid sequence of the recombinant truncated FGF-18 (trFGF-18).

SEQ ID NO: 3: IL1RN gene.

SEQ ID NO: 4: IL1RN rs9005 locus.

SEQ ID NO: 5: IL1RN rs315952 locus.

SEQ ID NO: 6: Specific region from IL1RN rs9005 locus (corresponding to nucleotide 415 to nucleotide 466 of SEQ ID NO: 4), wherein N is A or G.

SEQ ID NO: 7: Specific region from IL1RN rs315952 locus (corresponding to nucleotide 415 to nucleotide 466 of SEQ ID NO: 5), wherein N is C or T.

SEQ ID NO: 8: rs315952 primer 1.

SEQ ID NO: 9: rs315952 primer 2.
SEQ ID NO: 10: rs9005 primer 1.
SEQ ID NO: 11: rs9005 primer 2.

EXAMPLES

1. Genotyping Background:

The level of cartilage volume growth and the associated risks of adverse events in response to sprifermin treatment in cartilage disorders, such as osteoarthritis, cartilage injury, fractures affecting joint cartilage or surgical procedures with impact on joint cartilage (e.g., microfracture), may each be associated with a specific genetic variation in one or several genes. In the present study, the search for associations between genes containing variations and disease or response to treatment was focused on candidate genes that were selected based on the physiological role of the proteins they encode and their potential implication in the cartilage disorders, or in the response to sprifermin treatment. The list of selected candidate SNPs that have been tested is given in Table 1.

Response to sprifermin treatment was measured by change in cartilage volume from baseline 1 year after the beginning of treatment with sprifermin.

It is noted that candidate and whole genome scan SNP markers were not kept for further analysis if any of the following criteria were met:
  Rare variant SNP in the PGx ITT population: Minor Allele Frequency (MAF)<10% for both candidate SNP and whole genome scan SNPs.
  Questionable genotyping quality, as measured by a high rate (5%) of missing data.
  Significant deviation from the Hardy-Weinberg equilibrium (Bonferroni adjusted p value less than 5% for candidate SNPs or FDR (i.e., Benjamini-Hochberg adjusted p value) less than 20% for whole genome scan SNPs).
  Subjects with gender discrepancy between the clinical database and the predicted gender from whole genome scan SNP data (chromosome X) are excluded.

The candidate genes selected have been previously implicated in cartilage disorders, such as osteoarthritis. The purpose of the study was to investigate whether the level of response, i.e., cartilage volume growth and/or occurrence of adverse events in response to sprifermin treatment in cartilage disorder, is correlated with a specific DNA variant or pattern of variants. The existence of such a correlation would indicate that either the gene(s) carrying the identified variant(s) or one or more genes lying in the vicinity of the variants may be susceptibility gene(s).

2. Materials and Methods 2.1. FGF-18 Compound

The FGF-18 compound used as a treatment in the present examples is sprifermin. It is a truncated form of FGF-18, as defined in the section "definitions".

2.2. Sample Reception and Double Coding

Blood samples were received from patients participating in study 28980 (A randomized, double blind, placebo-controlled, multicenter, single and multiple ascending dose study of sprifermin, administered intra-articularly in patients with primary osteoarthritis of the knee who are not expected to require knee surgery within one year).

In order to comply with the Pharmacogenomics (PGx) Informed Consent Form (ICF), which covered the DNA analysis, all samples were double-coded by the Biobank (Merck Serono, Geneva) to ensure an additional level of subject anonymity. The Biobank provided the Biomarker Data Management group with the double key coding as a flat file containing both the PGx ID and the Subject ID for each subject. Additional verifications were performed to ensure that no DNA analyses are performed on subjects who did not consent to the PGx study.

2.3. DNA Sample Extraction, Amplification, Fragmentation and Labeling

The analysis was performed on DNA extracted from blood. A total of 140 blood samples were received. Out of these 140, 3 samples were destroyed by the genomic laboratory as the patients withdrew their consent during the course of study, resulting in 137 DNAs analyzed corresponding to 137 patients. Thus 137 patients were genotyped and eligible for the association studies.

Genomic DNA was extracted from EDTA blood samples using a Qiagen extraction kit (QIAamp DNA Blood Maxi Kit). After extraction, measures of sample absorbance at wavelengths of 260 nm and 280 nm using a spectrophotometer and electrophoresis on agarose gels were performed to estimate the quality and quantity of genomic DNA samples.

For each plate, genomic DNA samples were digested with Nspl and Styl restriction endonucleases, ligated with specific adaptors (Nsp or Sty), processed in parallel until the Polymerase Chain Reactions (PCR). PCR amplified the product of ligation in triplicate for Styl reactions and in quadruplicate for Nspl reactions, to product a large efficiency. All the PCR products were pooled, purified, quantified, fragmented and labeled.

The PCR amplification step was evaluated using electrophoresis agarose gel. The DNA quantification step was measured using a spectrophotometer. The DNA fragmentation step was evaluated using electrophoresis agarose gel. The average DNA fragment size should be lower than 180 bp.

2.4. DNA Microarray Technology (Whole Genome Scan)

The Affymetrix Genome Wide SNP 6.0 Assays were used to perform the Whole Genome Scan (hypothesis free approach). The Affymetrix technology is based on a DNA chip allowing the genotyping of approximately 906 600 single nucleotide polymorphisms (SNPs) per patient. SNPs are randomly distributed in all the chromosomes and are used as tagging markers of the corresponding genomic area. The details of process and protocol followed the PGX Affymetrix wide-genome SNP 5.0/6.0 technology.

For each sample, the labeled product was hybridized into the Affymetrix Genome Wide SNP 6.0 GeneChip. Two lots of chips were used for both sets.

After hybridization and staining, the Affymetrix Gene Chips were scanned to create image data (DAT) files. After that, AGCC Software automatically aligned a grid on the DAT files and computed the Cell Intensity data (CEL) file. Afterwards the CEL data passed on to Genotyping Console software that generated Probe Analysis (CHP) data.

Analysis quality control (QC) was performed using Genotyping Console Software assessing the Dynamic Model QC (DM) call rate analysis of a subset of 3022 SNPs following chip scanning. DM call rates measure the consistency of intensities within each SNP, with four possible genotyping states (Null, AA, AB and BB). It provides an estimate of the overall quality for a data sample prior to performing full clustering analysis. It is based on QC Call Rate.

The QC Call Rate (QC CR) is well correlated with clustering performance and is an effective single-sample metric for deciding what samples should be used in down-stream clustering. The fixed threshold for Genome wide SNP6.0 arrays is >=86%. In addition to QC CR, another algorithm has been developed for SNP 6.0 arrays. This new algorithm is the Contrast QC. The contrast QC is a metric that captures the ability of an experiment to resolve SNP signals into three genotype clusters. It measures the separation of allele intensities into three clusters in "contrast space". Contrast space is a projection of the two-dimensional allele intensity space into an informative single dimension. The default threshold is >=0.4 for each sample. The results of QC are automatically displayed in the Intensity QC Table. Samples which pass the QC threshold (call rate >86% and contrast QC >0.4) are noted as "bound in", and those which did not pass the QC (call rate <86% or contrast QC<0.4) are noted as "bound out". The genomic DNA samples of the study passed all QC.

2.5. TaqMan SNP Genotyping (Candidate Gene)

TaqMan SNP Genotyping was performed to detect selected markers based on literature information. A total of 19 SNPs distributed onto 8 candidate genes were selected and carried out in two periods (see Tables 2a and 2b). In a TAQMAN SNP Genotyping assay, two locus-specific PCR primers surrounding the SNP are used to amplify a fragment of about 100 bp. Two allele-specific probes are then hybridized to their specific SNP sequence (see for instance Table 3). Each probe was labeled at its 5' extremity with either a fluorescent reporter dye (FAM) or VIC reporter dye. Each probe also has a non-fluorescent quencher dye, MGB, at the 3' end. In each PCR cycle, if the target sequence of the allele-specific probe is amplified, the probe will hybridize to the DNA during the annealing step and extend. When the DNA polymerase comes into contact with this hybridized probe, the reporter dye of the probe is cleaved from the probe, leaving the quencher dye behind. In each cycle of the PCR, cleavage of the reporter dyes from one or both of the allele-specific probes causes an exponential increase in the fluorescent intensity. At PCR completion, the total fluorescence of each sample is read on the ABI 9700 (384-well format). If fluorescence is observed from only one probe, the sample is homozygous for this allele. If fluorescence is observed from both allele-specific probes, the sample is heterozygous for both alleles. If the probe does not hybridize, the fluorescence of the dye is "quenched" or reduced by the quencher dye, and thus minimal fluorescence is observed, indicating a failed genotype.

Protocol is detailed in the datasheet of TAQMAN SNP Genotyping.

Period 1: DNA samples were genotyped with 17 TAQMAN SNP assays (see Table 2a).

Period 2: DNA samples were genotyped with 2 further TAQMAN SNP assays (see Table 2b).

For each TAQMAN SNP assay, the NTC cluster was specific and all NTCs were undetermined, the three distinct sample clusters were present and genotyping was automatically assigned and the call rate was specified to be above 85 percent.

For each of the 19 TAQMAN SNP assays in the three parts, acceptance criteria were reached.

2.6. SNP Filtering

Candidate and whole genome scan SNP markers were not kept for analysis if any of the following criteria were met:
Rare variant SNP in the PGx ITT population: Minor Allele Frequency (MAF)<10% for both candidate SNP and whole genome scan SNPs.
Questionable genotyping quality, as measured by a high rate (5%) of missing data.
Significant deviation from the Hardy-Weinberg equilibrium (Bonferroni adjusted p value less than 5% for candidate SNPs or FDR (i.e., Benjamini-Hochberg adjusted p value) less than 20% for whole genome scan SNPs).
Subjects with gender discrepancy between the clinical database and the predicted gender from whole genome scan SNP data (chromosome X) are excluded.

2.7. Association Tests

For association tests, genotype data were coded as presence/absence of the SNP minor allele (i.e., homozygous for major allele compared to at least one copy of the minor allele).

2.7.1. Association with Acute Inflammatory Reactions (AIRs)

In these analyses, only subjects treated with 100 mcg FGF-18 dose were used. For single marker analysis, two approaches were used: Fisher's exact test and a multivariate linear model (i.e., AIR status ~SNP+Kellgren Lawrence grade [2; 3]+Gender [Female; Male]+Age [<65; ≥65]+BMI [<30, ≥30]. In this model, significance of each term in the model was assessed with a type III anova).

2.7.2. Association with WOMAC Total Scores and Total Cartilage Volume

Association between change from baseline at week 52 (termination date), both for WOMAC total scores and total cartilage volume, was assessed using the following linear model:

Rank(change in endpoint) ~Arm [Placebos, Treated subjects e.g., with FGF-18 100 mcg dose]+genotype group+Kellgren-Lawrence grade [2; 3]+Gender [Female; Male]+Age [<65; ≥65]+BMI [<30, ≥30]. Significance of each term in the model was assessed with a type III anova and significance threshold was set at alpha=5%.

2.7.3. Association Between a Given Genotype Group and Kellgren-Lawrence Grade

To test whether a given genotype group (for, e.g., subjects with the 'IL-1RN rs9005 G/G and IL-1RN rs315259 T/T' genotype) had a significant enrichment or paucity in subjects with severe osteoarthritis (i.e., Kellgren-Lawrence grade 3), independent tests were performed using a Fisher's exact test and from the following contingency table:

|  | Grade 3 | Grade 2 |
|---|---|---|
| # of subjects from a given genotype group |  |  |
| # of subjects from the remaining genotype groups |  |  |

All available subjects from any dose regimen (including placebos) were included in this analysis. P-values were computed using a two-sided test and significance was set at alpha=5%. Odds ratio and their 95% confidence intervals were also computed.

2.8. Haplotype Analyses

Genotype data from SNPs rs419598, rs315952, and rs9005 were phased (using the MACH software, version 1.0.18.c, Li Y et al., 2010) to infer presence or absence of the C-T-A haplotype in subjects. The following MACH parameters were used: "—rounds 50—states 200—phase". Association with AIRs was tested using a Fisher's exact test (significance threshold set at alpha=5%).

2.9. Combinatorial Analyses Between Candidate SNPs

In initial association analyses (data not shown), the rs9005 SNP was found to be significantly associated with AIRs. Combinatorial analyses (i.e., epistasis) were performed to test whether IL-1RN rs9005, in combination of another SNP from a list of about 120 candidate SNPs, would be a better AIR predictor (see Table 1). Such analysis was performed using a logistic regression with the following model:

AIR status ~rs9005*another SNP+Kellgren-Lawrence grade [2; 3]+Gender [Female; Male]+Age [<65; ≥65]+BMI [<30, ≥30].

Significance of each term in the model was assessed with a type III anova. Interaction p-values were adjusted for multiple testing using the Benjamini-Hochberg procedure (Benjamini and Hochberg, 1995, J. of the Royal Statistical Society Series B(57):289) and significance threshold was set at FDR=5%. Epistasis effects were confirmed using the statistical approach described in Wrapati et al., 2011.

2.10. Performance Metrics at Predicting AIRs

Performance metrics at predicting AIRs were derived from the corresponding contingency table. These metrics included sensitivity, specificity, accuracy, precision, negative predictive value and F1 score (i.e., harmonic mean of precision and recall).

3. Results 3.1. Predictive Analyses

Figure 2:
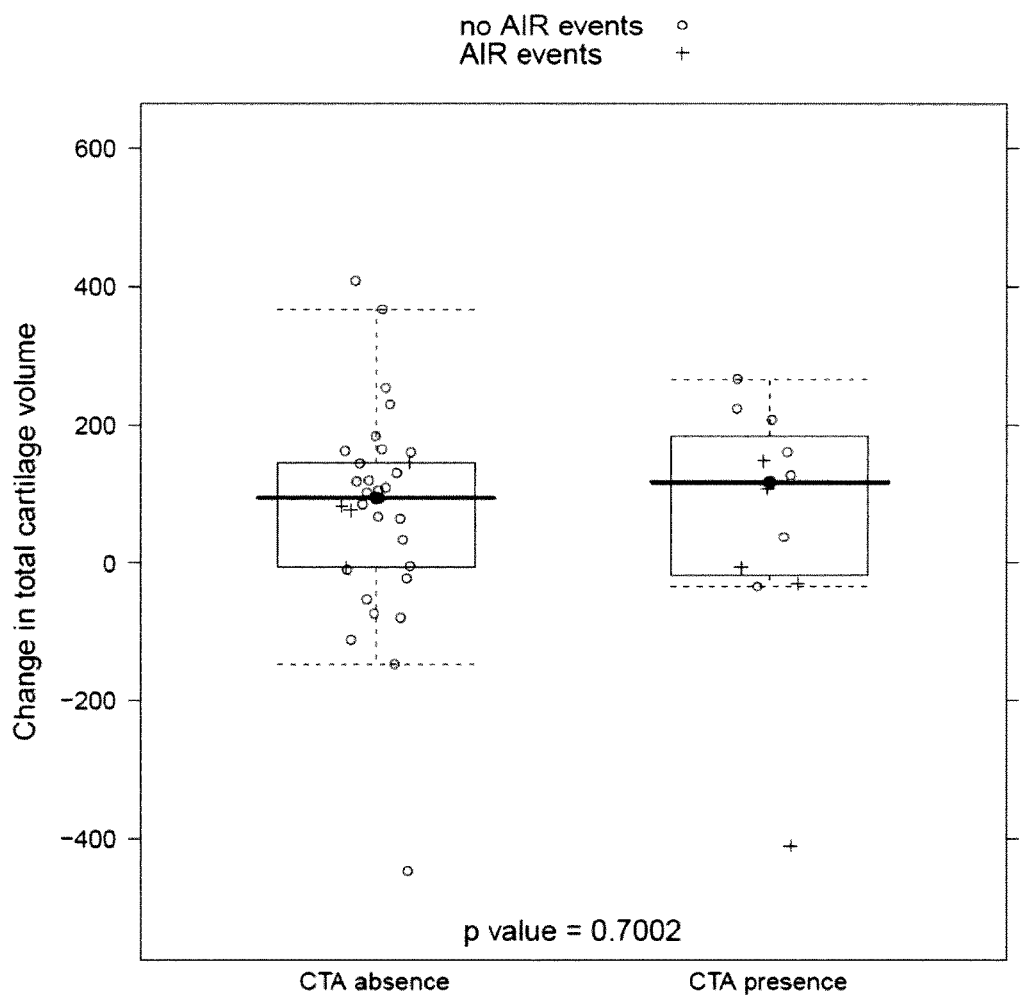
FIG. 2: Stratification of the patients as a function of presence or absence (from at least one copy) of the C-T-A haplotype. The Y axis shows change at Week 52 in total cartilage volume (unit: $mm^3$). Each point corresponds to a subject; a circle indicates a subject without AIR while a cross indicates a subject with AIRs. Indicated p-value was obtained from a non-parametric univariate test (ranksum test).
Figure 3:
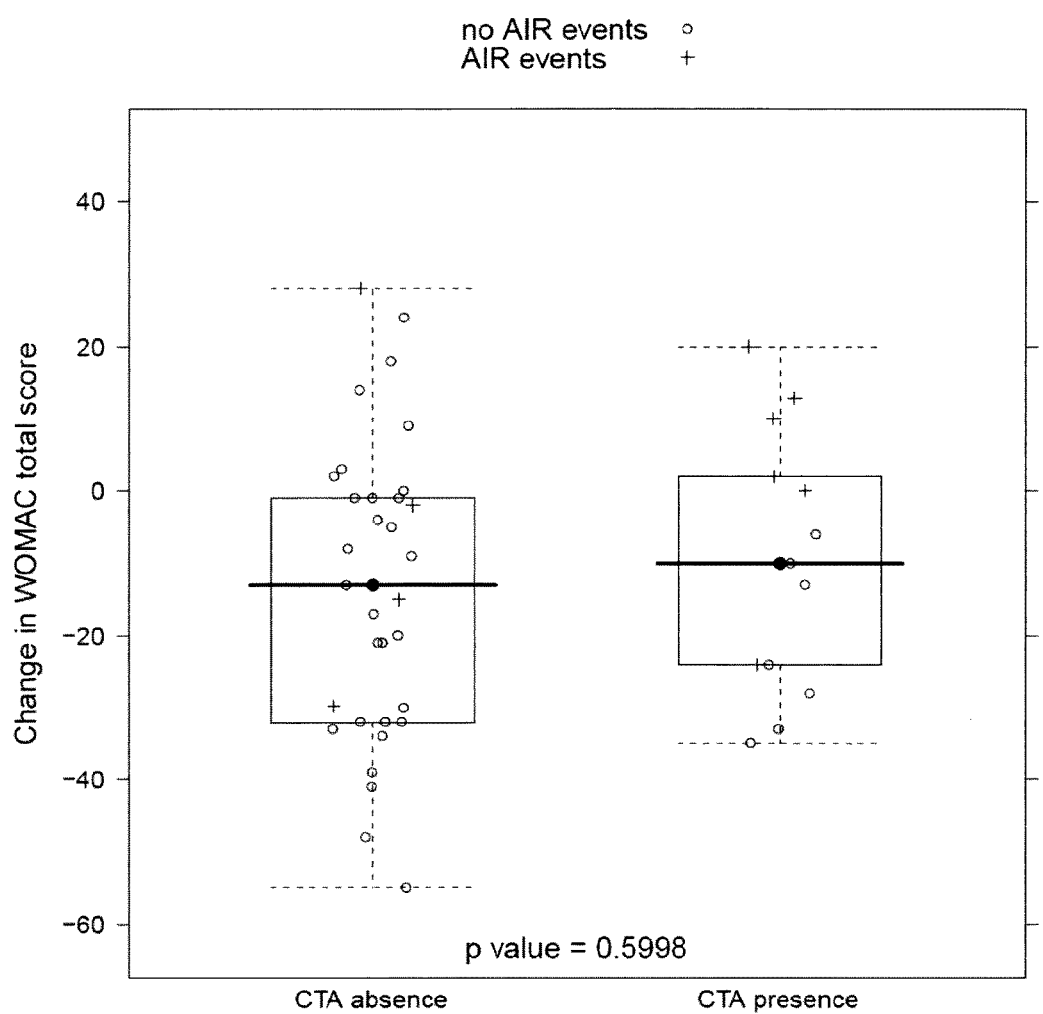
FIG. 3: Stratification of the patients as a function of presence or absence (from at least one copy) of the C-T-A haplotype. The Y axis shows change at Week 52 in WOMAC total score. Each point corresponds to a subject; a circle indicates a subject without AIR while a cross indicates a subject with AIRs. Indicated p-value was obtained from a non-parametric univariate test (ranksum test).
Figure 4:
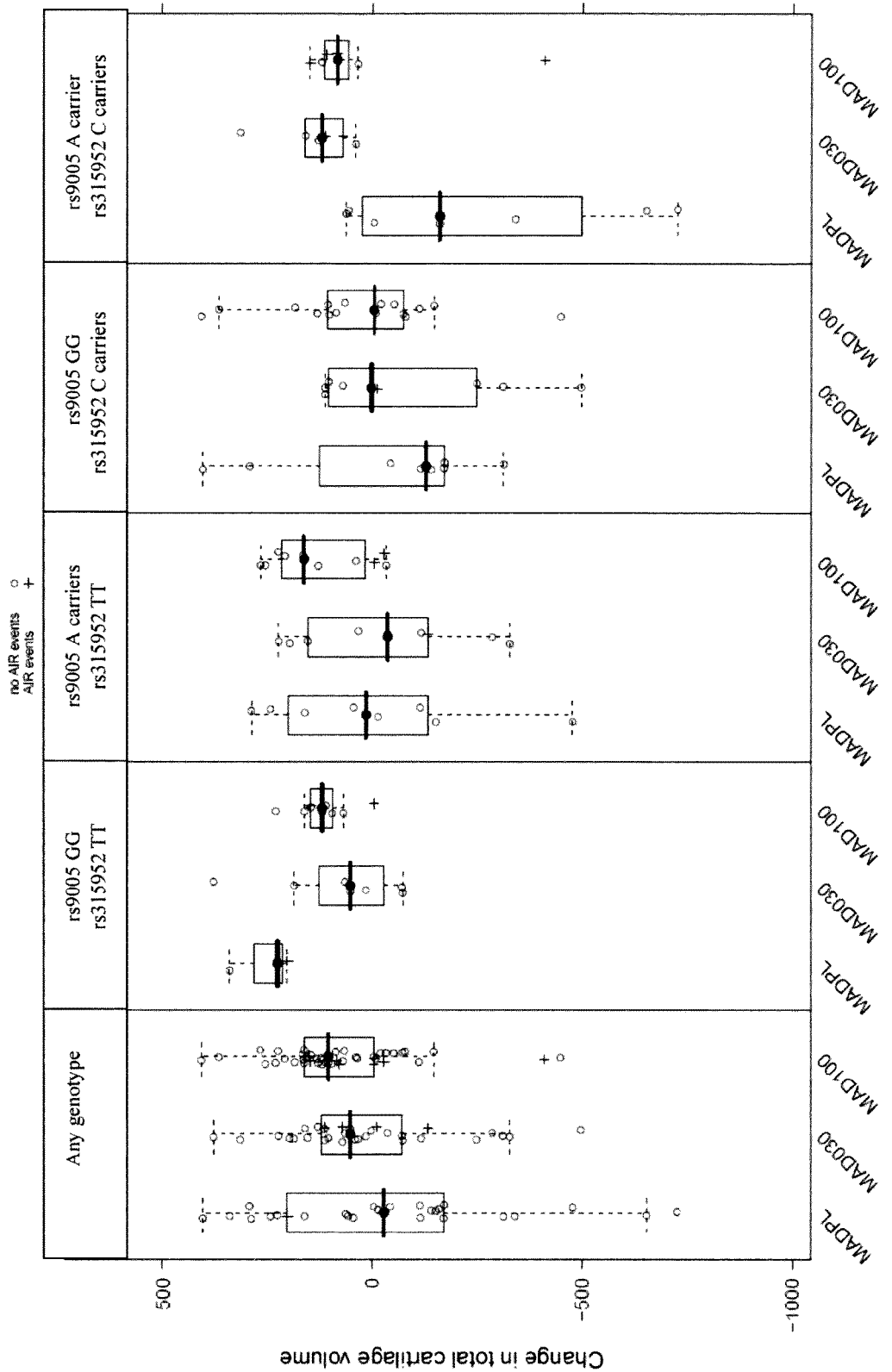
FIG. 4: Change in total cartilage volume ($mm^3$) at Week 52 stratified by dose regimen and stratified by their genotype at both rs315952 and rs9005. Each point corresponds to a subject; a circle indicates a subject without AIR while a cross indicates a subject with AIRs. MRI data from the MAD010 cohort showed aberrant variability and were not included in any analyses.
Figure 5:
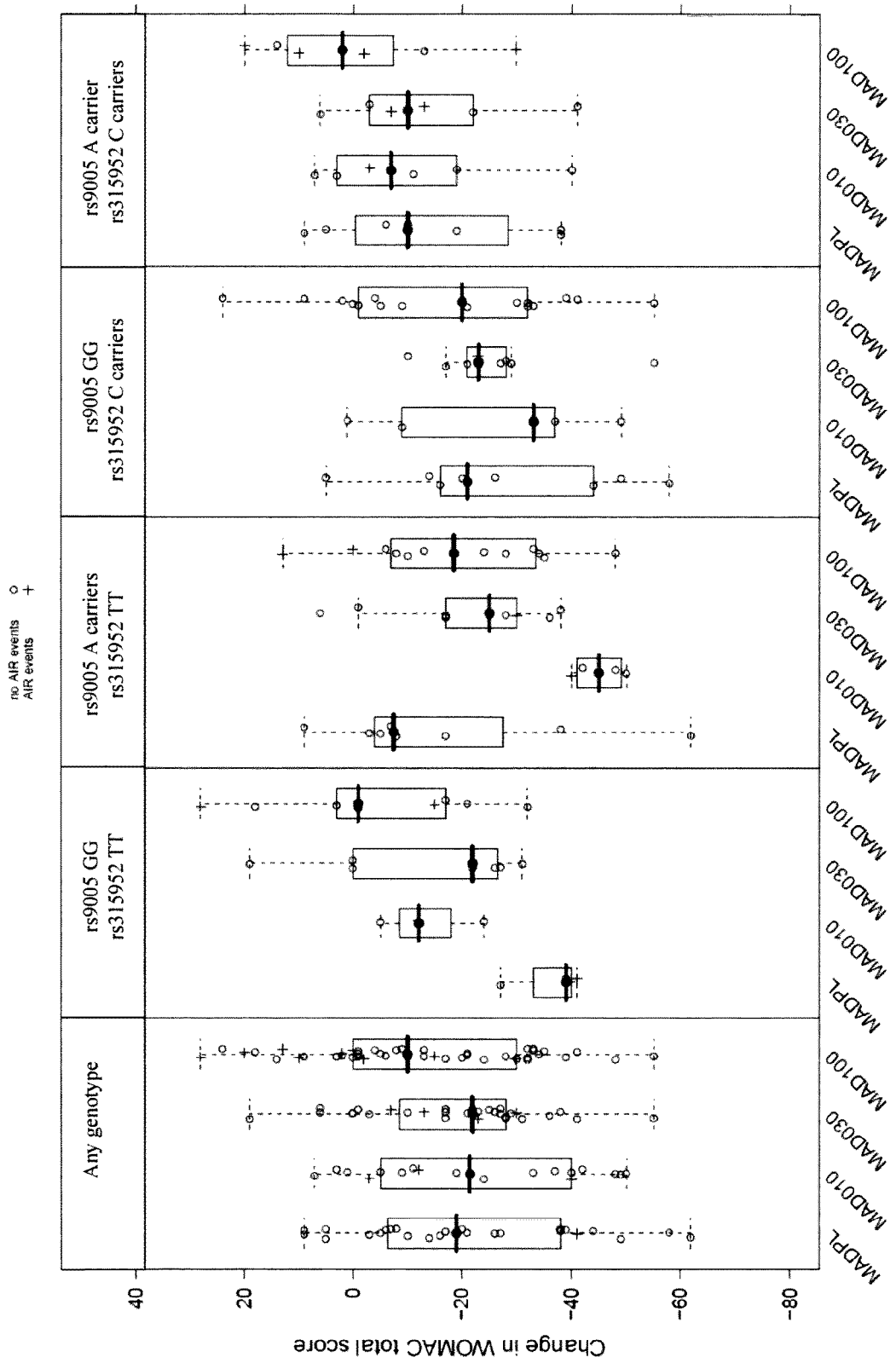
FIG. 5: Change in WOMAC total score at Week 52 stratified by dose regimen and stratified by their genotype at both rs315952 and rs9005. Each point corresponds to a subject; a circle indicates a subject without AIR while a cross indicates a subject with AIRs.

Combinatorial analyses identified only one combination (IL-1RN rs9005 and IL-1RN rs315259) as significantly associated with AIRs (FDR from multivariate linear model=0.0187, Fisher's exact test p-value=0.0018, odds ratio=18.82 [2.25-260.03]). Contingency table and prediction performance metrics are shown respectively in Table 5 and Table 6. The combination of rs9005 and rs315259 (Table 6) has a better performance at predicting AIRs, compared to the C-T-A haplotype (Table 8; see also contingency table in Table 7). The combination of IL-1RN rs9005 and IL-1RN rs315259 has a very strong specificity (94.44%) and negative predictive value (89.47%), i.e., these biomarkers have a very strong performance at identifying subjects that will not have AIRs. In addition, this combination reveals stratification on total cartilage volume (FIG. 4) and WOMAC total scores (FIG. 5). By contrast, the C-T-A haplotype does not allow such clinical outcome stratification (FIGS. 2 and 3). Indeed, the C-T-A haplotype did not allow stratifying subjects for change in total cartilage volume (FIG. 2) nor change in WOMAC total score (FIG. 3). Thus the C-T-A haplotype was not identified as a good predictor of the response to drug therapy, preferably an anabolic drug such as sprifermin.

3.2. Prognostic Analyses

Placebo subjects with the 'IL-1RN rs9005 G/G and IL-1RN rs315259 T/T' genotype were identified as having significantly higher total cartilage volume than treated subjects from the same genotype group. To follow up on this result, change in WOMAC total score and change in total cartilage volume were modeled in placebo subjects with the following formula:

Rank(change in endpoint)~genotype group+Kellgren-Lawrence grade [2; 3]+Gender [Female; Male]+ Age [<65; ≥65]+BMI [<30, ≥30].

No significant difference in WOMAC total score was found between subjects from the four different genotype groups (p-value=0.63, Table 10). However, significant differences were found in change in total cartilage volume (p-value=0.02, Table 9). Subjects from the 'IL-1RN rs9005 G/G and IL-1RN rs315259 T/T' genotype group have significantly higher total cartilage volume increase compared to subjects from the remaining genotype groups.

Figure 6:
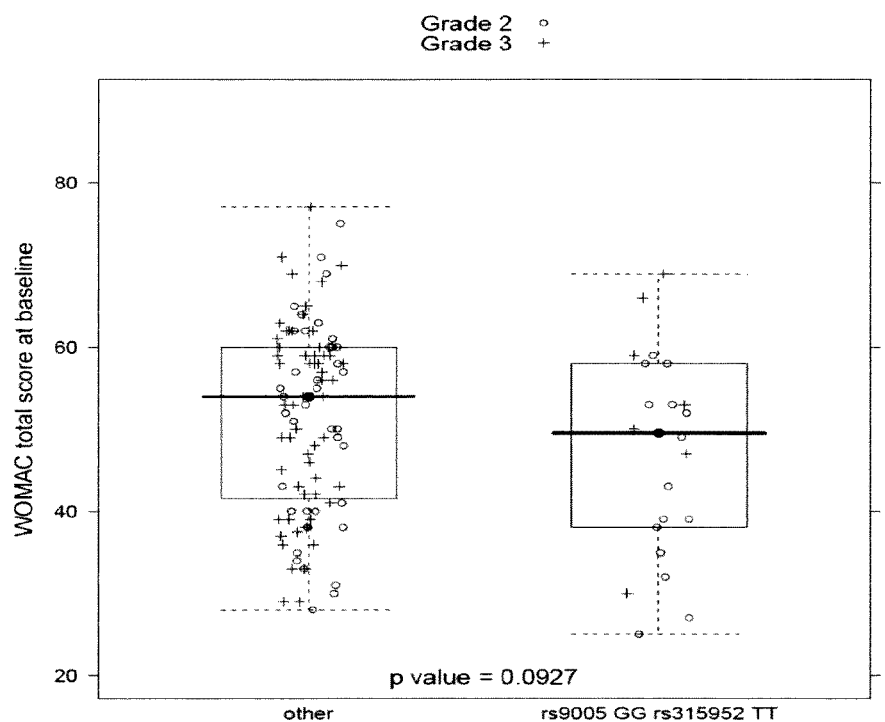
FIG. 6: Stratification of the patients as a function of presence or absence of the 'rs9005 G/G rs315952 T/T' genotype. The Y axis shows absolute WOMAC total score at baseline. Each point corresponds to a subject; a circle indicates a subject with Kellgren-Lawrence grade equal to 2 while a cross indicates a subject with Kellgren-Lawrence grade equal to 3. Indicated p-value was obtained from a non-parametric univariate test (ranksum test).
Figure 8:
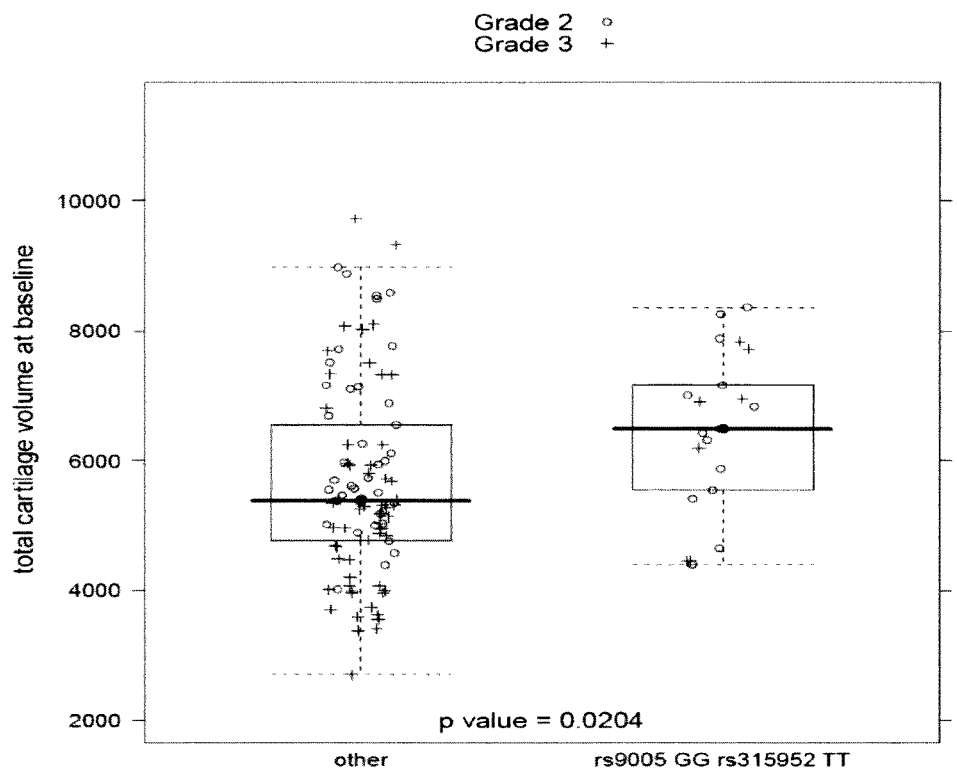
FIG. 8: Stratification of the patients as a function of presence or absence of the 'rs9005 G/G rs315952 T/T' genotype. The Y axis shows absolute total cartilage volume ($mm^3$) at baseline. Each point corresponds to a subject; a circle indicates a subject with Kellgren-Lawrence grade equal to 2 while a cross indicates a subject with Kellgren-Lawrence grade equal to 3. Indicated p-value was obtained from a non-parametric univariate test (ranksum test).

An independent test between the Kellgren-Lawrence grade and subjects from a given genotype group demonstrated that the 'IL-1RN rs9005 G/G and IL-1RN rs315259 T/T' genotype group has a significant paucity in subjects from Kellgren-Lawrence grade 3 (Fisher's exact test p-value=0.0179, Table 11). The corresponding odds ratio is 0.306 (with 95% confidence intervals [0.096, 0.885]). This demonstrates that subjects from the 'IL-1RN rs9005 G/G and IL-1RN rs315259 T/T' genotype group are classified with a less severe osteoarthritis condition than subjects from other genotype groups. Lending support to this result, subjects from the 'IL-1RN rs9005 G/G and IL-1RN rs315259 T/T' genotype group have marginally smaller baseline WOMAC total scores than subjects from other genotype groups (ranksum p-value=0.0927, see FIG. 6). In addition, subjects from the 'IL-1RN rs9005 G/G and IL-1RN rs315259 T/T' genotype group have significantly higher baseline total cartilage volume than subjects from other genotype groups (ranksum p-value=0.0204, see FIG. 8).

Figure 7:
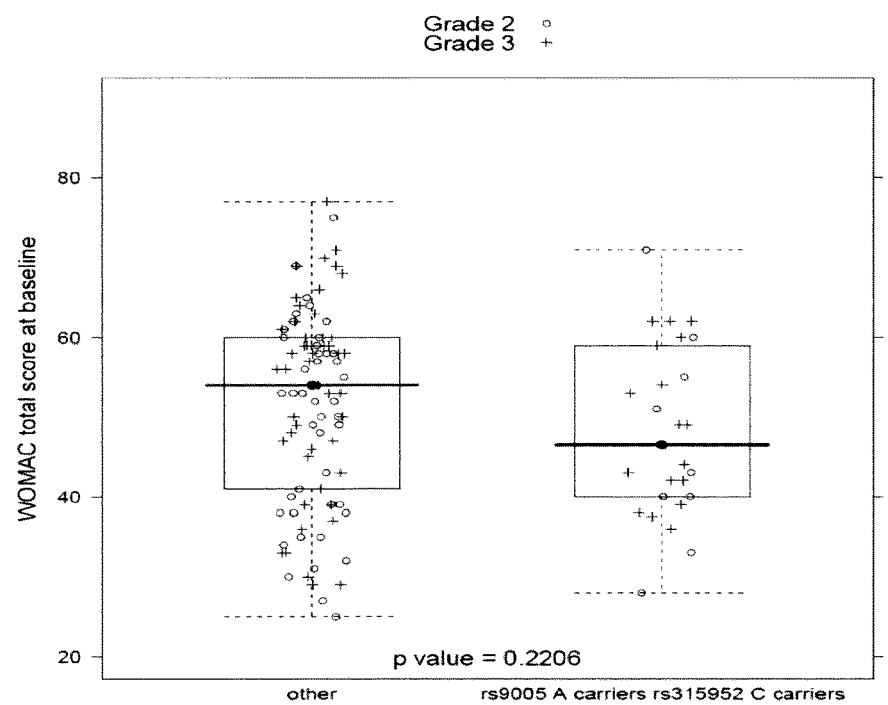
FIG. 7: Stratification of the patients as a function of presence or absence of the 'rs9005 A carriers rs315952 C carriers' genotype. The Y axis shows absolute WOMAC total score at baseline. Each point corresponds to a subject; a circle indicates a subject with Kellgren-Lawrence grade equal to 2 while a cross indicates a subject with Kellgren-Lawrence grade equal to 3. Indicated p-value was obtained from a non-parametric univariate test (ranksum test).
Figure 9:
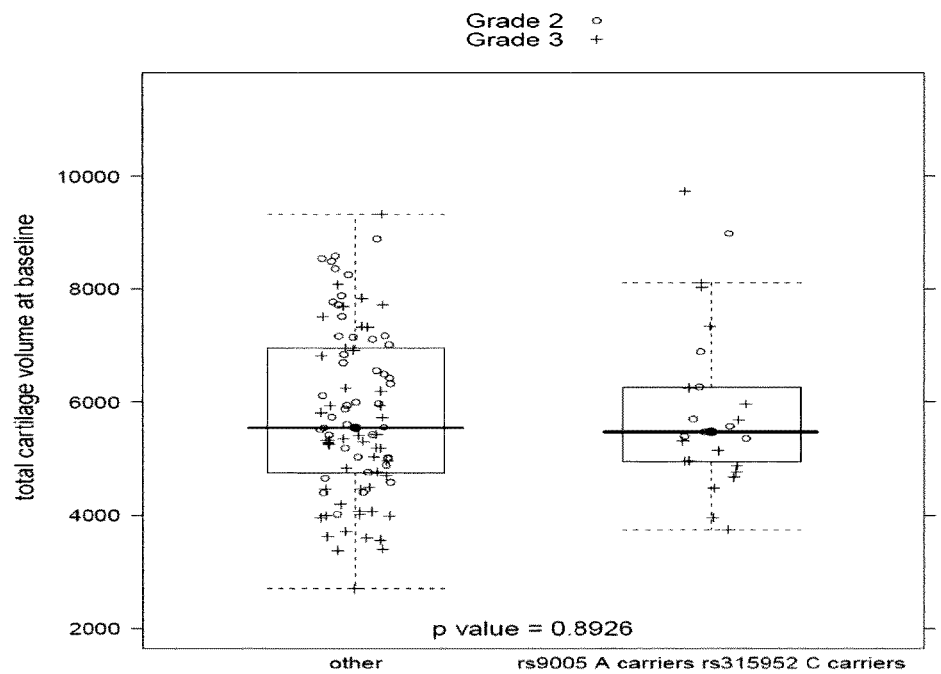
FIG. 9: Stratification of the patients as a function of presence or absence of the 'rs9005 A carriers rs315952 C carriers' genotype. The Y axis shows absolute total cartilage volume ($mm^3$) at baseline. Each point corresponds to a subject; a circle indicates a subject with Kellgren-Lawrence grade equal to 2 while a cross indicates a subject with Kellgren-Lawrence grade equal to 3. Indicated p-value was obtained from a non-parametric univariate test (ranksum test).

Interestingly, there was no difference in the proportion of subjects with Kellgren-Lawrence grade 3 between the 'IL-1RN rs9005 A carriers and IL-1RN rs315259 C carriers' genotype group (aka super-sensitives) and subjects from the remaining genotype groups (Fisher's exact test p-value=0.2736, odds ratio=1.693 [0.637, 4.769], Table 12). Thus the super-sensitive group is not enriched in subjects with severe osteoarthritis conditions. This is further enforced with the fact that both baseline WOMAC total scores and baseline total cartilage volume are comparable between super-sensitive subjects and other subjects (see FIGS. 7 and 9).

Analysis with the C-T-A haplotype did not reveal a difference in the proportion of subjects with Kellgren-Lawrence grade 3 and bearing at least one copy of the C-T-A haplotype (Fisher's exact test p-value=1).

3.3. Clinical Outcome Using the Proposed Genetic Diagnostic Test

Figure 10:
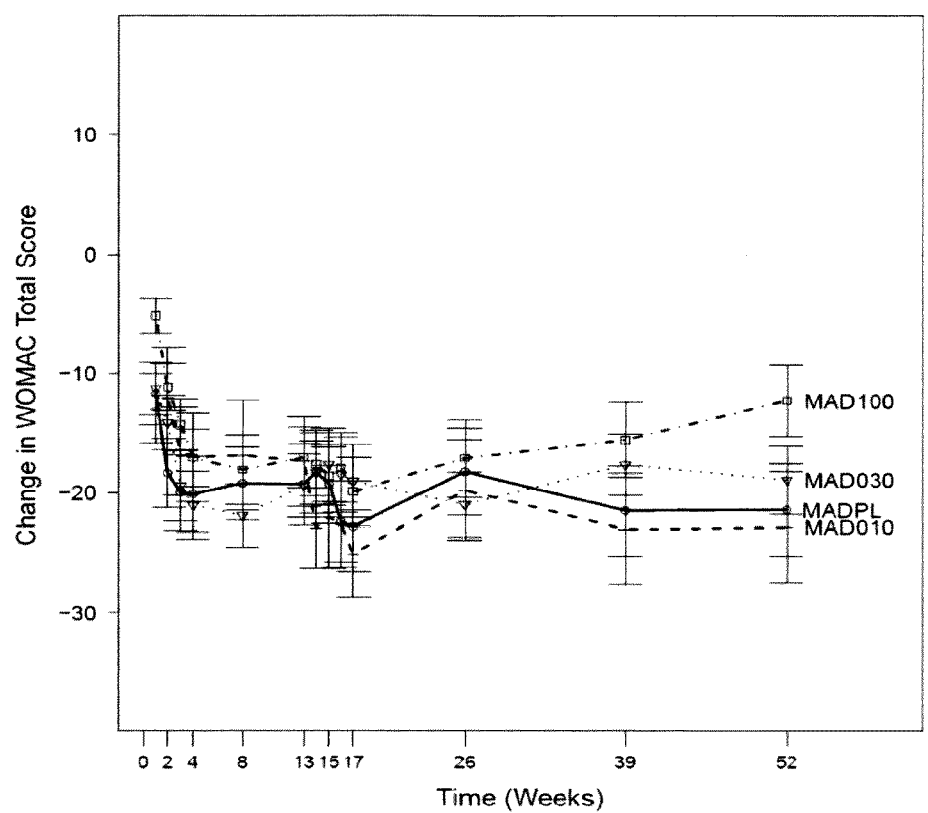
FIG. 10: Change from baseline in WOMAC total score for all subjects irrespective of their genotypes. Lines correspond to the mean change from baseline and error bars correspond to standard error of mean.
Figure 11:
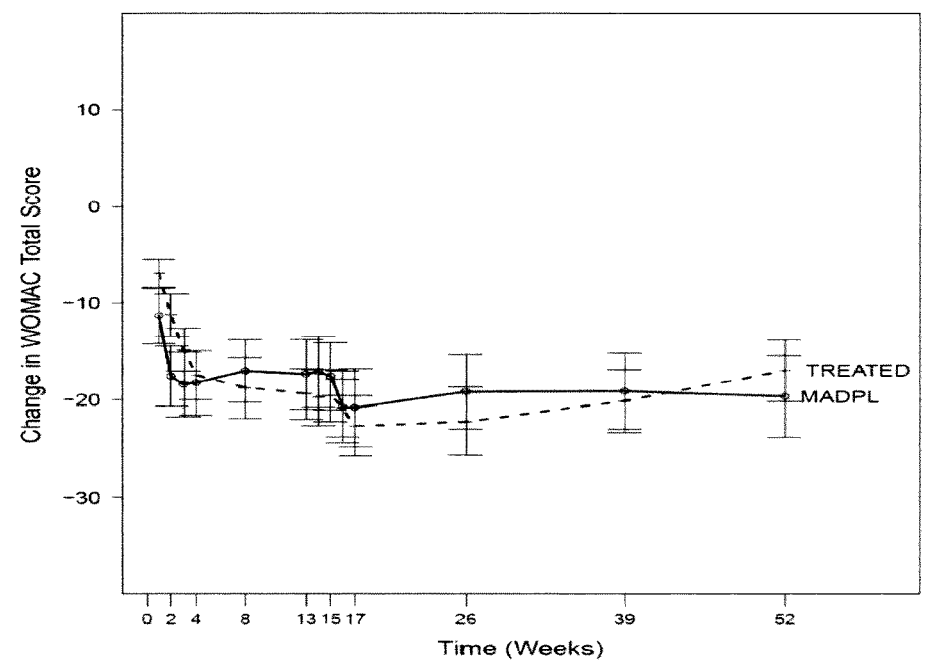
FIG. 11: Change from baseline in WOMAC total score for subjects identified as sensitives or super-sensitives based on their rs9005 and rs315952 genotypes. The 'treated' group corresponds to subjects from the MAD100 cohort having the genotype identifying sensitive subjects. Subjects from the MAD030 cohort having the genotype identifying super-sensitive subjects are also included in this 'treated' group. The 'placebo' group includes placebo subjects with genotypes corresponding to either the sensitives or to the super-sensitives. Lines correspond to the mean change from baseline and error bars correspond to standard error of mean.
Figure 12:
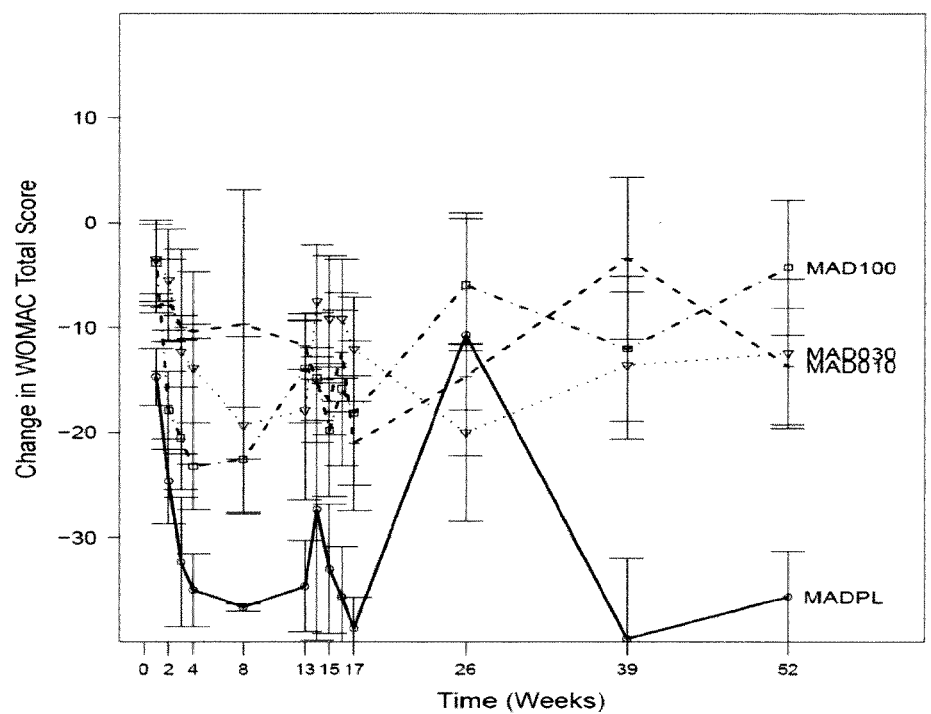
FIG. 12: Change from baseline in WOMAC total score for subjects having the genotype corresponding to the non-sensitives. Lines correspond to the mean change from baseline and error bars correspond to standard error of mean.
Figure 13:
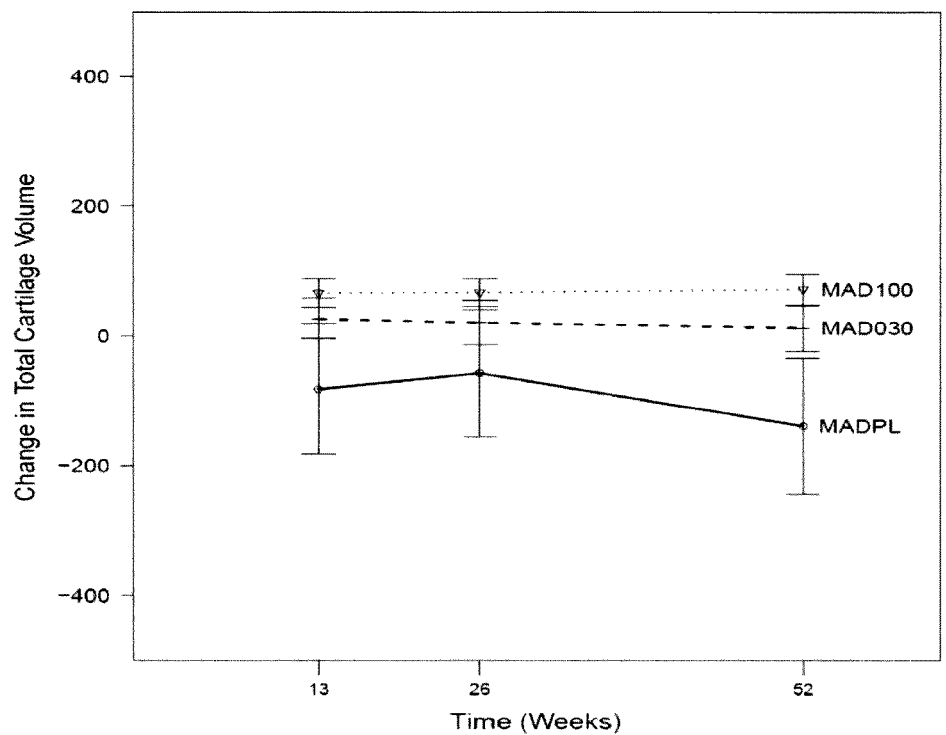
FIG. 13: Change from baseline in total cartilage volume ($mm^3$) for all subjects irrespective of their genotypes. Lines correspond to the mean change from baseline and error bars correspond to standard error of mean. MRI data from the MAD010 cohort showed aberrant variability and were not included in any analyses.
Figure 14:
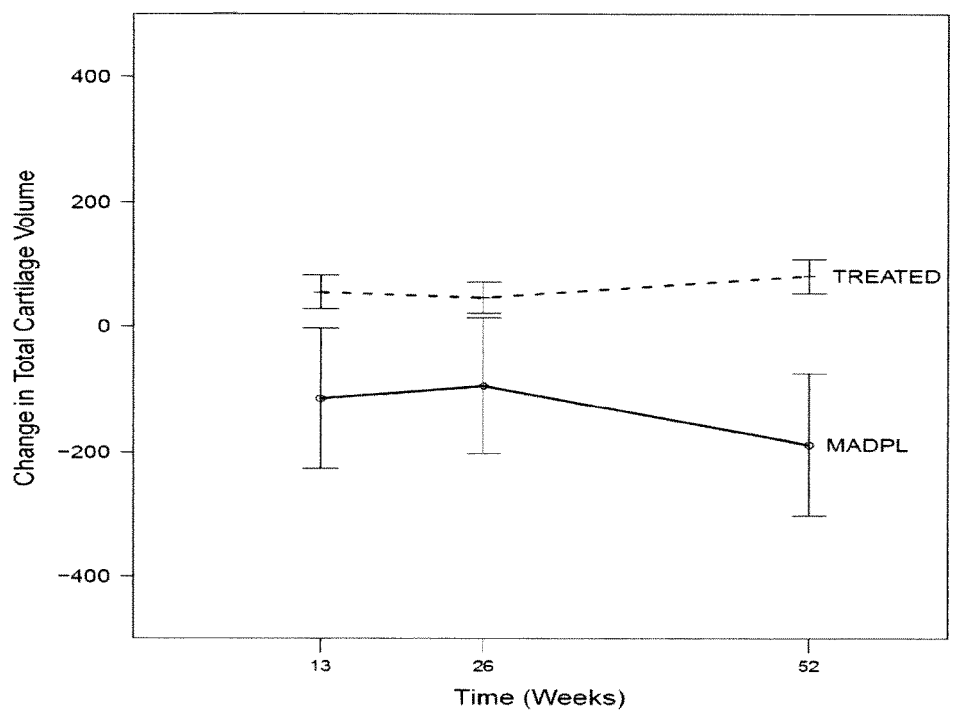
FIG. 14: Change from baseline in total cartilage volume ($mm^3$) for subjects identified as sensitives or super-sensitives based on their rs9005 and rs315952 genotypes. The 'treated' group corresponds to subjects from the MAD100 cohort having the genotype identifying sensitives. Subjects from the MAD030 cohort having the genotype identifying super-sensitives are also included in this 'treated' group. The 'placebo' group includes placebo subjects with genotypes corresponding to either the sensitives or to the super-sensitives. Lines correspond to the mean change from baseline and error bars correspond to standard error of mean. MRI data from the MAD010 cohort did not pass quality control and were not included in any analyses.

Without any genetic stratification, the clinical outcomes of the FGF-18 therapy are the following: 1) significant increase in total cartilage volume (i.e., cartilage repair) in treated subjects (MAD100) compared to placebos (p-value=0.0157); 2) marginally smaller improvement in WOMAC total scores in treated subjects (MAD100) compared to placebos (p-value=0.1044); and 3) 20% of AIRs in treated subjects. These results are summarized in Table 13 and detailed results are presented in Table 14 and Table 15. FIGS. 10 and 13 are also provided for data visualization. It is understood that FIGS. 10 to 15 do not correspond to the multivariate linear model used for the analyses. These figures are only provided to facilitate results interpretation.

The proposed diagnostic test (Table 4) aims at:
1. Identifying sensitives and treating them with the proposed FGF-18 dose (e.g., 100 mcg)
2. Identifying super-sensitives and treating them with a lower FGF-18 dose (e.g., 30 mcg), and
3. Identifying non-sensitives and excluding them from FGF-18 therapy. Retrospectively, the clinical outcomes for subjects elected for FGF-18 therapy are:
1. Significant increase in total cartilage volume in treated subjects (sensitives from MAD100 cohort+super-sensitives from MAD030 cohort) compared to matched placebos (p-value=0.0016 Table 18, FIG. 14). Simulation studies (bootstrap) showed that this cartilage volume improvement is significantly higher than the improvement obtained when no diagnostic test is used (p-value<1E-4).
2. Comparable improvement in WOMAC total scores between treated subjects and placebos (p-value=0.6603, Table 17, FIG. 11).
3. 11.43% of AIRs in treated subjects (Table 16).

Figure 15:
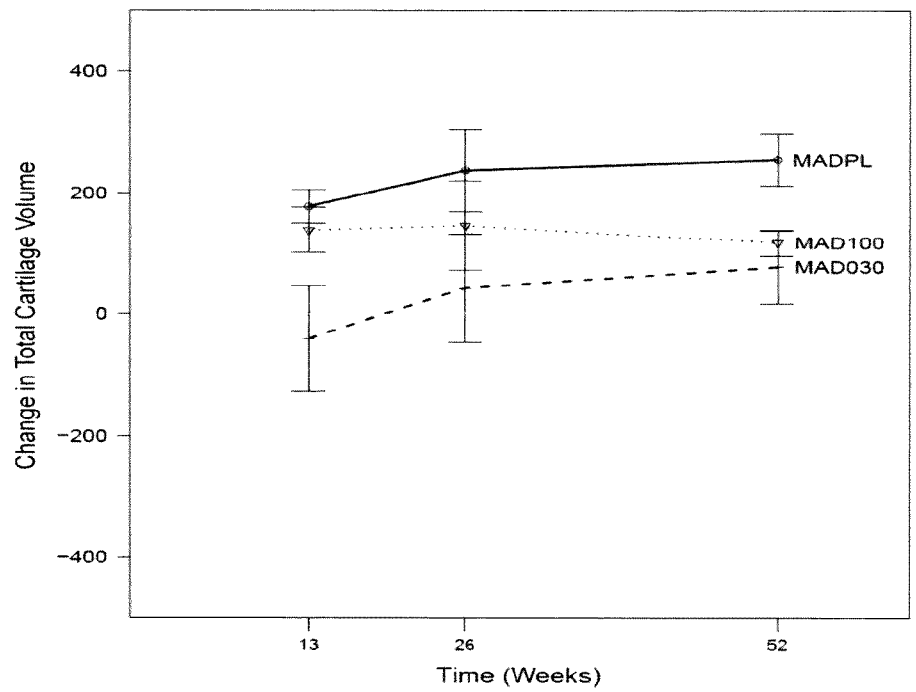
FIG. 15: Change from baseline in total cartilage volume ($mm^3$) for subjects having the genotype corresponding to the non-sensitives. Lines correspond to the mean change from baseline and error bars correspond to standard error of mean. MRI data from the MAD010 cohort showed aberrant variability and were not included in any analyses.

In contrast, subjects identified as non-sensitives have the following clinical outcomes:
1. Significantly lower improvement in total cartilage volume in treated subjects (non-sensitives from MAD100 cohort) compared to matched placebos (p-value=0.0289, Table 21). Subjects from the MAD030 cohort had similar outcomes to subjects from the MAD100 cohort (FIG. 15). Thus none of the investigated doses showed an improvement with respect to placebos.
2. Although the p-value from the multivariate linear model is not significant (p-value=0.3068, Table 20), there is no improvement in WOMAC total score for treated subjects (median change=−1), while there is some improvement for placebos (median change=−39). Subjects from the MAD010 and MAD030 cohorts had similar outcomes to subjects from the MAD100 cohort (FIG. 12). Thus none of the investigated doses showed an improvement with respect to placebos.
3. 22.22% of AIRs in treated subjects (Table 19).

Tables

TABLE 1

List of candidate SNPs

| Gene/description | Tested SNPs |
|---|---|
| FGF-18 | rs3806929, rs4073716, rs9313543, rs4076077, rs4073717, rs6555956, rs10065728, rs4620037, rs11553493 |
| FGFR1 | rs2288696, rs2978073, rs11777067, rs6983315, rs7012413, rs6996321 |
| FGFR2 | rs3135810, rs2278202, rs1649200, rs7090018, rs2912759, rs2912787, rs2981449, rs2981432, rs10736303, rs1078806, rs2981575, rs1219648, rs1219643, rs2912774, rs2162540, rs2981582, rs3135715, rs3750819, rs755793 |
| FGFR3 | rs17880763, rs17881656, rs17882190, rs17884368 |
| FGFR4 | rs442856, rs422421, rs2011077 |
| FGFRL1 | rs4647934 |
| IL10 | rs1878672, rs3024493, rs1554286, rs3024491, rs3024490 |
| IL1A | rs1304037, rs3783550, rs3783525, rs1800587 |
| IL1B | rs1143627, rs1143634, rs1143633, rs3136558 |
| IL1RN | rs9005, rs315952, rs444413, rs3181052, rs419598, rs423904, rs442710, rs447713, rs451578, rs432014, rs431726, rs452204, rs3087266, rs579543 |
| IL6 | rs1800795, rs1800797, rs1474347, rs2069840, rs1800796 |
| marginal association with AIRs (from whole-genome scan) | rs5934659, rs12407610, rs1344049, rs10954969, rs1522844, rs2685592, rs6697273, rs887071, rs1105227, rs6846033, rs871746, rs11815080, rs6949763, rs897718, rs7651624, rs6989732, rs7786717, rs10093384, rs11737974, rs3122569, rs12453065, rs1992509, rs2202731, rs6897534, rs747159, rs4342357, rs2447011, rs4770271, rs10430746, rs7032155, rs10948190, rs7073333, rs6495812, rs946120, rs1047813, rs2032790, rs3865404, rs11040899, rs1968294, rs723077 |
| marginal association with WOMAC total score (from whole-genome scan) | rs12410403, rs587505, rs9902708, rs734397, rs894013, rs932241 |
| TNFRS1B | rs1061622 |
| VDR region | rs731236, rs7975232, rs1544410 |

TABLE 2a

Details of TaqMan SNP Id screened in period 1

| Gene Symbol | rs Id | Assay Id | NCBI alleles | Assay type |
|---|---|---|---|---|
| FGF-18 | rs4073716 | C__27537611_10 | C/T | Functionally Tested |
| FGF-18 | rs11553493 | NA | G/T | Custom |
| FGF-18, NPM1 | rs3806929 | C__11274941_10 | C/T | Functionally Tested |
| FGFR2 | rs755793 | C__2414603_10 | C/T | Validated |
| FGFR3 | rs17881656 | NA | C/T | Custom |
| FGFR3, LETM1 | rs17880763 | C__58182661_10 | A/T | Functionally Tested |
| FGFR3, LETM1 | rs17882190 | C__58182657_10 | A/G | Functionally Tested |
| IL1B | rs1143627 | C__1839944_10 | C/T | Validated |
| IL-6 | rs1800795 | hCV1839697 | C/G | Custom/SNPlex system |
| IL6, LOC541472 | rs1800796 | C__11326893_10 | C/G | Functionally Tested |
| LETM1, FGFR3 | rs17884368 | C__58182646_10 | A/G | Functionally Tested |
| LOC100131885, FGFR2 | rs3750819 | C__27511529_10 | C/G | Functionally Tested |
| LOC541472, IL6 | rs1800797 | C__1839695_20 | A/G | Functionally Tested |
| TNFRSF1B | rs1061622 | C__8861232_20 | G/T | Functionally Tested |
| VDR | rs7975232 | C__28977635_10 | A/C | Functionally Tested |
| VDR | rs731236 | C__2404008_10 | C/T | Functionally Tested |
| VDR | rs1544410 | C__8716062_10 | A/G | Validated |

TABLE 2b

Details of TaqMan SNP Id screened in period 2

| Gene Symbol | rs Id | Assay Id | NCBI alleles | Assay type |
|---|---|---|---|---|
| IL1RN | rs9005 | C__3133528_10 | A/G | Functionally Tested |
| IL1RN | rs315952 | C__11512470_10 | C/T | Validated |

TABLE 3

Taqman primer sequences

| SNP Reference | Applied Biosystems assay ID | Primer sequences |
|---|---|---|
| rs315952 | C_11512470_10 | Primer 1: GCTTCGCCTTCATCCG CTCAGACAG or complementary sequence<br>Primer 2: GGCCCCACCACCAGTT TTGAGTCTG or complementary sequence |
| rs9005 | C_3133528_10 | Primer 1: TGTGCCTCTGCCTGTC TCCCCCACC or complementary sequence<br>Primer 2: GGCTGGGAGCTCTGCA GAGCAGGAA or complementary sequence |

TABLE 4

Identified genotype categories in the Multiple Ascending Dose cohort (100 mcg)

| | | rs9005 (A/G) | |
|---|---|---|---|
| | | G/G | A carriers |
| rs315952 (T/C) | T/T | group A: non-sensitives (20% of MAD100) | group B: Sensitives (27% of MAD100) |
| | C carriers | group C: Sensitives (38% of MAD100) | group D: super-sensitives (15% of MAD100) |

TABLE 5

Contingency table: AIR predictions based on rs9005 and rs315952 genotypes with subjects from the FGF-18 MAD100 arm (n = 45)

| | | True AIR status | |
|---|---|---|---|
| | | Subjects with AIRs | Subjects without AIRs |
| Predicted status | Predicted with AIRs | 5 | 2 |
| | Predicted without AIRs | 4 | 34 |

TABLE 6

Performance at predicting AIRs based on rs9005 and rs315952 genotypes with subjects from the FGF-18 MAD100 arm (n = 45)

| Performance metrics | value |
|---|---|
| Sensitivity | 55.56% |
| Accuracy | 86.67% |
| Specificity | 94.44% |
| Precision | 71.43% |

TABLE 6-continued

Performance at predicting AIRs based on rs9005 and rs315952 genotypes with subjects from the FGF-18 MAD100 arm (n = 45)

| Performance metrics | value |
|---|---|
| Negative predictive value | 89.47% |
| Sensitivity and precision (F1 score) | 62.50% |

TABLE 7

Contingency table: AIR predictions based on presence/absence of the C-T-A haplotype with subjects from the FGF-18 MAD100 arm (n = 48)

| | | True AIR status | |
|---|---|---|---|
| | | Subjects with AIRs | Subjects without AIRs |
| Predicted status | Predicted with AIRs | 6 | 7 |
| | Predicted without AIRs | 4 | 31 |

TABLE 8

Performance at predicting AIRs based on presence/absence of the C-T-A haplotype with subjects from the FGF-18 MAD100 arm (n = 48)

| Performance metrics | value |
|---|---|
| Sensitivity | 60% |
| Accuracy | 77.08% |
| Specificity | 81.58% |
| Precision | 46.15% |
| Negative predictive value | 88.57% |
| Sensitivity and precision (F1 score) | 52.17% |

TABLE 9

Multivariate linear modeling for change in total cartilage volume with placebo subjects only

| model term | regression coefficient | Standard Error | Z-score | p-value |
|---|---|---|---|---|
| Intercept | 78.44 | 23.68 | 3.31 | 0.0035 |
| group [B-C-D; A only] | 83.11 | 33.85 | 2.46 | 0.0234 |
| Kellgren-Lawrence grade [2; 3] | −12.93 | 22.36 | −0.58 | 0.5695 |
| Age [<65; >= 65] | −15.83 | 20.86 | −0.76 | 0.4569 |
| BMI [<30; >= 30] | 4.02 | 21.61 | 0.19 | 0.8545 |
| Gender [Female; Male] | −15.01 | 20.31 | −0.74 | 0.4683 |

TABLE 10

Multivariate linear modeling for change in WOMAC total score with placebo subjects only

| model term | regression coefficient | Standard Error | Z-score | p-value |
|---|---|---|---|---|
| Intercept | 63.76 | 20.40 | 3.13 | 0.0051 |
| group [B-C-D; A only] | −13.98 | 28.71 | −0.49 | 0.6313 |
| Kellgren-Lawrence grade [2; 3] | −25.47 | 18.83 | −1.35 | 0.1906 |
| Age [<65; >= 65] | 0.34 | 17.66 | 0.02 | 0.9847 |
| BMI [<30; >= 30] | 46.97 | 18.08 | 2.60 | 0.0168 |
| Gender [Female; Male] | 29.74 | 17.01 | 1.75 | 0.0950 |

TABLE 11

Contingency table: Kellgren-Lawrence grade (3 or 2) based on presence/absence of the 'rs9005 G/G rs315952 TT' genotype - Analysis was performed using all subjects from all dose regimen (including placebos). Fisher's exact test p-value is 0.0179, odds ratio is 0.306 with 95% confidence interval [0.096, 0.885].

| genotype | Grade 3 | Grade 2 |
|---|---|---|
| rs9005 G/G rs315952 T/T | 7 | 15 |
| other | 60 | 39 |

TABLE 12

Contingency table: Kellgren-Lawrence grade (3 or 2) based on presence/absence of the 'rs9005 A carriers rs315952 C carriers' genotype - Analysis was performed using all subjects from all dose regimen (including placebos). Fisher's exact test p-value is 0.2736, odds ratio is 1.693 with 95% confidence interval [0.637, 4.769].

| genotype | Grade 3 | Grade 2 |
|---|---|---|
| rs9005 A carriers rs315952 C carriers | 17 | 9 |
| other | 50 | 45 |

TABLE 13

Clinical outcome without diagnostic test (45 subjects treated with FGF-18 100 mcg and 27 placebos) - Delta corresponds to the difference between the median change in placebos and the median change in treated subjects. P-value corresponds to the p-value from a multivariate linear model adjusting for gender, age, BMI and KL grade.

| Groups A, B, C, D | median change in placebos | median change in treated subjects (MAD100) | delta | p-value |
|---|---|---|---|---|
| Change in WOMAC total score | −19 | −10 | 9 | 0.1044 |
| Change in total cartilage volume | −44.68 | 102.25 | 146.93 | 0.0157 |
| % AIRs | 3.7 | 20 | 16.3 | NA |

TABLE 14

Multivariate linear modeling for change in WOMAC total score with all placebos and all MAD100 treated subjects

| model term | regression coefficient | Standard Error | Z-score | p-value (GLM) | LR Chi-square (anova) | p-value (anova) |
|---|---|---|---|---|---|---|
| Intercept | 59.51 | 14.86 | 4.00 | 0.0002 | NA | NA |
| Age [<65; >=65] | 11.07 | 12.61 | 0.88 | 0.3834 | 0.77 | 0.3802 |
| Arm (dose 100 mcg) | 19.51 | 12.02 | 1.62 | 0.1091 | 2.64 | 0.1044 |
| BMI [<30; >=30] | 13.24 | 12.09 | 1.10 | 0.2774 | 1.20 | 0.2734 |
| Gender [Female; Male] | 20.13 | 11.84 | 1.70 | 0.0937 | 2.89 | 0.0890 |
| Kellgren-Lawrence grade [2; 3] | 0.14 | 11.79 | 0.01 | 0.9902 | 0.00 | 0.9902 |

TABLE 15

Multivariate linear modeling for change in total cartilage volume with all placebos and all MAD100 treated subjects

| model term | regression coefficient | Standard Error | Z-score | p-value (GLM) | LR Chi-square (anova) | p-value (anova) |
|---|---|---|---|---|---|---|
| Intercept | 79.10 | 13.37 | 5.92 | 0.0000 | NA | NA |
| Age [<65; >=65] | −15.10 | 11.35 | −1.33 | 0.1878 | 1.77 | 0.1832 |
| Arm [placebos; treated] | 26.12 | 10.81 | 2.42 | 0.0185 | 5.84 | 0.0157 |
| BMI [<30; >=30] | −14.60 | 10.87 | −1.34 | 0.1841 | 1.80 | 0.1795 |
| Gender [Female; Male] | 1.05 | 10.65 | 0.10 | 0.9216 | 0.01 | 0.9213 |
| Kellgren-Lawrence grade [2; 3] | −1.25 | 10.61 | −0.12 | 0.9065 | 0.01 | 0.9061 |

TABLE 16

Clinical outcome for subjects classified as 1) sensitives (groups B and C, n = 29, treated with FGF-18 100 mcg) or 2) super-sensitives (group D, n = 6, treated with a lower FGF-18 dose: 30 mcg). 24 placebos, with genotypes from either group B, C or D, were included in the analysis - Delta corresponds to the difference between the median change in placebos and the median change in treated subjects. P-value corresponds to the p-value from a multivariate linear model adjusting for gender, age, BMI and KL grade.

| Groups B, C, D | median change in placebos | median change in treated subjects (MAD100 + MAD30) | delta | p-value |
|---|---|---|---|---|
| Change in WOMAC total score | −16.5 | −13 | 3.5 | 0.6603 |
| Change in total cartilage volume | −114.91 | 102.25 | 217.16 | 0.0016 |
| % AIRs | 0 | 11.43 | 11.43 | NA |

TABLE 17

Multivariate linear modeling for change in WOMAC total score with subjects classified as 1) sensitives (groups B and C, n = 29, treated with FGF-18 100 mcg) or 2) super-sensitives (group D, n = 6, treated with a lower FGF-18 dose: 30 mcg). 24 placebos, with genotypes from either group B, C or D, were included in the analysis.

| model term | regression coefficient | Standard Error | Z-score | p-value (GLM) | LR Chi-square (anova) | p-value (anova) |
|---|---|---|---|---|---|---|
| Intercept | 67.09 | 16.25 | 4.13 | 0.0001 | NA | NA |
| Age [<65; >=65] | 7.23 | 13.33 | 0.54 | 0.5900 | 0.29 | 0.5877 |
| Arm [placebos; treated] | 5.82 | 13.24 | 0.44 | 0.6621 | 0.19 | 0.6603 |
| BMI [<30; >=30] | 3.87 | 12.82 | 0.30 | 0.7641 | 0.09 | 0.7629 |
| Gender [Female; Male] | 16.54 | 13.68 | 1.21 | 0.2322 | 1.46 | 0.2268 |
| Kellgren-Lawrence grade [2; 3] | 6.67 | 13.09 | 0.51 | 0.6124 | 0.26 | 0.6103 |

TABLE 18

Multivariate linear modeling for change in total cartilage volume with subjects classified as 1) sensitives (groups B and C, n = 29, treated with FGF-18 100 mcg) or 2) super-sensitives (group D, n = 6, treated with a lower FGF-18 dose: 30 mcg). 24 placebos, with genotypes from either group B, C or D, were included in the analysis.

| model term | regression coefficient | Standard Error | Z-score | p-value (GLM) | LR Chi-square (anova) | p-value (anova) |
|---|---|---|---|---|---|---|
| Intercept | 64.94 | 14.46 | 4.49 | 0.0000 | NA | NA |
| Age [<65; >=65] | −15.89 | 11.86 | −1.34 | 0.1860 | 1.79 | 0.1803 |
| Arm [placebos; treated] | 37.14 | 11.78 | 3.15 | 0.0027 | 9.94 | 0.0016 |
| BMI [<30; >=30] | −5.47 | 11.40 | −0.48 | 0.6332 | 0.23 | 0.6312 |
| Gender [Female; Male] | 1.14 | 12.18 | 0.09 | 0.9258 | 0.01 | 0.9254 |
| Kellgren-Lawrence grade [2; 3] | 1.27 | 11.65 | 0.11 | 0.9137 | 0.01 | 0.9133 |

TABLE 19

Clinical outcome for subjects classified as non-sensitives by the diagnostic test (MAD100 n = 9, MADPL n = 3) - Delta corresponds to the difference between the median change in placebos and the median change in treated subjects. P-value corresponds to the p-value from a multivariate linear model adjusting for gender, age, BMI and KL grade.

| Group A only | median change in placebos | median change in treated subjects (MAD100) | delta | p-value |
|---|---|---|---|---|
| Change in WOMAC total score | −39 | −1 | 38 | 0.3068 |
| Change in total cartilage volume | 224.56 | 117.92 | −106.64 | 0.0289 |
| % AIRs | 33.33 | 22.22 | −11.11 | NA |

TABLE 20

Multivariate linear modeling for change in WOMAC total score, with subjects classified as non-sensitives by the diagnostic test (MAD100 n = 9, MADPL n = 3)

| model term | regression coefficient | Standard Error | Z-score | p-value (GLM) | LR Chi-square (anova) | p-value (anova) |
|---|---|---|---|---|---|---|
| Intercept | 38.99 | 40.18 | 0.97 | 0.3693 | NA | NA |
| Age [<65; >=65] | 1.62 | 45.92 | 0.04 | 0.9730 | 0.00 | 0.9718 |
| Arm [placebos; treated] | 43.10 | 42.18 | 1.02 | 0.3462 | 1.04 | 0.3068 |
| BMI [<30; >=30] | 18.24 | 38.93 | 0.47 | 0.6558 | 0.22 | 0.6393 |
| Gender [Female; Male] | 43.01 | 33.47 | 1.29 | 0.2461 | 1.65 | 0.1987 |
| Kellgren-Lawrence grade [2; 3] | −19.53 | 34.44 | −0.57 | 0.5911 | 0.32 | 0.5706 |

TABLE 21

Multivariate linear modeling for change in total cartilage volume with subjects classified as non-sensitives by the diagnostic test (MAD100 n = 9, MADPL n = 3)

| model term | regression coefficient | Standard Error | Z-score | p-value (GLM) | LR Chi-square (anova) | p-value (anova) |
|---|---|---|---|---|---|---|
| Intercept | 128.67 | 15.26 | 8.43 | 0.0002 | NA | NA |
| Age [<65; >=65] | 47.00 | 17.44 | 2.70 | 0.0358 | 7.27 | 0.0070 |
| Arm [placebos; treated] | −35.00 | 16.02 | −2.19 | 0.0715 | 4.78 | 0.0289 |
| BMI [<30; >=30] | 30.67 | 14.78 | 2.07 | 0.0834 | 4.30 | 0.0380 |
| Gender [Female; Male] | −39.00 | 12.71 | −3.07 | 0.0220 | 9.42 | 0.0022 |
| Kellgren-Lawrence grade [2; 3] | 7.00 | 13.08 | 0.54 | 0.6117 | 0.29 | 0.5925 |

TABLE 22

Summary of clinical outcome and potential therapeutic options based on rs9005 and rs315952 genotypes

|  | Group A | Groups B & C | Group D | |
|---|---|---|---|---|
|  | 100 mcg | 100 mcg | 100 mcg | 30 mcg |
| Change in WOMAC total score | Significant WOMAC worsening compared to placebo | Change in WOMAC comparable to placebo | Change in WOMAC higher than placebo | Change in WOMAC comparable to placebo |
| Change in total cartilage volume | No improvement | Significant cartilage volume improvement | Significant cartilage volume improvement (highest gain among all groups treated at 100 mcg) | Highest cartilage volume improvement (significantly better than 100 mcg) |
| AIRs | 2/9 treated subjects (1/3 in placebos) | 2/29 treated subjects (0/17 in placebos) | 5/7 treated subjects (0/7 in placebos) | 2/6 treated subjects (0/7 in placebos) |

TABLE 22-continued

Summary of clinical outcome and potential therapeutic options based on rs9005 and rs315952 genotypes

|  | Group A | Groups B & C | Group D | |
|---|---|---|---|---|
|  | 100 mcg | 100 mcg | 100 mcg | 30 mcg |
| Potential therapeutic option | Do not benefit from FGF-18 therapy | Treat up to 100 mcg | Treat at 30 mcg | |

REFERENCES

1) WO 2008/023063
2) WO 2004/032849
3) WO 2006/063362
4) WO 2009/135218
5) WO 92/15712
6) U.S. Pat. No. 5,679,524
7) WO 91/02087
8) WO 90/09455
9) WO 95/17676
10) U.S. Pat. No. 5,302,509
11) U.S. Pat. No. 5,945,283
12) U.S. Pat. No. 5,605,798
13) WO 89/10414
14) See Worldwide Website: cartilage.orgLfiles/content-management/ICRS_evaluation.pdf.
15) Lotz, 2010, Arthritis research therapy, 12:211.
16) Ellsworth et al., 2002, Osteoarthritis and Cartilage, 10: 308-320.
17) Shimoaka et al., 2002, J. Bio. Chem. 277(9):7493-7500.
18) The Merck Manual, 17$^{th}$ edition, page 449.
19) Bellamy et al., 1988, J. Rheumatology, 15:1833-1840.
20) Wolfe, 1999, Rheumatology, 38:355-361.
21) Attur et al., 2010, Ann. Rheum. Dis., 69:856-861.
22) Li et al., 2010, Genet Epidemiol 34:816-834.
23) Benjamini and Hochberg, 1995, J. of the Royal Statistical Society Series B(57):289.
24) Wirapati et al., 2011, Ann. Hum. Genet. 75(1):133-45.
25) Bateson W. and Mendel G., 1909, "G. Mendel's principles of heredity". Cambridge University Press. Available: http://archive.org/details/mendelsprinciple00bate.
26) Phillips P. C.,1998, Genetics. 7; 149(3):1167-71.
27) Cordell H. J., 2002, Hum. Mol. Genet. 11(20):2463-8.
28) Fisher R A, 1918, "The Correlation Between Relatives on the Supposition of Mendelian Inheritance". Available: http://digital.library.adelaide.edu.au/dspace/handle/2440/15097.
29) Browning S R and Browning B L, 2011, Nature Reviews Genetics. 12(10):703-14.

The invention claimed is:

1. A method for treating a human having osteoarthritis comprising:
   a) obtaining a nucleic acid sample from a human having osteoarthritis;
   b) assaying said nucleic acid sample to detect the genotypes at IL-1RN rs9005 and IL-1RN rs315952;
   c) identifying the human as being supersensitive to treatment with an FGF-18 compound when the combined genotypes of A/G or A/A at IL-1RN rs9005 and T/C or C/C at IL-1RN rs315952 are detected and intra-articularly administering between 20 and 83.33 mcg of said FGF-18 compound to the human identified as being supersensitive; or
   identifying the human as having intermediate sensitivity to treatment with an FGF-18 compound when the combined genotypes of G/G at IL-1RN rs9005 and T/C or C/C at IL-1RN rs315952 or A/G or A/A at IL-1RN rs9005 and T/T at IL-1RN rs315952 are detected and intra-articularly administering between 60 and 250 mcg of said FGF-18 compound to the human identified as having intermediate sensitivity.

2. The method according to claim 1, wherein said FGF-18 compound is administered in a treatment cycle of once weekly for 3 weeks.

3. The method according to claim 2, wherein the treatment cycle is repeated.

4. The method according to claim 1, wherein a dose of 30 mcg is administered to a human having genotype A/G or A/A at IL-1RN rs9005 and T/C or C/C at IL-1RN rs315952.

5. The method according to claim 1, wherein said FGF-18 compound is sprifermin.

6. The method according to claim 4, wherein said FGF-18 compound is sprifermin.

7. The method according to claim 1, wherein a dose of 100 mcg is administered to a human having genotype G/G at IL-1RN rs9005 and T/C or C/C at IL-1RN rs315952 or A/G or A/A at IL-1RN rs9005 and T/T at IL-1RN 315952.

* * * * *

UNITED STATES PATENT AND TRADEMARK OFFICE
CERTIFICATE OF CORRECTION

PATENT NO. : 10,221,456 B2
APPLICATION NO. : 14/420076
DATED : March 5, 2019
INVENTOR(S) : Christoph Hubertus Ladel et al.

Page 1 of 2

It is certified that error appears in the above-identified patent and that said Letters Patent is hereby corrected as shown below:

On the Title Page

Item (54), Title of Invention:
"GENETIC MARKERS FOR PREDICTING RESPONSIVENESS TO FPG-18 COMPOUND" should read --GENETIC MARKERS FOR PREDICTING RESPONSIVENESS TO FGF-18 COMPOUND--.

In the Specification

Column 8,
Line 3, "preferably about" should read --preferably $\leq$ about--.

Column 25,
Lines 6-7, "IL1RN-r5315952" should read --IL1RN-rs315952--.

Column 31,
Line 14, "Wrapati et al." should read --Wirapati et al.--.

Column 35,
Line 19, "CTCAGACAG or" should read --CTCAGACAG (SEQ ID NO: 8) or--.

Column 35,
Line 22, "TTGAGTCTG or" should read --TTGAGTCTG (SEQ ID NO: 9) or--.

Column 35,
Line 24, "TCCCCCACC or" should read --TCCCCCACC (SEQ ID NO: 10) or--.

Column 35,
Line 27, "GAGCAGGAA or" should read --GAGCAGGAA (SEQ ID NO: 11) or--.

Signed and Sealed this
Thirtieth Day of July, 2019

Andrei Iancu
*Director of the United States Patent and Trademark Office*

CERTIFICATE OF CORRECTION (continued)
U.S. Pat. No. 10,221,456 B2

Column 37,
Line 21, "dose regimen" should read --dose regimens--.

Column 41,
Lines 28-29, "cartilage.orgLfiles/contentmanagement/ICRS_evaluation.pdf." should read
--cartilage.org/_files/contentmanagement/ICRS_evaluation.pdf--.